United States Patent
Yokoyama et al.

[11] Patent Number: 5,977,277
[45] Date of Patent: Nov. 2, 1999

[54] ACRYLIC ESTER, NOVEL ALLYL ETHER, NOVEL ALLYL CARBONATE, ACRYLIC ESTER POLYMER, ALLYL ETHER POLYMER, ALLYL CARBONATE POLYMER AND POLYMERIC SOLID ELECTROLYTE

[75] Inventors: Keiichi Yokoyama; Takako Sasano; Akio Hiwara; Masahiro Toriida; Satoko Mita, all of Sodegaura; Masayoshi Watanabe, Yokohama, all of Japan

[73] Assignee: Mitsui Petrochemical Industries, Ltd, Tokyo, Japan

[21] Appl. No.: 08/845,434

[22] Filed: Apr. 25, 1997

Related U.S. Application Data

[63] Continuation-in-part of application No. 08/817,748, filed as application No. PCT/JP96/02358, Aug. 23, 1996.

[30] Foreign Application Priority Data

| Aug. 23, 1995 | [JP] | Japan | 7-215058 |
| Aug. 23, 1995 | [JP] | Japan | 7-215059 |
| Sep. 8, 1995 | [JP] | Japan | 7-231864 |
| Sep. 8, 1995 | [JP] | Japan | 7-231865 |
| Nov. 8, 1995 | [JP] | Japan | 7-290192 |
| Nov. 8, 1995 | [JP] | Japan | 7-290193 |
| Apr. 26, 1996 | [JP] | Japan | 7-107346 |

[51] Int. Cl.$^6$ ................................. C08F 18/24
[52] U.S. Cl. ................... 526/314; 560/187; 560/225; 524/167; 524/174; 524/401; 524/404; 524/408; 524/462
[58] Field of Search ............... 526/314; 524/401, 524/404, 408, 462, 174, 167; 560/225, 187

[56] References Cited

FOREIGN PATENT DOCUMENTS

| 56-92901 | 7/1981 | Japan | 526/314 |
| 192683 | 4/1989 | Japan | 526/314 |
| A5025353 | 2/1993 | Japan. | |
| A6223842 | 8/1994 | Japan. | |

OTHER PUBLICATIONS

Ans. 13 of 48 Kato et al, JP 95–20664 950208 In–House Computer Abstract pp. 22–23.
Ans. 16 of 48 Nakano et al JP94–115949–940502–In–House Computer Abstract pp. 25–26.
Ans. 29 of 48 Decker et al. Makromol. Chem., 192(3), 507–22 (English) 1991–In–House Computer Abstract pp. 41–42.
Ans. 41 of 48 Tokuyama Soda Co., JP81–205101–811221 In House Computer Abstract pp. 62–64.

*Primary Examiner*—Bernard Lipman
*Assistant Examiner*—N Sarofim
*Attorney, Agent, or Firm*—Birch, Stewart, Kolasch & Birch, LLP

[57] ABSTRACT

The novel acrylic ester, allyl ether and allyl carbonate of the present invention are characterized by having the structures represented by the following general formulae (I) to (IV):

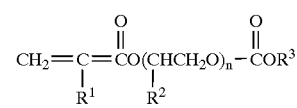

(I)

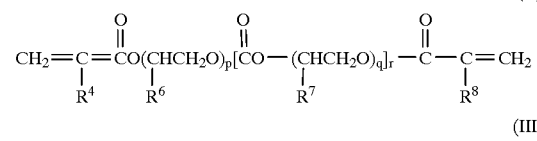

(II)

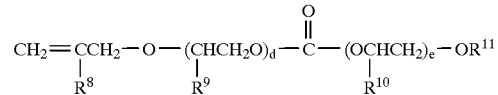

(III)

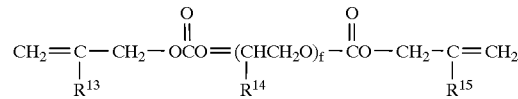

(IV)

The above acrylic ester, allyl ether and allyl carbonate are used as a starting monomer which forms a polymer matrix for use in a polymeric solid electrolyte. The novel polymer of the present invention comprises structural units derived from at least one compound selected from a group of the compounds represented by the above general formulae (I) to (IV). The polymeric solid electrolyte comprising the above novel polymer as a polymer matrix exhibits high ionic conductivity and is chemically stable.

18 Claims, 16 Drawing Sheets

ACRYLIC ESTER, NOVEL ALLYL ETHER, NOVEL ALLYL CARBONATE, ACRYLIC ESTER POLYMER, ALLYL ETHER POLYMER, ALLYL CARBONATE POLYMER AND POLYMERIC SOLID ELECTROLYTE

This application is a continuation-in-part of application Entitled: NOVEL ACRYLIC ETHER, NOVEL ALLYL ETHER, NOVEL ALLYL CARBONATE, ACRYLIC ESTER POLYMER, ALLYL ETHER POLYMER, ALLYL CARBONATE POLYMER AND POLYMERIC SOLID ELECTROLYTE Ser. No. 08/817,748 filed on Apr. 23, 1997, which claims priority of International Application No. PCT/JP96/02358, filed Aug. 23, 1996. The entire contents of both of these applications are hereby incorporated by references.

TECHNICAL FIELD

The present invention relates to novel polymers employed for purposes such as a polymer matrix of polymeric solid electrolyte and to a process for producing the same. The present invention also relates to a polymeric solid electrolyte for use in a primary battery, a secondary battery, a capacitor and the like.

BACKGROUND ART

It is common to employ a liquid electrolyte in an electrochemical element such as a primary battery, a secondary battery or a capacitor. However, the liquid electrolyte has drawbacks in that liquid leakage occurs and it cannot ensure long-term reliability.

The use of a solid electrolyte for overcoming the above drawbacks of the liquid electrolyte is known. The application of the solid electrolyte to the above electrochemical element enables not only providing an element which is free from liquid leakage and ensures high reliability but also realizing miniaturization and weight reduction of the element per se.

A variety of polymeric solid electrolytes have been studied for recent years. The polymeric solid electrolytes not only are so flexible that appropriate application can be made irrespective of a volume change which occurs during the ion/electron exchange reaction between the electrode and each polymeric solid electrolyte but also has the above-mentioned general advantages of the solid electrolytes.

The use of a complex composed of a polyethylene oxide having polyether structure and an alkali metal salt such as a lithium salt is known among such a variety of polymeric solid electrolytes.

Japanese Patent Laid-open Publication No. 25353/1993 describes a polymeric solid electrolyte composed mainly of a crosslinked resin comprising a copolymer of a polyoxyalkylene diester compound, a polymethoxyoxyalkylene ester compound and an oxy compound having double bond, and an inorganic salt. Further, Japanese Patent Laid-open Publication No. 223842/1994 describes a polymeric solid electrolyte composed of an organic polymer having a carbonate group as a functional group and a metal salt.

However, these solid electrolytes generally have lower ionic conductivity than those of the liquid electrolytes, so that it is difficult to obtain a primary or secondary battery having excellent discharge characteristics therefrom.

Under the circumstance, there are demands on the development of a polymeric solid electrolyte which can satisfy the requirements such as high ionic conductivity and high electrochemical stability, and the development of a novel polymer which can be a polymer matrix of the above polymeric solid electrolyte. Further, there are demands on the development of a novel compound which can be a starting monomer capable of forming the above polymer.

OBJECT OF THE INVENTION

The present invention has been made in view of the above state of prior art. Thus, an object of the present invention is to provide a novel acrylic ester, allyl ether and allyl carbonate which can be starting monomers suitable for forming desired polymers. Another object of the present invention is to provide an acrylic ester polymer, allyl ether polymer and allyl carbonate polymer which can be polymer matrixes suitable for use in polymeric solid electrolytes. A further object of the present invention is to provide a polymeric solid electrolyte which exhibits high ionic conductivity and is chemically stable.

DISCLOSURE OF THE INVENTION

The first novel acrylic ester of the present invention is represented by the general formula (I):

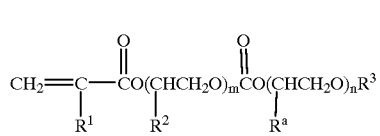

wherein $R^1$, $R^2$ and $R^a$ may be identical with or different from each other and each represents hydrogen atom or an alkyl group having 1 to 4 carbon atoms; $R^3$ represents an alkyl group having 1 to 4 carbon atoms; m is an integer of 1 to 100, and n is an integer of 0 to 100.

The second novel acrylic ester of the present invention is represented by the general formula (II):

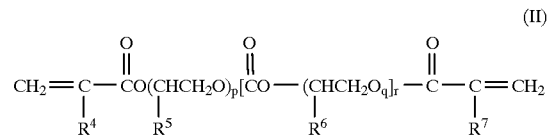

wherein $R^4$ to $R^7$ may be identical with or different from each other and each represents hydrogen atom or an alkyl group having 1 to 4 carbon atoms; and p, q and r may be identical with or different from each other and each is an integer of 1 to 100.

The novel allyl ether of the present invention is represented by the general formula (III):

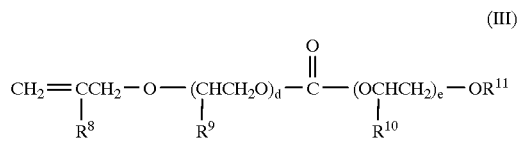

wherein $R^8$, $R^9$ and $R^{10}$ may be identical with or different from each other and each represents hydrogen atom or an alkyl group having 1 to 4 carbon atoms; $R^{11}$ represents an alkyl group having 1 to 4 carbon atoms or $CH_2CR^{12}=CH_2$ in which $R^{12}$ represents hydrogen atom or a methyl group; d is an integer of 0 to 100; and e is an integer of 0 to 100.

The novel allyl carbonate of the present invention is represented by the general formula (IV):

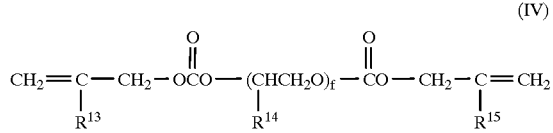

(IV)

wherein $R^{13}$, $R^{14}$ and $R^{15}$ may be identical with or different from each other and each represents hydrogen atom or an alkyl group having 1 to 4 carbon atoms; and f is an integer of 1 to 100.

The first acrylic ester polymer of the present invention comprises structural units derived from at least one acrylic ester selected from a group of the acrylic esters represented by the above general formula (I).

Examples of the above first acrylic ester polymers include a homopolymer or copolymer of an acrylic ester selected from the group of the acrylic esters represented by the above general formula (I) and a copolymer of at least one acrylic ester selected from the group of the acrylic esters represented by the above general formula (I) and at least one compound selected from the group of the compounds represented by the above general formula (II) and the following general formulae (V) to (VIII):

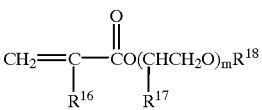

(V)

wherein $R^{16}$ and $R^{17}$ may be identical with or different from each other and each represents hydrogen atom or an alkyl group having 1 to 4 carbon atoms; $R^{18}$ represents an alkyl group having 1 to 4 carbon atoms; and m is an integer of 0 to 100,

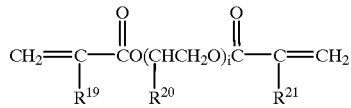

(VI)

wherein $R^{19}$, $R^{20}$ and $R^{21}$ may be identical with or different from each other and each represents hydrogen atom or an alkyl group having 1 to 4 carbon atoms; and i is an integer of 1 to 100,

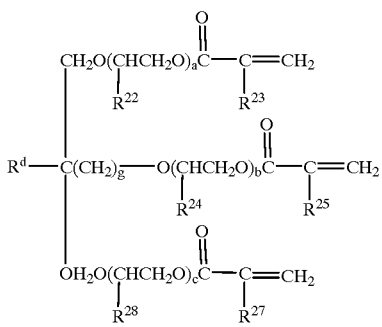

(VII)

wherein $R^{22}$ to $R^{27}$ may be identical with or different from each other and each represents hydrogen atom or an alkyl group having 1 to 4 carbon atoms; a, b and c may be identical with or different from each other and each are an integer of 0 to 100, and where $R^d$ being H, g is zero, or where $R^d$ being $CH_2CH_3$, g is 1, and

HO—$(CH_2CH_2O)_k$—H    (VIII)

wherein k is an integer of 1 to 100.

The second acrylic ester polymer of the present invention comprises structural units derived from at least one acrylic ester selected from a group of the acrylic esters represented by the above general formula (II).

Examples of the above second acrylic ester polymers include a homopolymer or copolymer of an acrylic ester selected from the group of the acrylic esters represented by the above general formula (II) and a copolymer of at least one acrylic ester selected from the group of the acrylic esters represented by the above general formula (II) and at least one compound selected from a group of the compounds represented by the above general formulae (V) to (VIII).

The allyl ether polymer of the present invention comprises structural units derived from at least one allyl ether selected from a group of the allyl ethers represented by the above general formula (III).

Examples of the above allyl ether polymers include a homopolymer or copolymer of an allyl ether selected from the group of the allyl ethers represented by the above general formula (III) and a copolymer of at least one allyl ether selected from the group of the allyl ethers of represented by the above general formula (III) and at least one compound selected from a group of the compounds represented by the above general formulae (IV) and (VII) and the following general formula (IX) and (X):

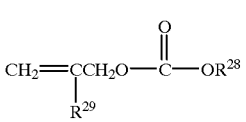

(IX)

wherein $R^{28}$ represents an alkyl group having 1 to 4 carbon atoms; $R^{29}$ represents hydrogen atom or an alkyl group having 1 to 4 carbon atoms; and

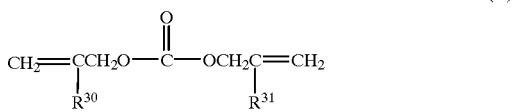

(X)

wherein each of $R^{30}$ and $R^{31}$ represents hydrogen atom or an alkyl group having 1 to 4 carbon atoms.

The first allyl carbonate polymer of the present invention comprises structural units derived from at least one allyl carbonate selected from a group of the allyl carbonates represented by the above general formula (IV).

Examples of the above first allyl carbonate polymers include a homopolymer or copolymer of an allyl carbonate selected from a group of the allyl carbonates represented by the above general formula (IV) and a copolymer of at least one allyl carbonate selected from the group of the allyl carbonates represented by the above general formula (IV) and at least one compound selected from a group of the compounds represented by the above general formula (VII), (IX) and (X).

The second allyl carbonate polymer of the present invention comprises:

structural units derived from at least one compound selected from the group of the compounds represented by the above general formula (VII) and structural units derived from at least one compound selected from a group of the compounds represented by the above general formula (IX).

The third allyl carbonate polymer of the present invention comprises:

structural units derived from at least one compound selected from the group of the compounds represented by the above general formula (VII) and structural units derived from at least one compound selected from a group of the compounds represented by the above general formula (X).

The polymeric solid electrolyte of the present invention comprises at least one member of the above acrylic ester polymers, allyl ether polymers and allyl carbonate polymers and a salt of a metal of Group Ia of the periodic table.

The polymeric solid electrolyte of the present invention comprises at least one member of the above acrylic ester polymers, allyl ether polymers and allyl carbonate polymers, a salt of a metal of Group Ia of the periodic table and a nonaqueous solvent.

BEST MODE FOR CARRYING OUT THE INVENTION

Figure 1:
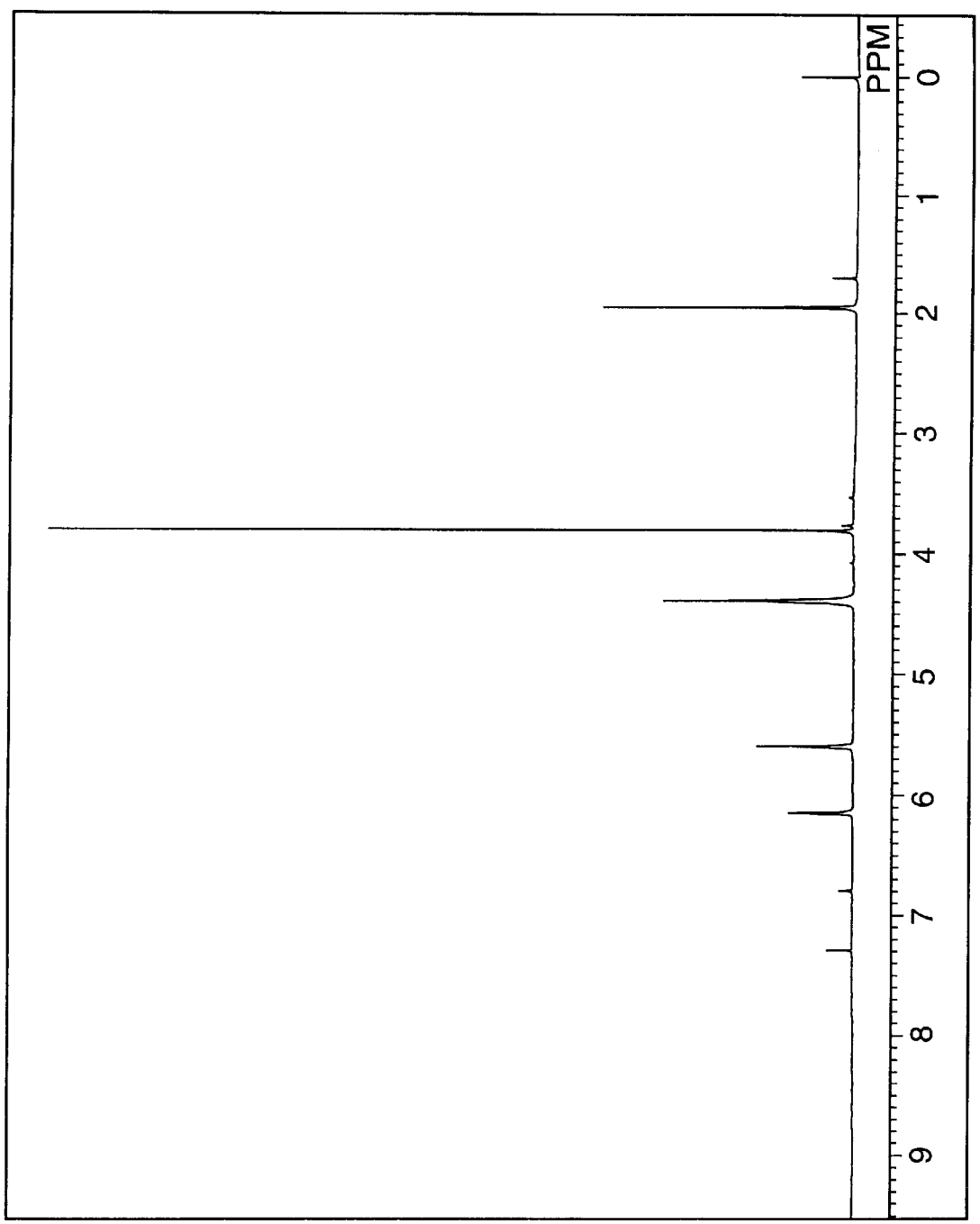
FIG. 1 is an NMR spectrum of methacrylic acid-2-hydroxyethyl methylcarbonate (2-methacryloyloxyethyl methyl carbonate) obtained in Example 1.

The novel acrylic ester, novel allyl ether, novel allyl carbonate, acrylic ester polymer, allyl ether polymer, allyl carbonate polymer and polymeric solid electrolyte according to the present invention will be described in detail below.

Herein, the meaning of the term "polymerization" is not limited to homopolymerization and may comprehend copolymerization. Likewise, the meaning of the term "polymer" is not limited to a homopolymer and may comprehend a copolymer.

Novel Acrylic Ester

First, the novel acrylic ester of the present invention will be described as follows.

First Acrylic Ester

The first novel acrylic ester of the present invention is represented by the general formula (I):

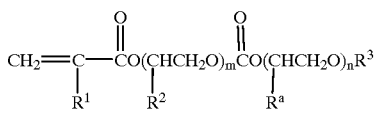

(I)

In the above formula, $R^1$, $R^2$ and $R^a$ may be identical with or different from each other and each represents hydrogen atom or an alkyl group having 1 to 4 carbon atoms, preferably, hydrogen atom or methyl group.

$R^3$ represents an alkyl group having 1 to 4 carbon atoms, preferably, methyl group, ethyl group or t-butyl group.

m is an integer of 1 to 100.

n is an integer of 0 to 100.

(m+n) is preferably not more than 50.

Examples of the acrylic esters represented by the above general formula (I) include methacrylic acid-2-hydroxyethyl methylcarbonate (2-methacryloyloxyethyl methyl carbonate), 2-(methacrylic acid-2-hydroxyethoxy)ethyl methylcarbonate (2(2-methacryloyloxyethoxy)etyl methyl carbonate), 2-hydroxy-methacrylic acid-ethyl ethylcarbonate (2-methacryloyloxyethyl ethyl carbonate), 2-hydroxyacrylethyl methylcarbonate (2-acryloyloxyethyl methyl carbonate) and 2-(acryl-2-hydroxyethoxy)ethyl methylcarbonate (2(2-acryloyloxyethoxy)ethyl methyl carbonate).

The acrylic ester represented by the above general formula (I) can be synthesized by, for example, reacting the compound of the general formula (i) given below with the compound of the general formula (ii) given below in the following manner:

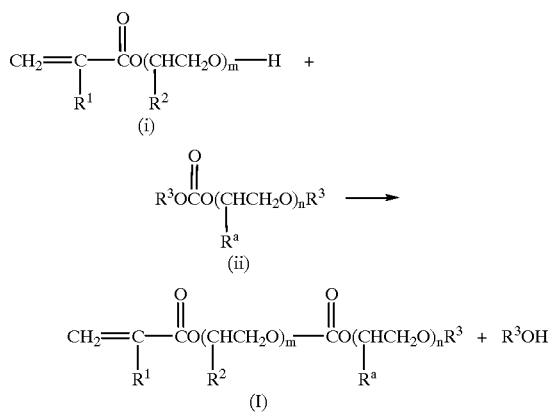

wherein $R^1$, $R^2$, $R^3$, $R^a$, m and n have the same meaning as defined with respect to the general formula (I).

In the above synthetic process, the compound represented by the general formula (ii) is used in an amount of 0.5 to 5 mol based on 1 mol of the compound represented by the general formula (i). This reaction can be performed in the presence of a catalyst such as $K_2CO_3$, $Na_2CO_3$, $Li_2CO_3$ or $NaOCH_3$. This catalyst is used in an amount of $1\times10^{-5}$ to $1\times10^{-2}$ mol based on 1 mol of the compound represented by the general formula (i). To the reaction system, a polymerization inhibitor such as hydroquinone may be added.

The reaction between the compound represented by the general formula (i) and the compound represented by the general formula (ii) is generally conducted under reflux and, if desired, under reduced pressure under agitation with removing formed alcohol. The reaction temperature generally ranges from 40 to 140° C. and the reaction time generally ranges from 2 to 60 hrs.

Second Acrylic Ester

The second acrylic ester of the present invention is represented by the general formula (II):

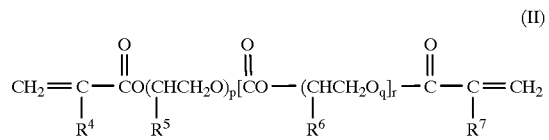

(II)

In the above general formula, $R^4$ to $R^7$ may be identical with or different from each other and each represents hydrogen atom or an alkyl group having 1 to 4 carbon atoms, preferably hydrogen atom or methyl group. p, q and r may be identical with or different from each other and each is an integer of 1 to 100, (p+q×r) is preferably not more than 50.

Examples of the acrylic esters represented by the above general formula (II) include di(2-methacryloxyethyl) carbonate (di(2-methacryloyloxyethyl) carbonate), di(2-acryloxyethyl) carbonate, ethylene glycol di(2-methacryloxyethyl) carbonate (di[2(2-methacryloyloxyethoxy)ethyl] carbonate), di(2-methacryloxy-2-methylethyl) carbonate (di(2-methacryloyloxy-2-methylethyl)carbonate) and diethylene glycol di(2-methacryloxyethyl) carbonate di{2[2(2-methacryloyloxy)ethoxy]ethyl} carbonate.

The compound represented by the above general formula (II) can be synthesized by, for example, reacting the compound of the general formula (iii) given below with the compound of the general formula (iv) given below in the following manner:

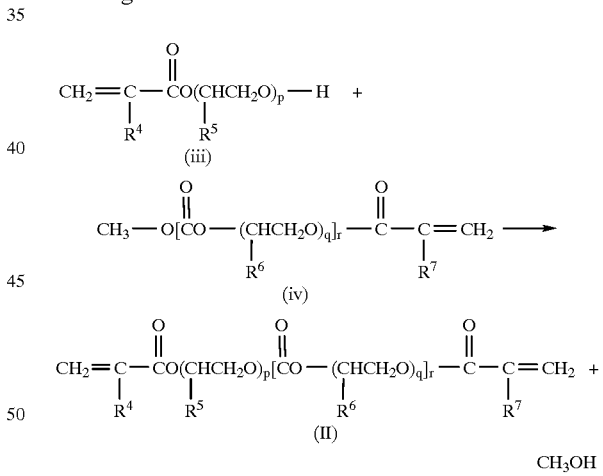

$CH_3OH$ wherein $R^4$, $R^5$, $R^6$, $R^7$, p, q and r have the same meaning as defined with respect to the general formula (II).

In the above synthetic process, the compound represented by the general formula (iv) is used in an amount of 0.3 to 2.0 mol based on 1 mol of the compound represented by the general formula (iii). This reaction can be performed in the presence of a catalyst such as $K_2CO_3$, $Ka_2CO_3$, $Li_2CO_3$ or $NaOCH_3$. This catalyst is used in an amount of $10^{-5}$ to $10^{-2}$ mol based on 1 mol of the compound represented by the general formula (iii). To the reaction system, a polymerization inhibitor such as hydroquinone may be added.

The reaction between the compound represented by the general formula (iii) and the compound represented by the general formula (iv) is generally conducted under reflux and, if desired, under reduced pressure under agitation with removing formed alcohol. The reaction temperature generally ranges from 40 to 140° C., preferably 40 to 100° C. and the reaction time generally ranges from 2 to 60 hrs.

The compound represented by the above general formula (II) can also be synthesized by the step (i) to (iii):

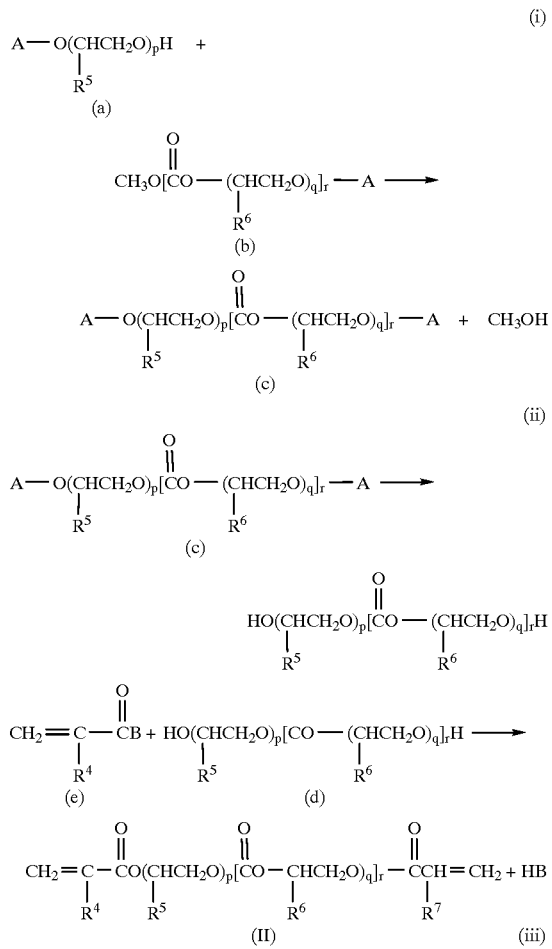

The group A is a general protective group. Examples of such groups include a tetrahydropyranyl group, a benzyl group, a t-butyl group, a t-butylcarbonyl group and a tetramethylsilyl group. The group B is a hydroxyl group or halogen.

In the step (i), a compound represented by the formula (c) is synthesized from a compound represented by the formula (a) and a compound represented by the formula (b).

The compound of the formula (a) and the compound of the formula (b) are used in a molar ratio (compound of the formula (a)/compound of the formula (b)) of 0.1 to 10.0. In the above reaction, basic catalysts, such as $K_2CO_3$, $Na_2CO_3$, $Li_2CO_3$ and $NaOCH_3$, can be employed. Such catalyst is used in an amount of $10^{-5}$ to $10^{-2}$ mol based on 1 mol of the compound represented by the formula (a).

The reaction of the compound represented by the formula (a) with the compound represented by the formula (b) is carried out by heating them generally with stirring and if desired under reduced pressure, while methyl alcohol produced is removed out of the reaction system. The reaction temperature is usually 40 to 170° C., preferably 65 to 100° C., and the reaction time is usually 2 to 60 hours.

In the step (ii), a reaction of removing the protective group from the obtained compound of the formula (c) is carried out, to synthesize a compound represented by the formula (d).

The reaction of removing the protective group is conducted under the usual conditions in accordance with the type of the protective group. For example, when the protective group is a benzyl group, 5 to 30% by weight of Pd/C is added to the compound represented by the formula (c), and they are reacted at room temperature for usually 2 to 24 hours in an atmosphere of hydrogen with stirring, whereby the compound represented by the formula (d) is obtained.

In the step (iii), a compound represented by the formula (II) is synthesized from the obtained compound represented by the formula (d) and a compound represented by the formula (e).

The compound of the formula (d) and the compound of the formula (e) are used in a molar ratio (compound of the formula (d)/compound of the formula (e)) of 1.0 to 2.0.

When the group B is a hydroxyl group, the compound represented by the formula (II) is obtained by reacting the above compounds at 60 to 150° C. in the presence of an esterification catalyst (e.g., sulfuric acid, p-toluenesulfonic acid) and a polymerization inhibitor such as hydroquinone.

When the group B is halogen, the compound represented by the formula (II) is obtained by reacting the above compounds at −20 to 80° C., preferably 0 to 40° C., for 30 minutes to several hours in an atmosphere of a dry inert gas in the presence of a nitrogen-containing organic base, such as triethylamine, pyridine or N,N-dimethylaniline. To the reaction system, a polymerization inhibitor such as hydroquinone may be added.

The first and second acrylic esters of the present invention can be used as, for example, starting monomers for use in the production of an acrylic ester polymer. The polymeric solid electrolyte comprising, as a polymer matrix, the acrylic ester polymer having structural units derived from each of the first and second acrylic esters of the present invention exhibits high ionic conductivity and is chemically stable.

Novel Allyl Ether

The novel allyl ether of the present invention is represented by the general formula (III):

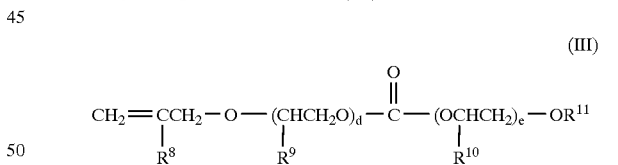

wherein $R^8$, $R^9$ and $R^{10}$ may be identical with or different from each other and each represents hydrogen atom or an alkyl group having 1 to 4 carbon atoms; $R^{11}$ represents an alkyl group having 1 to 4 carbon atoms or $CH_2CR^{12}=CH_2$ in which $R^{12}$ represents hydrogen atom or methyl group; d is an integer of 0 to 100; and e is an integer of 0 to 100. (d+e) is preferably not more than 50.

Examples of the above allyl ethers include 2-methoxyethyl allyl carbonate, 2-methoxypropyl allyl carbonate (2-methoxy-2-methylethyl allyl carbonate), 2-ethoxyethyl allyl carbonate, 2-methoxyethyl methallyl carbonate, 2-(2-methoxyethoxy)ethyl allyl carbonate, di(2-allyloxyethyl) carbonate, di[2-(2-allyloxyethoxy)ethyl] carbonate and 2-(2-allyloxyethoxy)ethyl 2-allyloxyethyl carbonate.

The allyl ether represented by the above general formula (III) can be synthesized from, for example, the compounds of the general formulae (v) to (vii) given below in the following manner:

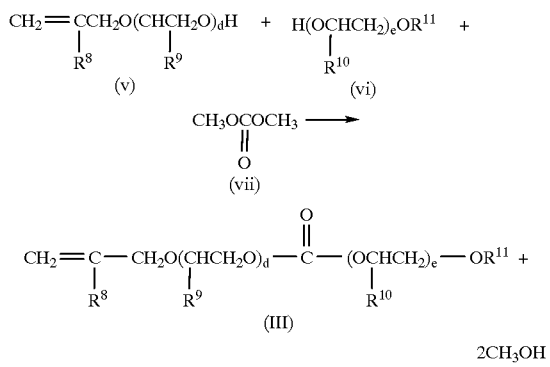

wherein $R^8$, $R^9$, $R^{10}$, $R^{11}$, d and e have the same meaning as defined with respect to the general formula (III).

In the above synthesis using the compounds (v), (vi) and (vii), each of the compounds represented by the general formulae (v) and (vi) is used in an amount of 0.2 to 1.0 mol based on 1 mol of dimethyl carbonate (vii). This reaction can be performed in the presence of a catalyst such as $LiOCH_3$, $Li_2CO_3$, $K_2CO_3$ or $Na_2CO_3$. This catalyst is used in an amount of $1\times10^{-5}$ to $1\times10^{-2}$ mol based on 1 mol of the compound represented by the general formula (v). To the reaction system, a polymerization inhibitor such as hydroquinone may be added.

The above synthesis is generally conducted under reflux and, if desired, under reduced pressure under agitation with removing formed alcohol. The reaction temperature generally ranges from 40 to 140° C., and the reaction time generally ranges from 2 to 60 hr.

Further, the allyl ether represented by the above general formula (III) can be synthesized from the compound represented by the above general formula (vi) and the compound represented by the general formula (viii) given below in the following manner:

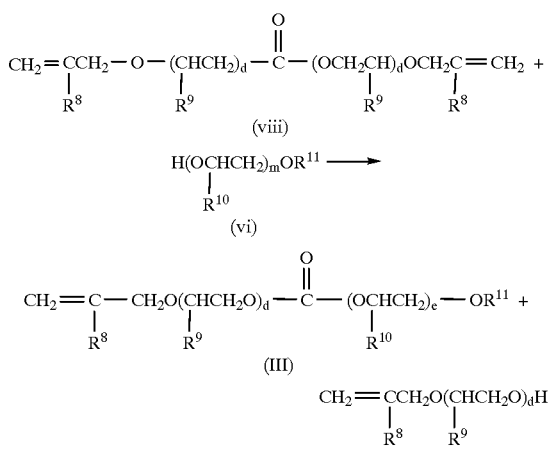

wherein $R^8$, $R^9$, $R^{10}$, $R^{11}$, e and d have the same meaning as defined with respect to the general formula (III).

In the above synthesis using the compounds (viii) and (vi), the compound represented by the general formula (vi) is used in an amount of 0.5 to 2.0 mol based on 1 mol of the compound represented by the general formula (viii). This reaction can be performed in the presence of a catalyst such as $LiOCH_3$, $Li_2CO_3$, $K_2CO_3$ or $Na_2CO_3$. This catalyst is preferably used in an amount of $1\times10^{-5}$ to $1\times10^{-2}$ mol based on 1 mol of the compound represented by the general formula (viii). To the reaction system, a polymerization inhibitor such as hydroquinone may be added. The reaction is generally conducted under reflux and, if desired, under reduced pressure under agitation. The reaction temperature generally ranges from 40 to 140° C. and the reaction time generally ranges from 2 to 60 hr.

Still further, the allyl ether represented by the above general formula (III) can be synthesized from the compound represented by the above general formula (v) and the compound represented by the general formula (ix) given below in the following manner:

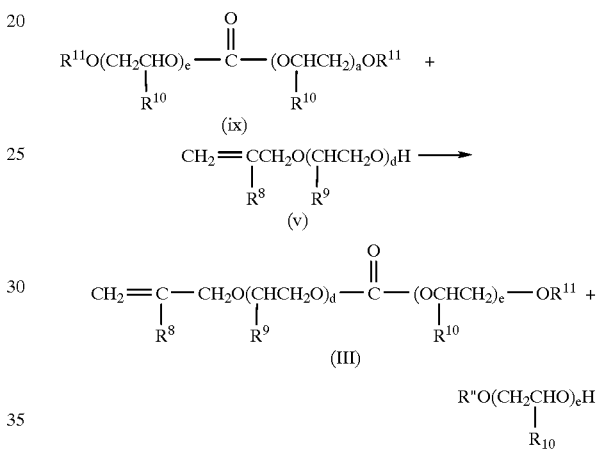

wherein $R^8$, $R^9$, $R^{10}$, $R^{11}$, d and e have the same meaning as defined with respect to the general formula (III).

In the above synthesis using the compounds (v) and (ix), the compound represented by the general formula (ix) is used in an amount of 0.5 to 2.0 mol based on 1 mol of the compound represented by the general formula (v). This reaction can be performed in the presence of a catalyst such as $LiOCH_3$, $Li_2CO_3$, $K_2CO_3$ or $Na_2CO_3$. This catalyst is used in an amount of $1\times10^{-5}$ to $1\times10^{-2}$ mol based on 1 mol of the compound represented by the general formula (v). To the reaction system, a polymerization inhibitor such as hydroquinone may be added. The reaction is generally conducted under reflux and, if desired, under reduced pressure under agitation. The reaction temperature generally ranges from 40 to 140° C., and the reaction time generally ranges from 2 to 60 hr.

The allyl ether of the present invention can be used as, for example, a starting monomer for use in the production of an allyl ether polymer. The polymeric solid electrolyte comprising, as a polymer matrix, the allyl ether polymer having structural units derived from the allyl ether of the present invention exhibits high ionic conductivity and is chemically stable.

Novel Allyl Carbonate

The novel allyl carbonate of the present invention is represented by the general formula (IV):

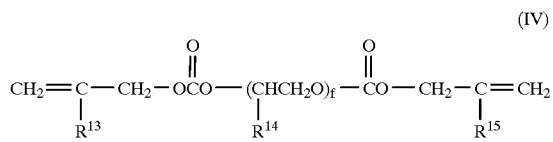

(IV)

wherein $R^{13}$, $R^{14}$ and $R^{15}$ may be identical with or different from each other and each represents hydrogen atom or an alkyl group having 1 to 4 carbon atoms; and f is an integer of 1 to 100, preferably 1 to 50.

Examples of the above allyl carbonates include ethylene glycol diallyl dicarbonate, diethylene glycol diallyl dicarbonate, diethylene glycol dimethallyl dicarbonate and triethylene glycol diallyl dicarbonate.

The allyl carbonate represented by the above general formula (IV) can be synthesized from, for example, the compound represented by the general formula (x) given below and the compound represented by the general formula (xi) given below in the following manner:

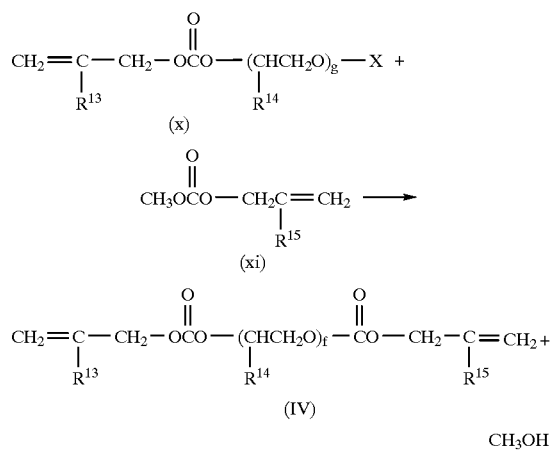

wherein $R^{13}$ to $R^{15}$ and f have the same meaning as defined with respect to the general formula (IV).

In the above synthetic process, the compound represented by the general formula (xi) is used in an amount of 0.3 to 2.0 mol based on 1 mol of the compound represented by the general formula (x). This reaction can be performed in the presence of a catalyst such as $K_2CO_3$, $Na_2CO_3$, $Li_2CO_3$ or $NaOCH_3$. This catalyst is used in an amount of $1\times10^{-5}$ to $1\times10^{-2}$ mol based on 1 mol of the compound represented by the general formula (x). To the reaction system, a polymerization inhibitor such as hydroquinone may be added.

The reaction between the compound represented by the general formula (x) and the compound represented by the general formula (xi) is generally conducted under reflux and, if desired, under reduced pressure under agitation with removing formed alcohol. The reaction temperature general ranges from 40 to 140° C. and the reaction time generally ranges from 2 to 60 hr.

The allyl carbonate of the present invention can be used as, for example, a starting monomer for use in the production of an allyl carbonate polymer. The polymeric solid electrolyte comprising, as a polymer matrix, the allyl carbonate polymer having structural units derived from the allyl carbonate of the present invention exhibits high ionic conductivity and is chemically stable.

Acrylic Ester Polymer

First acrylic ester polymer

The first acrylic ester polymer of the present invention comprises structural units derived from at least one acrylic ester selected from the group of the acrylic esters represented by the above general formula (I).

Examples of such polymers include a homopolymer of an acrylic ester selected from among the acrylic esters represented by the above general formula (I), a copolymer of at least two acrylic esters selected from the group of the acrylic esters represented by the above general formula (I) and a copolymer of at least one acrylic ester selected from the group of the acrylic esters represented by the above general formula (I) and at least one compound selected from the group of the compounds represented by the above general formula (II) and the general formula (V) to (VIII) given below.

First, the compound represented by the general formula (V) will be described.

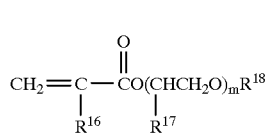

(V)

wherein $R^{16}$ and $R^{17}$ may be identical with each other or different from each other and each represents hydrogen atom or an alkyl group having 1 to 4 carbon atoms, preferably hydrogen atom or methyl group.

$R^{18}$ represents an alkyl group having 1 to 4 carbon atoms, preferably methyl group.

m is an integer of 0 to 100, preferably, 0 to 30.

Examples of the compounds represented by the above general formula (V) include methyl acrylate, ethyl acrylate, methyl methacrylate, ethyl methacrylate.

Next, the compound represented by the general formula (VI) will be described.

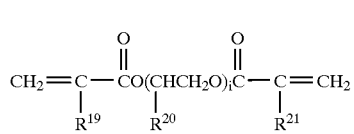

(VI)

wherein $R^{19}$, $R^{20}$ and $R^{21}$ may be identical with or different from each other and each represent a hydrogen atom or an alkyl group having 1 to 4 carbon atoms, preferably hydrogen atom or methyl group, and i is an integer of 1 to 100, preferably 1 to 50.

Examples of the compounds represented by the above general formula (VI) include diethylene glycol dimethylacrylate, ethylene glycol dimethacrylate, diethylene glycol diacrylate, diisopropylene glycol dimethacrylate and triethylene glycol dimethacrylate.

Now, the compound represented by the general formula (VII) will be described.

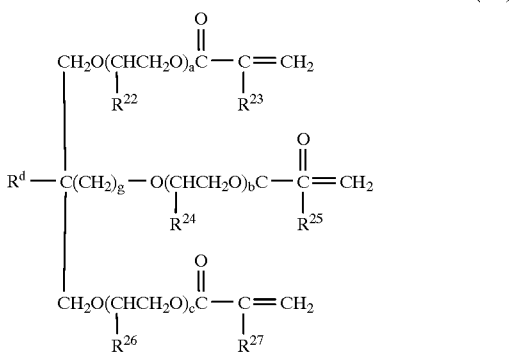

(VII)

wherein $R^{22}$ to $R^{27}$ may be identical with or different from each other and each represents hydrogen atom or an alkyl group having 1 to 4 carbon atoms, preferably hydrogen atom or methyl group, and a, b and c may be identical with or different from each other and each is an integer of 0 to 100, preferably 0 to 50, and where $R^d$ is H, g is zero, or where $R^d$ is $CH_2CH_3$, g is 1.

Examples of the compounds represented by the above general formula (VII) include glycerol trimethacrylate, glycerol triacrylate, tri(2-methacryloxyethyl)glycerol and tri(2-acryloxyethyl)glycerol.

Finally, the compound represented by the general formula (VIII) will be described. The compound represented by the general formula (VIII) is polyethylene oxide.

(VIII)

wherein k is an integer of 1 to 100, preferably 1 to 20.

The polymer of at least one acrylic ester selected from the group of the acrylic esters represented by the above general formula (I) which is a preferred embodiment of the present invention generally has a molecular weight ranging from $2 \times 10^3$ to $1 \times 10^8$, preferably from $1 \times 10^4$ to $1 \times 10^7$.

Although the proportion of structural units derived from two or more acrylic esters is not particularly limited in the copolymer of at least two acrylic esters selected from the group of the acrylic esters represented by the above general formula (I), it is preferred that the ratio of structural units derived from one acrylic ester range from 40 to 95 mol %.

The copolymer of an acrylic ester selected from the group of the acrylic esters represented by the above general formula (I) and at least one compound selected from the group of the compounds represented by the above general formula (II) and general formulae (V) to (VIII), which is another preferred embodiment of the present invention, generally has a molecular weight ranging from $2 \times 10^3$ to $1 \times 10^8$, preferably from $1 \times 10^4$ to $1 \times 10^7$. The molar ratio of structural units derived from the acrylic ester of the above general formula (I) to structural units derived from the compound selected from the group of the compounds of the above general formulas (II) and (V) to (VIII) generally ranges from 5:95 to 100:0, preferably from 5:95 to 95:5 and, still preferably from 10:90 to 90:10.

The molar ratio of structural units derived from the acrylic ester of the above general formula (I) to structural units derived from the compound selected from the group of the compounds of the above general formulae (II) and (V) to (VIII) is regulated within the above range in conformity with the desired physical and chemical properties of the copolymer.

When the molar ratio of structural units derived from the acrylic ester of the above general formula (I) to structural units derived from the compound selected from the group of the compounds of the above general formulae (II) and (V) to (VIII) falls outside the above range, problems may be encountered such that the ionic conductivity is lowered, and a viscosity and elasticity of the polymer are lowered, and the tensile strength is poor.

The first acrylic ester polymer of the present invention can be produced by customary methods. For example, it can easily be produced by polymerizing either at least one member selected from the group of the acrylic esters represented by the above general formula (I) or at least one member selected from the group of the acrylic esters represented by the above general formula (I) together with at least one compound selected from the group of the compounds represented by the above general formulae (II) and (V) to (VIII) according to the radical polymerization or photopolymerization technique.

The first acrylic ester polymer of the present invention may contain structural units other than the structural units derived from the monomers represented by the above general formulae (I), (II) and (V) to (VIII) in an amount of, for example, up to 20 mol %.

Second acrylic ester polymer

The second acrylic ester polymer of the present invention comprises structural units derived from at least one acrylic ester selected from the group of the acrylic esters represented by the above general formula (II).

Examples of such polymers include a homopolymer of an acrylic ester selected from the group of the acrylic esters represented by the above general formula (II), a copolymer of at least two acrylic esters selected from the group of the acrylic esters represented by the above general formula (II) and a copolymer of at least one acrylic ester selected from the group of the acrylic esters represented by the above general formula (II) and at least one compound selected from the group of the compounds represented by the above general formulae (V) to (VIII).

The polymer of at least one acrylic ester selected from the group of the acrylic esters represented by the above general formula (II) which is one of preferred embodiments of the present invention generally has a molecular weight ranging from $2 \times 10^3$ to $1 \times 10^8$, preferably from $1 \times 10^4$ to $1 \times 10^7$.

Although the proportion of structural units derived from two or more acrylic esters is not particularly limited in the copolymer of at least two acrylic esters selected from the group of the acrylic esters represented by the above general formula (II), it is preferred that the ratio of structural units derived from one acrylic ester range from 40 to 95 mol %.

The copolymer of an acrylic ester selected from the group of the acrylic esters represented by the above general formula (II) and at least one compound selected from the group of the compounds represented by the above general formulae (V) to (VIII), which is another preferred embodiment of the present invention, generally has a molecular weight ranging from $2 \times 10^3$ to $1 \times 10^8$, preferably from $1 \times 10^4$ to $1 \times 10^7$. The molar ratio of structural units derived from the acrylic ester of the above general formula (II) to structural units derived from the compound selected from the group of the compounds of the above general formulae (V) to (VIII) generally ranges from 5:95 to 100:0, preferably from 5:95 to 95:5 and, still preferably from 10:90 to 90:10.

The molar ratio of structural units derived from the acrylic ester of the above general formula (II) to structural units derived from the compound selected from the group of the compounds of the above general formulae (V) to (VIII) is regulated within the above range in conformity with the desired physical and chemical properties of the copolymer.

When the molar ratio of structural units derived from the acrylic ester of the above general formula (II) to structural units derived from the compound selected from the group of the compounds of the above general formulae (V) to (VIII) falls outside the above range, problems may be encountered such that the ionic conductivity is lowered, and a viscosity and elasticity of the polymer are lowered, and the tensile strength is poor.

The second acrylic ester polymer of the present invention can be produced by customary methods. For example, it can easily be produced by polymerizing either at least one member selected from the group of the acrylic esters represented by the above general formula (II) or at least one member selected from the group of the acrylic esters represented by the above general formula (II) together with at least one compound selected from the group of the compounds represented by the above general formulae (V) to (VIII) according to the radical polymerization or photopolymerization technique.

The second acrylic ester polymer of the present invention may contain structural units other than the structural units derived from the monomers represented by the above general formulae (II) and (V) to (VIII) in an amount of, for example, up to 20 mol %.

Allyl Ether Polymer

The allyl ether polymer of the present invention comprises structural units derived from at least one allyl ether selected from the group of the allyl ethers represented by the above general formula (III).

Examples of the above allyl ether polymers include a homopolymer of an allyl ether selected from the group of the allyl ethers represented by the above general formula (III), a copolymer of at least two allyl ethers selected from the group of the allyl ethers represented by the above general formula (III) and a copolymer of at least one allyl ether selected from the group of the allyl ethers of represented by the above general formula (III) and at least one compound selected from the group of the compounds represented by the above general formulae (IV) and (VII) and the following general formulae (IX) and (X).

First, the compound represented by the general formula (IX) will be described.

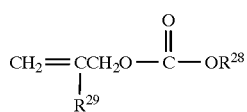
(IX)

wherein $R^{28}$ represents an alkyl group having 1 to 4 carbon atoms; and $R^{29}$ represents hydrogen atom or an alkyl group having 1 to 4 carbon atoms.

Examples of the above compounds represented by the general formula (IX) include methyl allyl carbonate, ethyl allyl carbonate, methyl methallyl carbonate, methyl ethallyl carbonate, propyl allyl carbonate and butyl allyl carbonate.

The compound represented by the general formula (X) is as follows:

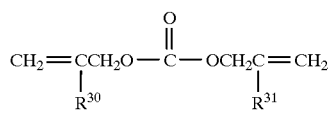
(X)

wherein each of $R^{30}$ and $R^{31}$ represents a hydrogen atom or an alkyl group having 1 to 4 carbon atoms. Examples of the above compounds represented the general formula (IX) include diallyl carbonate, dimethallyl carbonate, diethallyl carbonate, allyl methallyl carbonate and allyl ethallyl carbonate.

The polymer of at least one allyl ether selected from the group of the allyl ethers represented by the above general formula (III) which is one of preferred embodiments of the present invention generally has a molecular weight ranging from $1 \times 10^3$ to $1 \times 10^7$, preferably from $1 \times 10^4$ to $1 \times 10^6$.

Although the proportion of structural units derived from two or more allyl ethers is not particularly limited in the copolymer of at least two allyl ethers selected from the group of the allyl ethers represented by the above general formula (III), it is preferred that the ratio of structural units derived from one allyl ether ranges from 30 to 95 mol %.

The copolymer of at least one allyl ether selected from the group of the allyl ethers represented by the above general formula (III) and at least one compound selected from the group of the compounds represented by the above general formulae (IV), (VII), (IX) and (X), which is another preferred embodiment of the present invention, generally has a molecular weight ranging from $1 \times 10^3$ to $1 \times 10^7$, preferably from $1 \times 10^4$ to $1 \times 10^6$. The molar ratio of structural units derived from the allyl ether of the above general formula (III) to structural units derived from the compound selected from the group of those of the above general formulae (IV), (VII), (IX) and (X) generally ranges from 5:95 to 95:5, preferably from 10:90 to 90:10.

The molar ratio of structural units derived from the allyl ether of the above general formula (III) to structural units derived from the compound selected from the group of those of the above general formulae (IV), (VII), (IX) and (X) is regulated within the above range in conformity with the desired physical and chemical properties of the copolymer.

When the molar ratio of structural units derived from the allyl ether of the above general formula (III) to structural units derived from the compound selected from the group of the compounds of the above general formulae (IV), (VII), (IX) and (X) falls outside the above range, problems may be encountered such that the ionic conductivity is lowered, and a viscosity and elasticity of the polymer are lowered, and the tensile strength is poor.

The above allyl ether polymer can be produced by customary methods. For example, it can easily be produced by polymerizing either at least one member selected from the group of the allyl ethers represented by the above general formula (III) or at least one member selected from the group of the allyl ethers represented by the above general formula (III) together with at least one compound selected from the group of the compounds represented by the above general formulae (IV), (VII), (IX) and (X) according to the radical polymerization or photopolymerization technique.

The allyl ether polymer of the present invention may contain structural units other than the structural units derived from the monomers represented by the above general formulae (III), (IV), (VII), (IX) and (X) in an amount of, for example, up to 20 mol %.

Allyl Carbonate Polymer

First allyl carbonate polymer

The first ally carbonate polymer of the present invention comprises structural units derived from at least one allyl carbonate selected from the group of the allyl carbonates represented by the above general formula (IV).

Examples of such polymers include a homopolymer of an allyl carbonate selected from the group of the allyl carbonates represented by the above general formula (IV), a copolymer of at least two allyl carbonates selected from the group of the allyl carbonates represented by the above general formula (IV) and a copolymer of at least one allyl carbonate selected from the group of the allyl carbonates represented by the above general formula (IV) and at least one compound selected from the group of the compounds represented by the above general formula (VII), (IX) and (X).

The polymer of at least one allyl carbonate selected from the group of the allyl carbonates represented by the above general formula (IV) which is one of preferred embodiments of the present invention generally has a molecular weight ranging from $1\times10^3$ to $1\times10^7$, preferably from $1\times10^4$ to $1\times10^6$.

Although the proportion of structural units derived from two or more allyl carbonates is not particularly limited in the copolymer of at least two allyl carbonates selected from the group of the allyl carbonates represented by the above general formula (IV), it is preferred that the ratio of structural units derived from one allyl carbonate ranges from 30 to 95 mol %.

The copolymer of at least one allyl carbonate selected from the group of the allyl carbonates represented by the above general formula (IV) and at least one compound selected from the group of the compounds represented by the above general formula (VII), (IX) and (X), which is another preferred embodiment of the present invention, generally has a molecular weight ranging from $1\times10^3$ to $1\times10^7$, preferably from $1\times10^4$ to $1\times10^6$. The molar ratio of structural units derived from the allyl carbonate of the above general formula (IV) to structural units derived from the compound of the above general formula (VII), (IX) and (X) generally ranges from 1:100 to 100:0, preferably from 1:50 to 90:10.

The molar ratio of structural units derived from the allyl carbonate of the above general formula (IV) to structural units derived from the compound of the above general formula (VII), (IX) and (X) is regulated within the above range in conformity with the desired physical and chemical properties of the copolymer.

When the molar ratio of structural units derived from the allyl carbonate of the above general formula (IV) to structural units derived from the compound of the above general formula (VII), (IX) and (X) falls outside the above range, problems may be encountered such that the ionic conductivity is lowered, and a viscosity and elasticity of the polymer are lowered, and the tensile strength is poor.

The above allyl carbonate polymer can be produced by customary methods. For example, it can easily be produced by polymerizing either at least one member selected from the group of the allyl carbonates represented by the above general formula (IV) or at least one member selected from the group of the allyl carbonates represented by the above general formula (IV) together with at least one compound selected from the group of the compounds represented by the above general formula (VII), (IX) and (X) according to the radical polymerization or photopolymerization technique.

Among them, it is preferably performed in a presence of a radical polymerization initiator. the initiator includes diisopropylperoxy dicarbonate.

More specifically, the following polymerization methods are included.

(1) With the mixture of at least one compound(s) from the formula (IV) and that from the formula (VII), (IX) and (X) is mixed diisopropylperoxydicarbonate homogeneously. The obtained mixture is heated to copolymerize the compound of the formula (IV) and that of the formula (VII), (IX) and (X).

(2) With the mixture of at least one compound(s) from the formula (IV) and that from the formula (VII), (IX) adn (X) is mixed diisopropylperoxydicarbonate homogeneously. The obtained mixture is irradiated by UV-ray or radioactive ray to copolymerize the compound of the formula (IV) and that of the formula (VII), (IX) and (X). In this method (2), a photosensitizer is employable. Such photosensitizer includes benzophenone, acetophenone, 2,2-dimethoxy-2-phenylacetophenone.

The first allyl carbonate polymer of the present invention may contain structural units other than the structural units derived from the monomers represented by the above general formulae (IV), (VII), (IX) and (X) in an amount of, for example, up to 20 mol %.

Second allyl carbonate polymer

The second allyl carbonate polymer of the present invention comprises:

structural units derived from at least one compound selected from the group of the compounds represented by the above general formula (IX) and structural units derived from at least one compound selected from the group of the compounds represented by the above general formula (VII).

The allyl carbonate polymer of the present invention generally has a molecular weight ranging from $2\times10^3$ to $1\times10^8$, preferably from $1\times10^4$ to $1\times10^7$. The molar ratio of structural units derived from the compound of the above general formula (IX) to structural units derived from the compound of the above general formula (VII) generally ranges from 10:90 to 99:1, preferably from 30:70 to 97:3 and still preferably from 50:50 to 95:5.

The molar ratio of structural units derived from the compound of the above general formula (IX) to structural units derived from the compound of the above general formula (VII) is regulated within the above range in conformity with the desired physical and chemical properties of the copolymer.

When the molar ratio of structural units derived from the compound of the above general formula (IX) to structural units derived from the compound of the above general formula (VII) falls outside the above range, problems may be encountered such that the ionic conductivity is lowered, and a viscosity and elasticity of the polymer are lowered, and the tensile strength is poor.

The above allyl carbonate copolymer can be produced by customary methods. For example, it can easily be produced by polymerizing at least one compound selected from the group of the compounds represented by the above general formula (IX) together with at least one compound selected from the group of the compounds represented by the above general formula (VII) according to the radical polymerization or photopolymerization technique.

The second allyl carbonate polymer of the present invention may contain structural units other than the structural units derived from the compound of the above general formula (IX) and structural units derived from the compound of the above general formula (VII) in an amount such that the properties of the copolymer of the present invention are not deteriorated, for example, up to 20 mol %.

Third allyl carbonate polymer

The third allyl carbonate polymer of the present invention comprises:

structural units derived from at least one compound selected from the group of the compounds represented by the above general formula (X) and structural units derived from at least one compound selected from the group of the compounds represented by the above general formula (VII).

The third allyl carbonate polymer of the present invention generally has a molecular weight ranging from $2\times 10^3$ to $1\times 10^8$, preferably from $1\times 10^4$ to $1\times 10^7$. The molar ratio of structural units derived from the compound of the above general formula (X) to structural units derived from the compound of the above general formula (VII) generally ranges from 10:90 to 99:1, preferably from 30:70 to 97:3 and still preferably from 50:50 to 95:5.

The molar ratio of structural units derived from the compound of the above general formula (X) to structural units derived from the compound of the above general formula (VII) is regulated within the above range in conformity with the desired physical and chemical properties of the copolymer.

When the molar ratio of structural units derived from the compound of the above general formula (X) to structural units derived from the compound of the above general formula (VII) falls outside the above range, problems may be encountered such that the ionic conductivity is lowered, and a viscosity and elasticity of the polymer are lowered, and the tensile strength is poor.

The above allyl carbonate copolymer can be produced by customary methods. For example, it can easily be produced by polymerizing at least one compound selected from the group of the compounds represented by the above general formula (X) together with at least one compound selected from the group of the compounds represented by the above general formula (VII) according to the radical polymerization or photopolymerization technique.

The third allyl carbonate polymer of the present invention may contain structural units other than the structural units derived from the compound of the above general formula (X) and structural units derived from the compound of the above general formula (VII) in an amount such that the properties of the copolymer of the present invention are not deteriorated, for example, up to 20 mol %.

Polymeric Solid Electrolyte

The polymeric solid electrolyte of the present invention comprises at least one polymer selected from the group of the above acrylic ester polymers, allyl ether polymers and allyl carbonate polymers and a salt of a metal of Group Ia of the periodic table, optionally together with a nonaqueous solvent.

It is preferred that the above salt of a metal of Group Ia of the periodic table is selected from the group consisting of LiBr, LiI, LiSCN, LiClO$_4$, LiBF$_4$, LiAsF$_6$, LiPF$_6$, LiCF$_3$SO$_3$, LiAlCl$_4$, LiN(CF$_3$SO$_2$)$_2$, LiC(CF$_3$SO$_2$)$_3$, NaBr, NaSCN, NaClO$_4$, KSCN and KClO$_4$. Of these, LiClO$_4$, LiBF$_4$, LiPF$_6$, LiAsF$_6$, LiCF$_3$SO$_3$, LiN(CF$_3$SO$_2$)$_2$ and LiC(CF$_3$SO$_2$)$_3$ are especially preferred. The above salts can be used singly or in combination of two or more kinds.

The salt of a metal of Group Ia of the periodic table is preferably contained in the polymeric solid electrolyte of the present invention in an amount of 5 to 50% by weight, especially 10 to 40% by weight based on the total weight of the polymeric solid electrolyte.

When the proportion of the salt of a metal of Group Ia of the periodic table to at least one polymer selected from the group of the above acrylic ester polymers, allyl ether polymers and allyl carbonate polymers falls outside the above range, problems may be encountered such that the ionic conductivity is lowered, and a viscosity and elasticity of the polymer are lowered, and the tensile strength is poor.

The polymeric solid electrolyte of the present invention can be produced by customary methods.

The polymeric solid electrolyte is generally used in the form of a film, so that the employment of the following methods is preferred.

1. Method comprising dissolving at least one polymer selected from the group of the above polymerized acrylic ester polymers, allyl ether polymers and allyl carbonate polymers and the Group Ia metal salt in a solvent or impregnating them with the solvent, and applying the resultant solution or mixture to a flat substrate by casting or coating, in which, optionally, the solvent is evaporated after the application. Although the solvent is not particularly limited as long as it can dissolve the polymer, the solvent can be selected from the group consisting of, for example, dimethyl carbonate, diethyl carbonate, ethyl methyl carbonate, propylene carbonate, ethylene carbonate, γ-butyrolactone, dimethylformamide, dimethylacetamide, tetrahydrofuran, dimethyl sulfoxide, N-methylpyrrolidone and sulfolane.

2. Method comprising dissolving one or more compounds set forth below in a solvent in the presence of the Group Ia metal salt, applying the resultant solution to a flat substrate by casting or coating, and irradiating ultraviolet or radiation or heating to effect polymerization and curing the resulting polymer.

(1) at least one compound selected from the group of the compounds represented by the above general formulae (I) to (IV);

(2) at least one member selected from the group of the acrylic esters represented by the above general formula (I) and at least one compound selected from the group of the compounds represented by the above general formulae (II) and (V) to (VIII);

(3) at least one member selected from a group of the acrylic esters represented by the above general formula (II) and at least one compound selected from the group of the compounds represented by the above general formulae (V) to (VIII);

(4) at least one member selected from the group of the allyl ethers represented by the above general formula (III) and at least one compound selected from the group of the compounds represented by the above general formulae (IV), (VII), (IX) and (X);

(5) at least one member selected from the group of the allyl carbonates represented by the above general formula (IV) and at least one compound selected from the group of the compounds represented by the above general formula (VII), (IX) and (X);

(6) at least one member selected from the group of the compounds represented by the above general formula (IX) and at least one compound selected from the group of the compounds represented by the above general formula (VII); and (7) at least one member selected from the group of the compounds represented by the above general formula (X) and at least one compound selected from the group of the compounds represented by the above general formula (VII).

In this method, the solvent may be evaporated after the spread of the solution on the flat substrate. Examples of suitable solvents include methyl ethyl ketone, dimethyl carbonate, diethyl carbonate, ethyl methyl carbonate, propylene carbonate, ethylene carbonate, γ-butyrolactone and dimethylformamide.

Further, a photosensitizer can be used in this method. Examples of suitable photosensitizers include benzophenone, acetophenone and 2,2-dimethoxy-2-phenylacetophenone.

3. Method comprising dissolving one or more compounds set forth in items (1) to (7) above in a solvent in the presence of the Group Ia metal salt and a polymerization initiator, applying the resultant solution to a flat substrate by casting or coating and heating the solution to effect polymerization and curing the resulting polymer. In this method, the solvent may be evaporated after the spread of the solution on the flat substrate. The same solvents as set forth in the method 2 can be used in this method as well.

A gelled polymeric solid electrolyte can be produced by performing the polymerization without the evaporation of the solvent in the methods 2 and 3.

In the present invention, the polymeric solid electrolyte may be in the form of a bulk or a gel.

The gelled polymeric solid electrolyte of the present invention comprises a member selected from the group of the above acrylic ester polymers, allyl ether polymers and allyl carbonate polymers, a salt of a metal of Group Ia of the periodic table and a nonaqueous solvent.

Salts set forth hereinbefore can be used as the salt of a metal of Group Ia of the periodic table.

The nonaqueous solvent is, for example, methyl ethyl ketone, dimethyl carbonate, diethyl carbonate, methyl ethyl carbonate, propylene carbonate, ethylene carbonate, γ-butyrolactone or dimethylformamide. Of these, propylene carbonate and ethylene carbonate are preferred.

The content of a nonaqueous solvent is preferred to range from 0 to 600 parts by weight, especially from 5 to 300 parts by weight based on 100 parts by weight of the acrylic ester polymer, allyl ether polymer and/or allyl carbonate polymer.

The polymeric solid electrolyte of the present invention exhibits high ionic conductivity and is electrochemically stable, so that it can be used in, for example, an electrochemical element such as a primary battery, a secondary battery, a capacitor or an electrochromic display and a medical actuator.

EFFECT OF THE INVENTION

Each of the novel acrylic ester, allyl ether and allyl carbonate according to the present invention can be a starting monomer capable of forming a polymer matrix for use in, for example, a polymeric solid electrolyte. The polymeric solid electrolyte comprising as a polymer matrix each of the acrylic ester polymer, allyl ether polymer and allyl carbonate polymer which have structural units derived from the acrylic ester, allyl ether and allyl carbonate according to the present invention, respectively, exhibits high ionic conductivity and is electrochemically stable.

Each of the acrylic ester polymer, allyl ether polymer and allyl carbonate polymer according to the present invention can be used, for example, as a polymer matrix in a polymeric solid electrolyte. The polymeric solid electrolyte comprising as a polymer matrix each of the acrylic ester polymer, allyl ether polymer and allyl carbonate polymer according to the present invention exhibits high ionic conductivity and is electrochemically stable.

The polymeric solid electrolyte of the present invention exhibits high ionic conductivity and is electrochemically stable, so that it can be used in, for example, an electrochemical element such as a primary battery, a secondary battery, a capacitor or an electrochromic display and a medical actuator.

EXAMPLE

The present invention will be illustrated below with reference to the following Examples, which in no way limit the scope of the invention.

The acrylic ester polymer, allyl ether polymer, allyl carbonate polymer and polymeric solid electrolyte were evaluated by the methods described later.

Example 1

Synthesis of Methacrylic Acid-2-Hydroxyethyl Methylcarbonate (2-Methacyloyloxyethyl Methyl Carbonate)

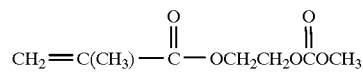

13.01 g (0.1 mol) of hydroxyethyl methacrylate, 27.00 g (0.3 mol) of dimethyl carbonate and 0.042 g (0.3 mmol) of potassium carbonate as a catalyst were charged into a 100 ml four-necked flask and reacted at 90° C. for 8 hr under reflux under agitation with removing formed methanol. After the completion of the reaction, potassium carbonate was removed by the use of a silica gel column and distillation was performed, thereby obtaining methacrylic acid-2-hydroxyethyl methylcarbonate (2-methacryloyloxyethyl methyl carbonate).

Figure 2:
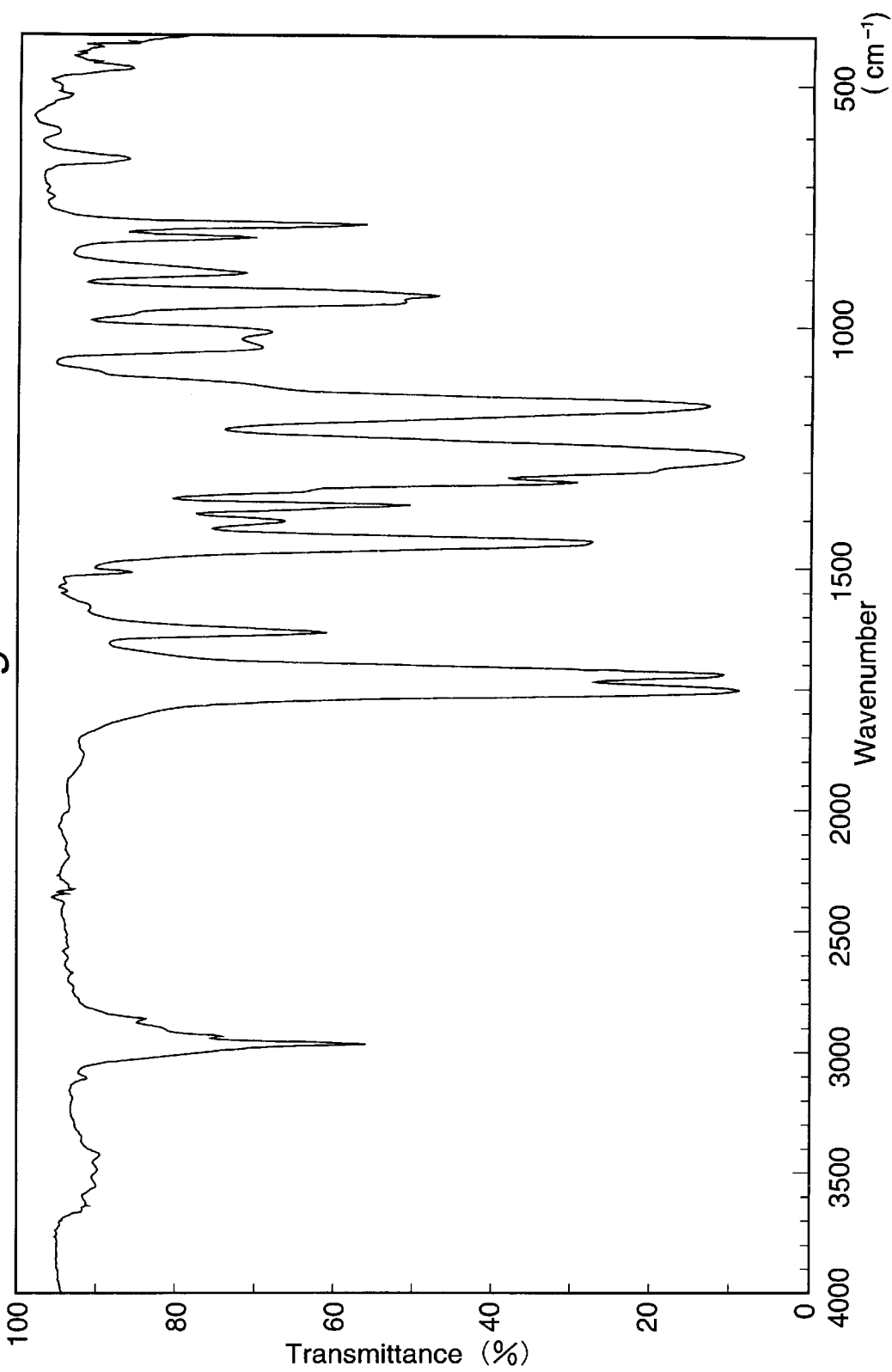
FIG. 2 is an IR spectrum of methacrylic acid-2-hydroxyethyl methylcarbonate (2-methacryloyloxyethyl methyl carbonate) obtained in Example 1.

Identification of the obtained methacrylic acid-2-hydroxyethyl methylcarbonate (2-methacryloyloxyethyl methyl carbonate) was conducted by $^1$H-NMR and IR. $^1$H-NMR and IR spectra are shown in FIGS. 1 and 2, respectively.

$^1$H-NMR (CDCl$_3$ solution, δ ppm); 1.95 (t, 3H, J=1.0 Hz, CH$_3$), 3.80 (s, 3H, CH$_3$), 4.38 (m, 4H, CH$_2$), 5.59 (t, 1H, J=1.5 Hz, CH), 6.14 (s, 1H, CH).

IR (neat, cm$^{-1}$): 2960 (C=H), 1755 (C=O), 1720 (C=O), 1640 (C=C), 1450, 1272, 1170, 1048, 1015, 935, 790.

Example 2

Synthesis of Methacrylic Acid-2-Hydroxyethoxyethyl Methylcarbonate (2(2-Methacryloyloxyethoxy)ethyl Methyl Carbonate)

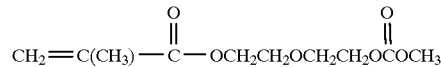

86.1 g of methacrylic acid, 106.1 g of diethylene glycol, 0.3 g of hydroquinone, 1.5 ml of concentrated sulfuric acid and 500 ml of toluene were charged into a 1 lit. four-necked flask equipped with an agitator, a water separator and a thermometer and an esterification reaction was performed at 110° C. under agitation with separating water. After the completion of the reaction for 3 hr, the resulting mixture was cooled to room temperature. The amount of formed water was 18 g.

The reaction mixture was concentrated with toluene removed and dissolved in a 1:1 (vol/vol) mixture of hexane and ether. The methacrylic acid as a raw material, sulfuric acid as a catalyst and desired diethylene glycol monomethyacrylate were extracted with 10% aqueous sodium bicarbonate. The water layer was further extracted with ether, and the concentration was conducted, thereby obtaining 52 g of diethylene glycol monomethyacrylate.

52 g (0.3 mol) of diethylene glycol monomethyacrylate, 270 g (3 mol) of dimethyl carbonate and 0.13 g (0.9 mmol) of potassium carbonate as a catalyst were charged into a 500 ml of four-necked flask and reacted at 90° C. for 8 hr under reflux under agitation with removing formed methanol. After the completion of the reaction, potassium carbonate was removed by the use of a silica gel column and distillation was performed, thereby obtaining methacrylic acid-2-hydroxyethoxyethyl methylcarbonate (2(2-methacryloyloxyethoxy)ethyl methyl carbonate).

Figure 3:
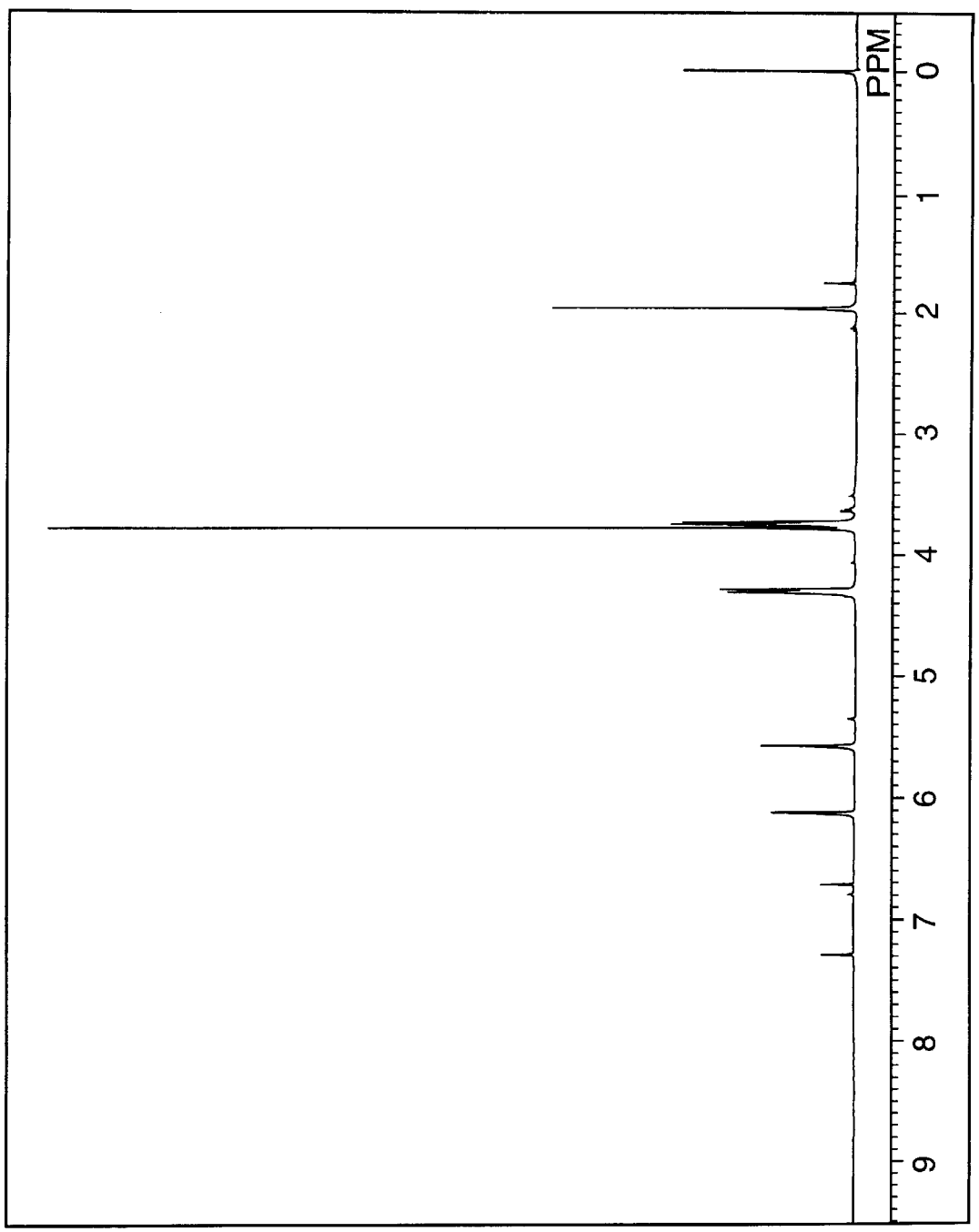
FIG. 3 is an NMR spectrum of methacrylic acid-2-hydroxyethoxyethyl methylcarbonate (2-(2-methacryloyloxyethoxy)ethyl methyl carbonate) obtained in Example 2.
Figure 4:
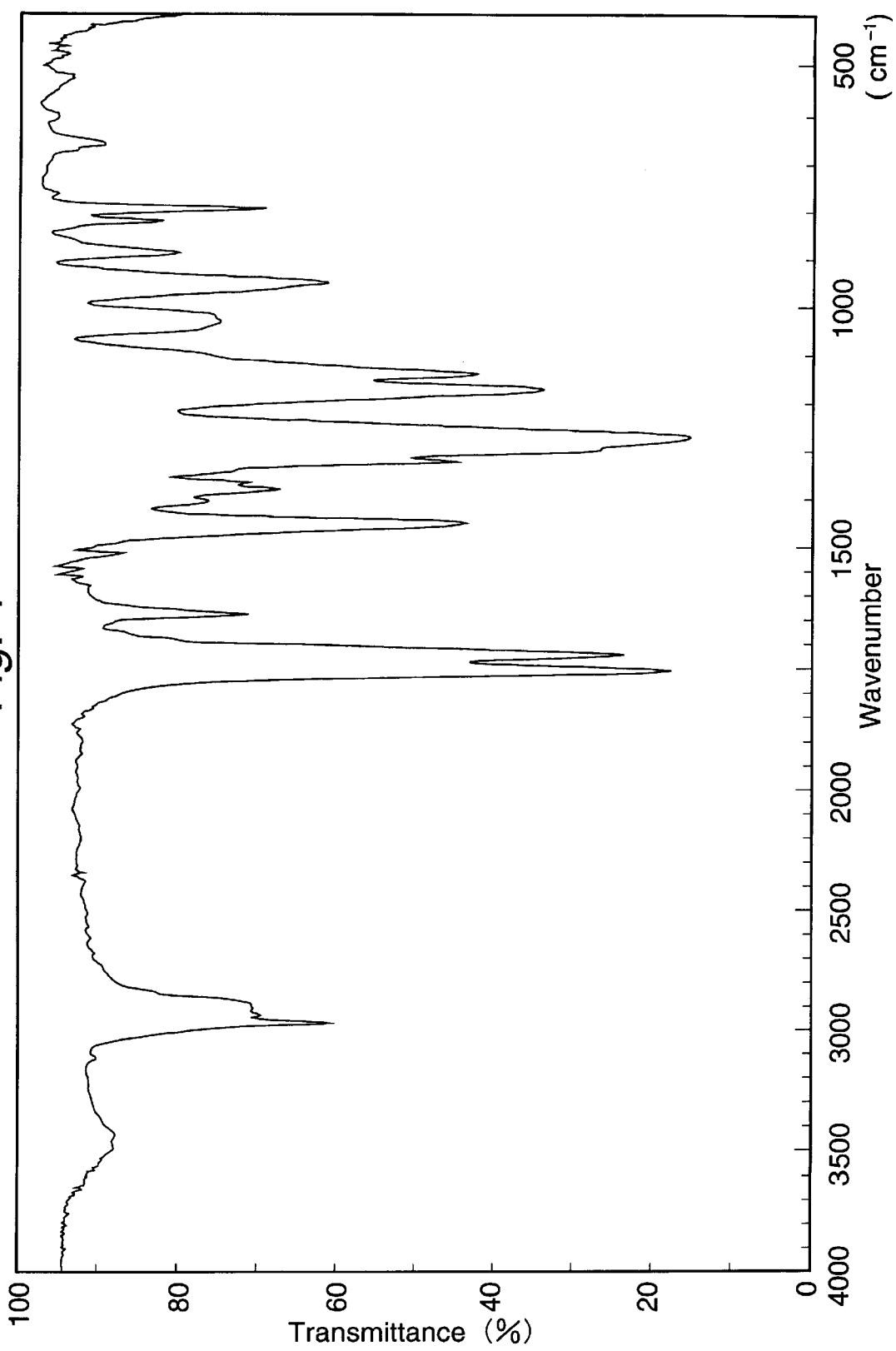
FIG. 4 is an IR spectrum of methacrylic acid-2-hydroxyethoxyethyl methylcarbonate (2-(2-methacryloyloxyethoxy)ethyl methyl carbonate) obtained in Example 2.

Identification of the obtained methacrylic acid-2-hydroxyethoxyethyl methylcarbonate (2(2-methacryloyloxyethoxy)ethyl methyl carbonate) was conducted by $^1$H-NMR and IR. $^1$H-NMR and IR spectra are shown in FIGS. 3 and 4, respectively.

$^1$H-NMR (CDCl$_3$ solution, δ ppm): 1.95 (t, 3H, J=1.3 Hz, CH$_3$), 3.75 (m, 4H, CH$_2$), 3.78 (s, 3H, CH$_3$), 4.30 (m, 4H, CH$_2$), 5.58 (t, 1H, J=1.5 Hz, CH), 6.70 (s, 1H, CH).

IR (neat, cm$^{-1}$): 2980 (C=H), 1750 (C=O), 1710 (C=O), 1640 (C=O), 1450, 1265, 1173, 1135, 1032, 952, 785.

Example 3

Preparation of Acrylic Ester Polymer 1.88 g (0.01 mol) of methacrylic acid-2-hydroxyethyl methylcarbonate (2-methacryloyloxyethyl methyl carbonate) produced in Example 1 was mixed with 41.6 μl of Peroyl IPP50 (produced by Nippon Oil & Fats Co., Ltd.). The thus obtained homogeneous liquid was cast on a Teflon-coated glass plate and cured at 70° C. in inert gas atmosphere for 24 hr, thereby obtaining a transparent solid. A polymerization was confirmed by the extinction of absorption at 1640 cm$^{-1}$ ascribed to C=C vibration in an IR spectrum of the solid.

Example 4

Preparation of Acrylic Ester Polymer

The same curing and confirmation of polymerization by IR spectrum as in Example 3 were executed using the methacrylic acid-2-hydroxyethoxyethyl methylcarbonate (2(2-methacryloyloxyethoxy)ethyl methyl carbonate) produced in Example 2.

Example 5

Preparation of Acrylic Ester Copolymer 0.94 g (0.005 mol) of methacrylic acid-2-hydroxyethyl methylcarbonate (2-methacryloyloxyethyl methyl carbonate) produced in Example 1, 1.16 g (0.005 mol) of methacrylic acid-2-hydroxyethoxyethyl methylcarbonate (2(2-methacryloyloxyethoxy)ethyl methyl carbonate) produced in Example 2 and 41.6 μl of Peroyl IPP50 were mixed together. The thus obtained homogeneous liquid was cast on a Teflon-coated glass plate and cured at 70° C. in inert gas atmosphere for 24 hr, thereby obtaining a transparent solid. A polymerization was confirmed by the extinction of absorption at 1640 cm$^{-1}$ ascribed to C=C vibration in an IR spectrum of the solid.

Example 6

Preparation of Methacrylic Acid-2-Hydroxyethyl Methylcarbonate (2(2-methoxyethoxy)ethyl Methacrylate) Copolymer 0.94 g (0.005 mol) of Methacrylic acid-2-hydroxyethyl methylcarbonate (2-methacryloxyethyl methyl carbonate) produced in Example 1, 0.94 g (0.005 mol) of methoxyethoxyethyl methacrylate (2(2-methoxyethoxy)ethyl methacrylate)

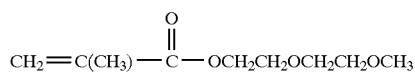

and 41.6 μl of Peroyl IPP50 were mixed together. The thus obtained homogeneous liquid was cast on a Teflon-coated glass plate and cured at 70° C. in inert gas atmosphere for 24 hr, thereby obtaining a transparent solid. A polymerization was confirmed by the extinction of absorption at 1640 cm$^{-1}$ ascribed to C=C vibration in an IR spectrum of the solid.

Example 7

A copolymer was prepared in the same manner as in Example 6 except that diethylene glycol dimethacrylate (di(2-methacryloyloxyethyl)ether):

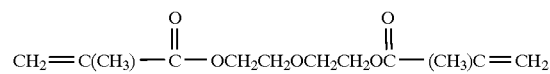

was employed in place of methoxyethoxyethyl methacrylate (2(2-methoxyethoxy)ethyl methacrylate). A polymerization was confirmed by the extinction of absorption at 1640 cm$^{-1}$ ascribed to C=C vibration in an IR spectrum of the copolymer.

Figure 5:
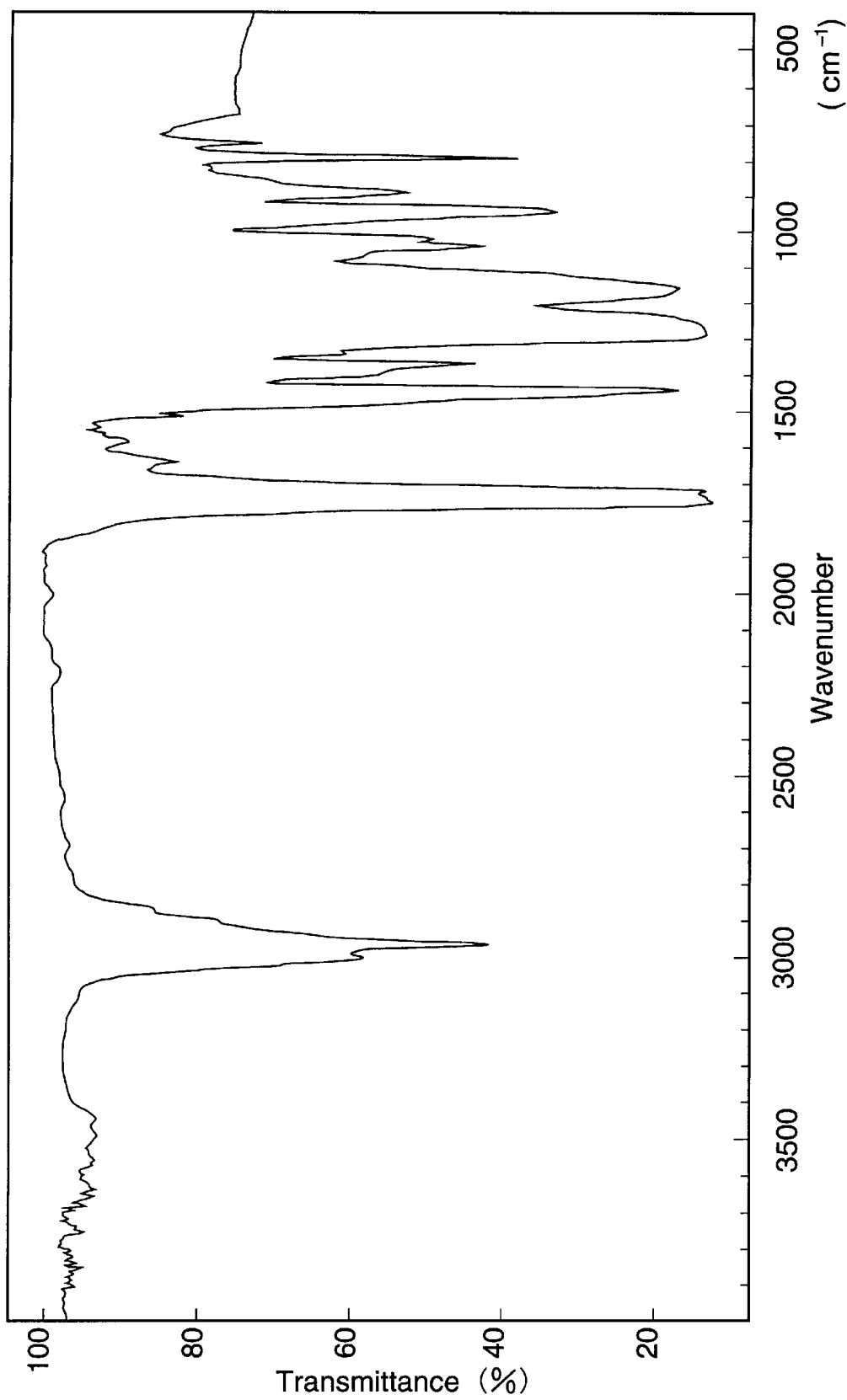
FIG. 5 is an IR spectrum of a copolymer of methacrylic acid-2-hydroxyethyl methyl carbonate (2-methacryloyloxyethyl methyl carbonate) and diethylene glycol dimethacrylate obtained in Example 7.

The obtained IR spectrum is shown in FIG. 5.

Example 8

A copolymer was prepared in the same manner as in Example 6 except that di-2-methacryloxyethyl carbonate (di(2-methacryloyloxyethyl)carbonate) was employed in place of methoxyethoxyethyl methacrylate (2(2-methoxyethoxy)ethyl methacrylate).

Example 9

Preparation of Methacrylic Acid-2-Hydroxyethoxyethyl Methylcarbonate (2(2-Methacryloyloxyethoxy)ethyl Methyl Carbonate) Copolymer 1.16 g (0.005 mol) of methacrylic acid-2-hydroxyethoxyethyl methylcarbonate (2(2-methacryloyloxyethoxy)ethyl methyl carbonate) produced in Example 2, 0.94 g (0.005 mol) of methoxyethoxyethyl methacrylate and 41.6 μl of Peroyl IPP50 were mixed together. The thus obtained homogeneous liquid was cast on a Teflon-coated glass plate and cured at 70° C. in inert gas atmosphere for 24 hr, thereby obtaining a transparent solid. A polymerization was confirmed by the extinction of absorption at 1640 cm$^{-1}$ ascribed to C=C vibration in an IR spectrum of the solid.

Example 10

A copolymer was prepared in the same manner as in Example 9 except that diethylene glycol dimethacrylate was employed in place of methoxyethoxyethyl methacrylate.

Example 11

A copolymer was prepared in the same manner as in Example 9 except that di-2-methacryloxyethyl carbonate (di(2-methacryloyloxyethyl)carbonate) was employed in place of methoxyethoxyethyl methacrylate.

Example 12

Production of Polymeric Solid Electrolyte and Measurement of Ionic Conductivity

50% by weight of methacrylic acid-2-hydroxyethyl methylcarbonate (2-methacryloyloxyethyl methyl carbonate) produced in Example 1, 50% by weight of propylene carbonate, 2 mol %, based on the carbonate units, of Group Ia metal salt of the formula LiN(CF$_3$SO$_2$)$_2$ and 1 mol %, based on the monomers, of Peroyl IPP50 were mixed together. The thus obtained homogeneous liquid was cast on a Teflon-coated glass plate and cured at 70° C. in dry inert gas atmosphere for 24 hr, thereby obtaining a thin-film polymeric solid electrolyte of about 1 mm in thickness composed of the acrylic ester polymer and the Group Ia metal salt. A polymerization was confirmed by the extinction of absorption at 1640 cm$^{-1}$ ascribed to C=C vibration in an IR spectrum of the electrolyte.

In the present invention, the thus obtained thin-film polymeric solid electrolyte was punched to thereby obtain a disc of 10 mmφ in diameter. This disc was interposed between electrodes and fitted in an impedance measuring holder, and the impedance thereof was measured by means of impedance analyzer HP4285A (measuring voltage: 10 mV) with controlling the temperature of the electrodes with the use of Peltier device. Thus, the ionic conductivity was analytically determined. The results are given in Table 1.

Example 13

A polymeric solid electrolyte was produced in the same manner as in Example 12 except that Methacrylic acid-2-hydroxyethoxyethyl methylcarbonate (2(2-methacryloyloxyethoxy)ethyl methyl carbonate) produced in Example 2 was employed in place of methacrylic acid-2-hydroxyethyl methylcarbonate (2-methacryloyloxyethyl methyl carbonate).

The ionic conductivity of the obtained polymeric solid electrolyte was measured in the same manner as in Example 12. The results are given in Table 1.

Example 14

A polymeric solid electrolyte was produced in the same manner as in Example 12 except that a 5:5 (mol:mol) monomer mixture of methacrylic acid-2-hydroxyethyl methylcarbonate (2-methacryloyloxyethyl methyl carbonate) produced in Example 1 and methacrylic acid-2-hydroxyethoxyethyl methylcarbonate (2(2-methacryloyloxyethoxy)ethyl methyl carbonate) produced in Example 2 was employed in place of methacrylic acid-2-hydroxyethyl methylcarbonate (2-methacryloyloxyethyl methyl carbonate).

The ionic conductivity of the obtained polymeric solid electrolyte was measured in the same manner as in Example 12. The results are given in Table 1.

Example 15

70% by weight of a 5:5 (mol:mol) monomer mixture of methacrylic acid-2-hydroxyethyl methylcarbonate (2-methacryloyloxyethyl methyl carbonate) produced in Example 1 and methoxyethoxyethyl methacrylate, 30% by weight of propylene carbonate, 2 mol %, based on the carbonate units, of Group Ia metal salt of the formula LiN(CF$_3$SO$_2$)$_2$ and 1 mol %, based on the monomers, of Peroyl IPP50 were mixed together. The thus obtained homogeneous liquid was cast on a Teflon-coated glass plate and cured at 70° C. in dry inert gas atmosphere for 24 hr, thereby obtaining a polymeric solid electrolyte composed of the acrylic ester polymer and the Group Ia metal salt. A polymerization was confirmed by the extinction of absorption of 1640 cm$^{-1}$ ascribed to C=C vibration in an IR spectrum of the electrolyte.

The ionic conductivity of the obtained polymeric solid electrolyte was measured in the same manner as in Example 12. The results are given in Table 1.

Example 16

A polymeric electrolyte was produced in the same manner as in Example 15 except that diethylene glycol dimethacrylate was employed in place of methoxyethoxyethyl methacrylate and that the monomer ratio of the mixture was changed to 9:1 (mol:mol).

The ionic conductivity of the obtained polymeric solid electrolyte was measured in the same manner as in Example 12. The results are given in Table 1.

Example 17

A polymeric solid electrolyte was produced in the same manner as in Example 15 except that di-2-methacryloxyethyl carbonate (di(2-methacryloyloxyethyl) carbonate) was employed in place of methoxyethoxyethyl methacrylate and that the monomer ratio of the mixture was changed to 9:1 (mol:mol).

The ionic conductivity of the obtained polymeric solid electrolyte was measured in the same manner as in Example 12. The results are given in Table 1.

Example 18

70% by weight of a 5:5 (mol:mol) monomer mixture of methacrylic acid-2-hydroxyethoxyethyl methylcarbonate (2(2-methacryloyloxyethoxy)ethyl methyl carbonate) produced in Example 2 and methoxyethoxyethyl methacrylate, 30% by weight of propylene carbonate, 2 mol %, based on the carbonate units, of Group Ia metal salt of the formula LiN(CF$_3$SO$_2$)$_2$ and 1 mol %, based on the monomers, of Peroyl IPP50 were mixed together. The thus obtained homogeneous liquid was cast on a Teflon-coated glass plate and cured at 70° C. in inert gas atmosphere for 24 hr, thereby obtaining a polymeric solid electrolyte composed of the acrylic ester polymer and the Group Ia metal salt. A polymerization was confirmed by the extinction of absorption at 1640 cm$^{-1}$ ascribed to C=C vibration in an IR spectrum of the electrolyte.

The ionic conductivity of the obtained polymeric solid electrolyte was measured in the same manner as in Example 12. The results are given in Table 1.

Example 19

A polymeric solid electrolyte was produced in the same manner as in Example 18 except that diethylene glycol dimethacrylate was employed in place of methoxyethoxyethyl methacrylate and that the monomer ratio of the mixture was changed to 9:1 (mol:mol).

The ionic conductivity of the obtained polymeric solid electrolyte was measured in the same manner as in Example 12. The results are given in Table 1.

Example 20

A polymeric solid electrolyte was produced in the same manner as in Example 18 except that di-2-methacryloxyethyl carbonate (di(2-methacryloyloxyethyl) carbonate) was employed in place of methoxyethoxyethyl methacrylate and that the monomer ratio of the mixture was changed to 9:1 (mol:mol).

The ionic conductivity of the obtained polymeric solid electrolyte was measured in the same manner as in Example 12. The results are given in Table 1.

TABLE 1

Measurement of Ionic Conductivity
(measured at 25° C.)

| Example | Conductivity (S/cm) |
| --- | --- |
| 12 | $8.5 \times 10^{-4}$ |
| 13 | $1.9 \times 10^{-3}$ |
| 14 | $1.9 \times 10^{-3}$ |
| 15 | $7.5 \times 10^{-5}$ |
| 16 | $1.8 \times 10^{-6}$ |
| 17 | $1.1 \times 10^{-5}$ |
| 18 | $4.8 \times 10^{-5}$ |
| 19 | $3.9 \times 10^{-5}$ |
| 20 | $8.8 \times 10^{-6}$ |

Example 21

5.0 g of methacrylic acid-2-hydroxyethyl methylcarbonate (2-methacryloyloxyethyl methyl carbonate) produced in Example 1, 0.5 g of LiClO$_4$, 5.0 g of methyl ethyl ketone and 0.025 g of benzophenone were mixed together. The thus obtained homogeneous solution was cast on a glass plate in dry inert gas atmosphere and the methyl ethyl ketone was evaporated off. The resultant layer was irradiated with ultraviolet rays in dry inert gas atmosphere to thereby polymerize and cure the methacrylic acid-2-hydroxyethyl methylcarbonate (2-methacryloyloxyethyl methyl carbonate). Thus, a polymeric solid electrolyte composed of the acrylic ester polymer and the Group Ia metal salt (LiClO$_4$) was obtained.

Example 22

A polymeric solid electrolyte was produced in the same manner as in Example 21 except that propylene carbonate was employed in place of methyl ethyl ketone and that the propylene carbonate was not evaporated off.

Example 23

5.0 g of Methacrylic acid-2-hydroxyethyl methylcarbonate (2-methacyloyloxyethyl methyl carbonate) produced in Example 1, 0.5 g of LiBF$_4$, 5.0 g of methyl ethyl ketone and 0.025 g of benzoyl peroxide were mixed together. The thus obtained homogeneous solution was cast on a Teflon plate in dry inert gas atmosphere and the methyl ethyl ketone was evaporated off. The resultant layer was heated at 80° C. to thereby polymerize and cure the methacrylic acid-2-hydroxyethyl methylcarbonate (2-methacyloyloxyethyl methyl carbonate). Thus, a polymeric solid electrolyte composed of the acylic ester polymer and the Group Ia metal salt (LiBF$_4$) was obtained.

Example 24

5.0 g of methacrylic acid-2-hydroxethyl methylcarbonate (2-methacryloyloxyethyl methyl carbonate) produced in Example 1, 2.5 g of diethylene glycol dimethacrylate (produced by Shin-Nakamura Chemical Co., Ltd.), 0.5 g of LiN(CF$_3$SO$_2$)$_2$ and 5.0 g of methyl ethyl ketone were mixed together. The thus obtained homogeneous solution was cast on a glass plate in dry inert gas atmosphere and the methyl ethyl ketone was evaporated off. The resultant layer was irradiated with electron beams in dry inert gas atmosphere to thereby polymerize and cure the methacrylic acid-2-hydroxyethyl methylcarbonate (2-methacryloyloxyethyl methyl carbonate) together with the diethylene glycol dimethacrylate. Thus, a polymeric solid electrolyte composed of the acrylic ester copolymer and the Group Ia metal salt [LiN(CF$_3$SO$_2$)$_2$] was obtained.

Example 25

A polymeric solid electrolyte was produced in the same manner as in Example 24 except that propylene carbonate was employed in place of methyl ethyl ketone and that the propylene carbonate was not evaporated off.

Example 26

Synthesis of di-2-Methacryloxyethyl Carbonate (di (2-Methacryloyloxyethyl)Carbonate)

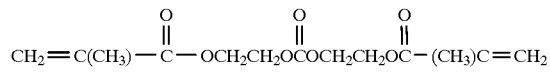

13.01 g (0.1 mol) of hydroxyethyl methacrylate, 28.60 g (0.1 mol) of methacrylic acid-2-hydroxyethyl methylcarbonate (2-methacryloyloxyethyl methyl carbonate) and 0.042 g (0.3 mmol) of potassium carbonate as a catalyst were charged into a 100 ml four-necked flask and reacted at 90° C. for 8 hr under reflux under agitation with removing formed methanol. After the completion of the reaction, potassium carbonate was removed by the use of a silica gel column and distillation was performed, thereby obtaining di-2-methacryloxyethyl carbonate (di(2-methacryloyloxyethyl)carbonate).

Figure 6:
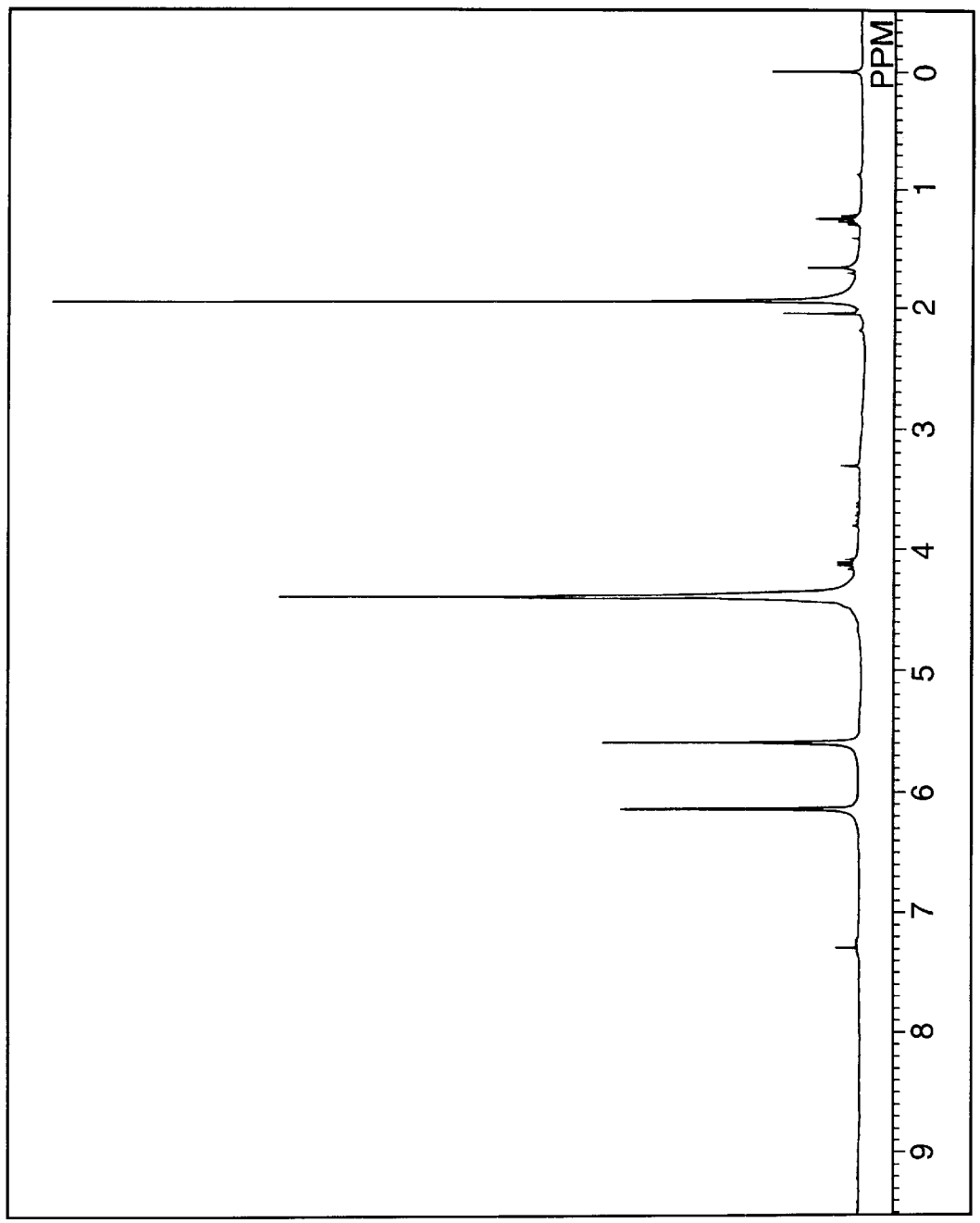
FIG. 6 is an NMR spectrum of di-2-methacryloxy ethyl carbonate (di(2-methacryloyloxyethyl) carbonate) obtained in Example 26.
Figure 7:
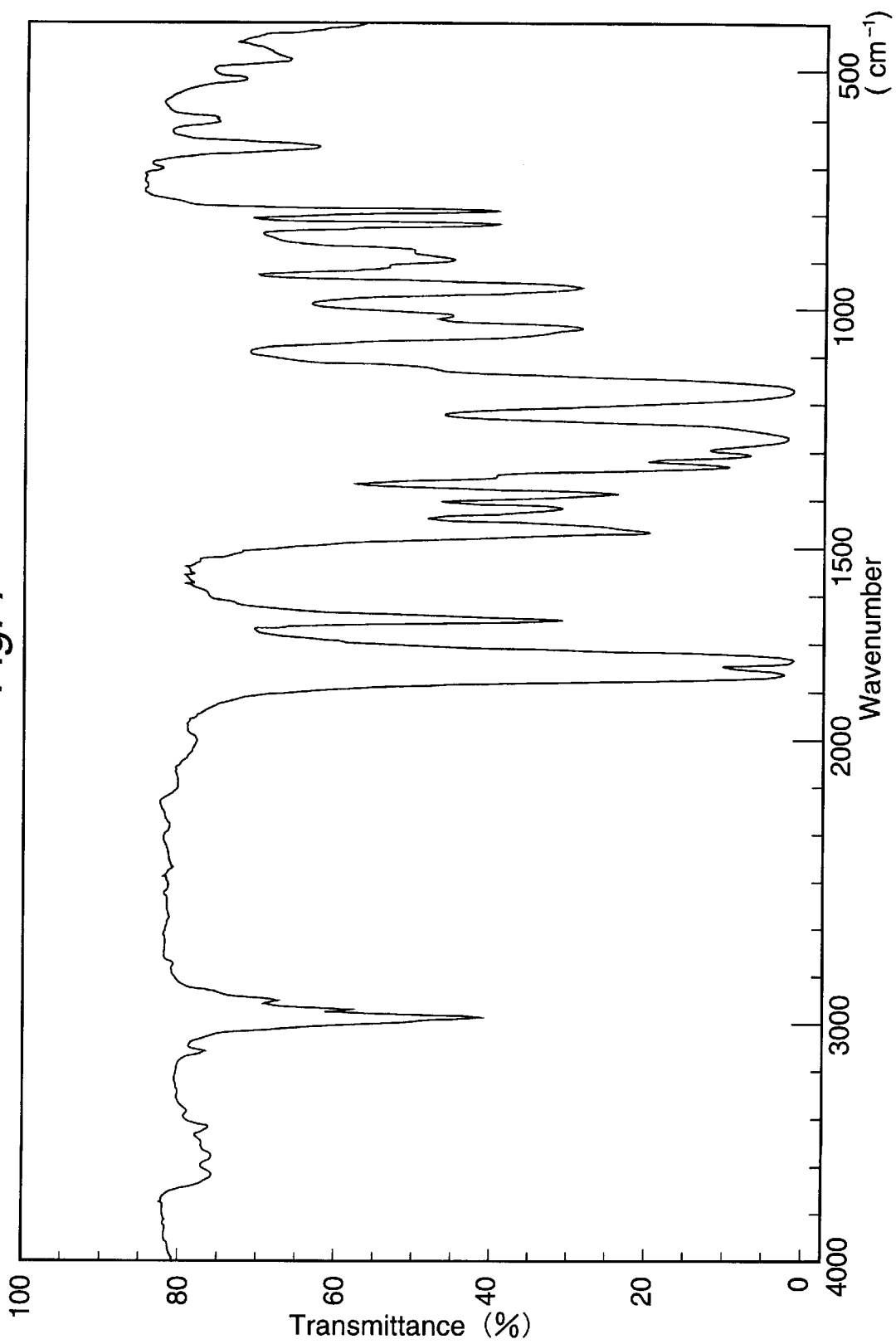
FIG. 7 is an IR spectrum of di-2-methacryloxy ethyl carbonate (di(2-methacryloyloxyehtyl) carbonate) obtained in Example 26.

Identification of the obtained di-2-methacryloxyethyl carbonate (di(2-methacryloyloxyethyl)carbonate) was conducted by $^1$H-NMR and IR. $^1$H-NMR and IR spectra are shown in FIGS. 6 and 7, respectively.

$^1$H-NMR (CDCl$_3$ solution, δ ppm): 1.95 (t, 6H, J=0.8 Hz, CH$_3$), 4.40 (m, 8H, CH$_2$), 5.60 (t, 2H, J=1.1 Hz, CH), 6.14 (t, 2H, J=1.1 Hz, CH).

IR (neat, cm$^{-1}$): 2980 (C=H), 1760 (C=O), 1738 (C=O), 1640 (C=C), 1460, 1265, 1163, 1038, 950, 818, 795.

Example 26'

Synthesis of di(2-Methacryloyloxyethyl)Carbonate

A 500 ml four-necked flask was charged with 152.2 g (1 mol) of 2-benzyloxyethanol, 90.1 g (1 mol) of dimethyl carbonate and 1.23 g (0.01 mol) of potassium carbonate as a catalyst, and they were reacted under reflux at 90° C. for 8 hours with stirring, while methanol produced was removed. Then, the temperature of the system was raised to 120° C., and the reaction was further performed for another 4 hours under reduced pressure, while methanol was removed. After the reaction was completed, potassium carbonate was removed by means of a silica gel column, and the reaction solution was distilled to obtain di(2-benzyloxyethyl)carbonate.

A 300 ml eggplant type flask was charged with 33.40 g (0.1 mol) of the di(2-benzyloxyethyl)carbonate obtained above, 9.9 g of 5% Pd/C and 100 ml of tetrahydrofuran, and they were reacted at room temperature for 5 hours in an atmosphere of hydrogen with vigorous stirring. Then, the reaction mixture was filtered, and the solvent was distilled off from the filtrate under reduced pressure to obtain di(2-hydroxyethyl) carbonate.

A 500 ml eggplant type flask was charged with 15.01 g (0.1 mol) of the di(2-hydroxyethyl) carbonate obtained above, 21.95 g (0.21 mol) of methacryloyl chloride, 19.78 g (0.25 mol) of pyridine and 100 ml of dichloromethane, and they were reacted at 5° C. for 2 hours in a dry inert gas atmosphere with stirring. After the completion of the reaction, ethylacetate and water were added to the reaction mixture, the desired carbonate were extracted to the organic layer, and the solvent was distilled off under reduced pressure to obtain a crude product. The crude product was purified by silica gel chromatography using a mixed solvent of hexane/tetrahydrofuran (5/1 by volume) as a developing solvent, to obtain the aimed di(2-methacryloyloxyethyl) carbonate.

Identification of the di(2-methacryloyloxyethyl) carbonate was made by carrying out $^1$H-NMR measurement and IR measurement.

Example 27

Preparation of Acrylic Ester Polymer 2.86 g (0.01 mol) of di-2-methacryloxyethyl carbonate (di(2-methacryloyloxyethyl) carbonate) produced in Example 26 or 26' was mixed with 41.6 μl of Peroyl IPP50 (produced by Nippon Oil & Fats Co., Ltd.). The thus obtained homogeneous liquid was cast on a Teflon-coated glass plate and cured at 70° C. in dry inert gas atmosphere for 24 hr, thereby obtaining a transparent solid. A polymerization was confirmed by the extinction of absorption at 1640 cm$^{-1}$ ascribed to C=C vibration in an IR spectrum of the solid.

Example 28

Preparation of di-2-Methacryloxyethyl Carbonate (di(2-Methacryloyloxyethyl) Carbonate) Copolymer 1.43 g (0.005 mol) of di-2-methacryloxyethyl carbonate (di(2-methacryloyloxyethyl) carbonate) produced in Example 26 or 26', 0.94 g (0.005 mol) of methoxyethoxyethyl methacrylate and 41.6 μl of Peroyl IPP50 were mixed together. The thus obtained homogeneous liquid was cast on a Teflon-coated glass plate and cured at 70° C. in dry inert gas atmosphere for 24 hr, thereby obtaining a transparent solid. A polymerization was confirmed by the extinction of absorption at 1640 cm$^{-1}$ ascribed to C=C vibration in an IR spectrum of the solid.

Example 29

A copolymer was prepared in the same manner as in Example 28 except that diethylene glycol dimethacrylate was employed in place of methoxyethoxyethyl methacrylate. A polymerization was confirmed by the extinction of absorption at 1640 cm$^{-1}$ ascribed to C=C vibration in an IR spectrum of the copolymer, as in Example 28.

Figure 8:
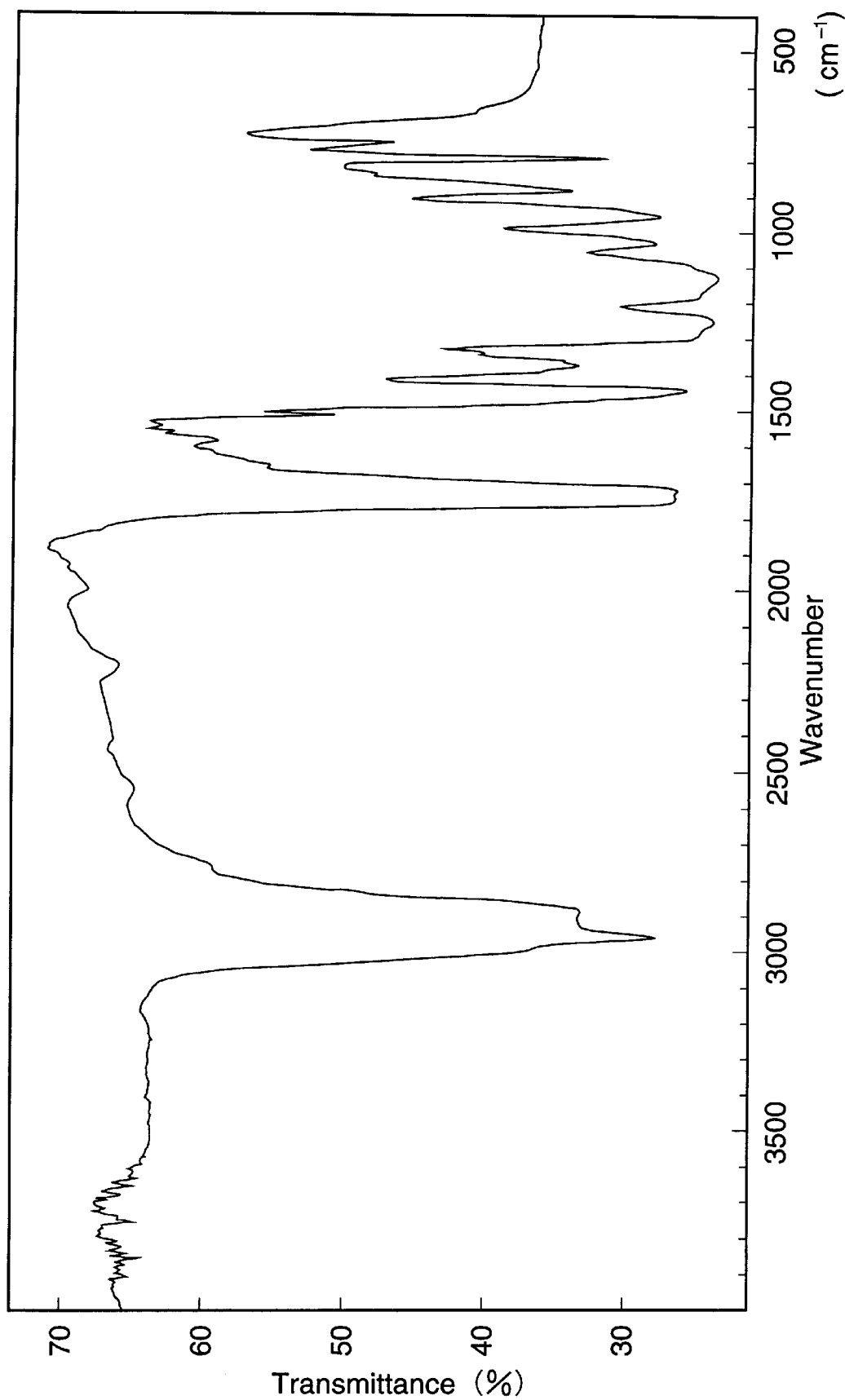
FIG. 8 is an IR spectrum of a copolymer of di-2-methacryloxy ethyl carbonate (di(2-methacryloyloxyethyl) carbonate) and diethylene glycol dimethacrylate obtained in Example 29.

The obtained IR spectrum is shown in FIG. 8.

Example 30

A copolymer was prepared in the same manner as in Example 28 except that methacrylic acid-2-hydroxyethyl methylcarbonate (2-methacryloyloxyethyl methyl carbonate) was employed in place of methoxyethoxyethyl methacrylate.

Example 31

A copolymer was prepared in the same manner as in Example 28 except that methacrylic acid-2-hydroxyethoxyethyl methylcarbonate (2(2-methacryloyloxyethoxy)ethyl methyl carbonate) was employed in place of methoxyethoxyethyl methacrylate.

Example 32

Production of Polymeric Solid Electrolyte and Measurement of Ionic Conductivity

50% by weight of di-2-methacryloxyethyl carbonate (di-2-methacryloyloxyethyl) carbonate) produced in Example 26 or 26', 50% by weight of propylene carbonate, 2 mol %, based on the carbonate units, of Group Ia metal salt of the formula LiN(CF$_3$SO$_2$)$_2$ and 1 mol %, based on the monomers, of Peroyl IPP50 were mixed together. The thus obtained homogeneous liquid was cast on a Teflon-coated glass plate and cured at 70° C. in dry inert gas atmosphere for 24 hr, thereby obtaining a polymeric solid electrolyte composed of the acrylic ester polymer and the Group Ia metal salt. A polymerization was confirmed by the extinction of absorption at 1640 cm$^{-1}$ ascribed to C=C vibration in an IR spectrum of the electrolyte.

The ionic conductivity of the obtained thin-film polymeric solid electrolyte was measured in the same manner as in Example 12. The results are given in Table 2.

Example 33

A polymeric solid electrolyte was produced in the same manner as in Example 32 except that di-2-methacryloxyethyl carbonate (di(2-methacryloyloxyethyl) carbonate) and propylene carbonate were used in respective amounts of 30% by weight and 70% by weight.

The ionic conductivity of the obtained thin-film polymeric solid electrolyte was measured in the same manner as in Example 12. The results are given in Table 2.

Example 34

70% by weight of a 1:9 (mol:mol) monomer mixture of di-2-methacryloxyethyl carbonate (di(2-methacryloyloxyethyl) carbonate) produced in Example 26 or 26' and methoxyethoxyethyl methacrylate, 30% by weight of propylene carbonate, 2 mol %, based on the carbonate units, of Group Ia metal salt of the formula LiN(CF$_3$SO$_2$)$_2$ and 1 mol %, based on the monomers, of Peroyl IPP50 were mixed together. The thus obtained homogeneous liquid was cast on a Teflon-coated glass plate and cured at 70° C. in dry inert gas atmosphere for 24 hr, thereby obtaining a polymeric solid electrolyte composed of the acrylic ester polymer and the Group Ia metal salt. A polymerization was confirmed by the extinction of absorption at 1640 cm$^{-1}$ ascribed to C=C vibration in an IR spectrum of the electrolyte.

The ionic conductivity of the obtained thin-film polymeric solid electrolyte was measured in the same manner as in Example 12. The results are given in Table 2.

Example 35

A polymeric solid electrolyte was produced in the same manner as in Example 34 except that methacrylic acid-2-hydroxyethyl methylcarbonate (2-methacryloyloxyethyl methyl carbonate) produced in Example 1 was employed in place of methoxyethoxyethyl methacrylate.

The ionic conductivity of the obtained thin-film polymeric solid electrolyte was measured in the same manner as in Example 12. The results are given in Table 2.

Example 36

A polymeric solid electrolyte was produced in the same manner as in Example 34 except that methacrylic acid-2-hydroxyethoxyethyl methylcarbonate (2(2-methacryloyloxyethoxy)ethyl methyl carbonate) produced in Example 2 was employed in place of methoxyethoxyethyl methacrylate.

The ionic conductivity of the obtained thin-film polymeric solid electrolyte was measured in the same manner as in Example 12. The results are given in Table 2.

Example 37

50% by weight of a 5:5 (mol:mol) monomer mixture of di-2-methacryloxyethyl carbonate (di(2-methacryloyloxyethyl) carbonate) produced in Example 26 or 26' and diethylene glycol monomethyacrylate (2(2-methoxyethoxy)ethyl methacrylate), 50% by weight of propylene carbonate, 2 mol %, based on the carbonate units, of Group Ia metal salt of the formula LiN(CF$_3$SO$_2$)$_2$ and 1 mol %, based on the monomers, of Peroyl IPP50 were mixed together. The thus obtained homogeneous liquid was cast on a Teflon-coated glass plate and cured at 70° C. in dry inert gas atmosphere for 24 hr, thereby obtaining a polymeric solid electrolyte composed of the acrylic ester polymer and the Group Ia metal salt. A polymerization was confirmed by the extinction of absorption at 1640 cm$^{-1}$ ascribed to C=C vibration in an IR spectrum of the electrolyte.

The ionic conductivity of the obtained thin-film polymeric solid electrolyte was measured in the same manner as in Example 12. The results are given in Table 2.

Example 38

A polymeric solid electrolyte was produced in the same manner as in Example 37 except that the monomer mixture and propylene carbonate were used in respective amounts of 30% by weight and 70% by weight.

The ionic conductivity of the obtained thin-film polymeric solid electrolyte was measured in the same manner as in Example 12. The results are given in Table 2.

TABLE 2

Measurement of Ionic Conductivity (measured at 25° C.)

| Example | Conductivity (S/cm) |
| --- | --- |
| 32 | 7.2 × 10$^{-7}$ |
| 33 | 2.5 × 10$^{-3}$ |
| 34 | 2.1 × 10$^{-5}$ |
| 35 | 3.1 × 10$^{-6}$ |
| 36 | 8.8 × 10$^{-6}$ |
| 37 | 1.1 × 10$^{-5}$ |
| 38 | 2.0 × 10$^{-3}$ |

Example 39

Production of Polymeric Solid Electrolyte 5.0 g of di-2-methacryloxyethyl carbonate (di(2-methacryloyloxyethyl) carbonate) produced in Example 26 or 26', 0.5 g of LiClO$_4$, 5.0 g of methyl ethyl ketone and 0.005 g of benzophenone were mixed together. The thus obtained homogeneous solution was cast on a glass plate in dry inert gas atmosphere and the methyl ethyl ketone was evaporated off. The resultant layer was irradiated with ultraviolet rays in dry inert gas atmosphere to thereby polymerize and cure the di-2-methacryloxyethyl carbonate. Thus, a polymeric solid electrolyte composed of the acrylic ester polymer and the Group Ia metal salt (LiClO$_4$) was obtained.

Example 40

A polymeric solid electrolyte was produced in the same manner as in Example 39 except that propylene carbonate was employed in place of methyl ethyl ketone and that the propylene carbonate was not evaporated off.

Example 41

5.0 g of di-2-methacryloxyethyl carbonate (di(2-methacryloyloxyethyl) carbonate) produced in Example 26 or 26', 0.5 g of LiOSO$_2$CF$_3$, 5.0 g of methyl ethyl ketone and 0.025 g of benzoyl peroxide were mixed together. The thus obtained homogeneous solution was cast on a Teflon plate in dry inert gas atmosphere and the methyl ethyl ketone was evaporated off. The resultant layer was heated at 80° C. to thereby polymerize and cure the di-2-methacryloxyethyl carbonate (di(2-methacryloyloxyethyl) carbonate). Thus, a polymeric solid electrolyte composed of the acrylic ester polymer and the Group Ia metal salt (LiOSO$_2$CF$_3$) was obtained.

Example 42

5.0 g of di-2-methacryloxyethyl carbonate (di(2-methacryloyloxyethyl) carbonate) produced in Example 26 or 26', 2.5 g of diethylene glycol dimethacrylate (produced by Shin-Nakamura Chemical Co., Ltd.), 0.5 g of LiBF$_4$ and 5.0 g of methyl ethyl ketone were mixed together. The thus obtained homogeneous solution was cast on a glass plate in dry inert glass atmosphere and the methyl ethyl ketone was evaporated off. The resultant layer was irradiated with electron beams in dry inert gas atmosphere to thereby polymerize and cure the di-2-methacryloxyethyl carbonate together with the diethylene glycol dimethacrylate. Thus, a polymeric solid electrolyte composed of the acrylic ester copolymer and the Group Ia metal salt (LiBF$_4$) was obtained.

Example 43

A polymeric solid electrolyte was produced in the same manner as in Example 42 except that propylene carbonate was employed in place of methyl ethyl ketone and that the propylene carbonate was not evaporated off.

Example 44

Synthesis of 2-Methoxyethoxyethoxyethyl Allyl Carbonate (Methoxyethoxyethoxyethyl Allyl Carbonate)

14.2 g (0.1 mol) of diallyl carbonate, 49.2 g (0.3 mol) of triethylene glycol monomethyl ester and 0.042 g (0.3 mmol) of potassium carbonate as a catalyst were charged into a 100 ml four-necked flask and reacted at 130° C. for 8 hr under reflux under agitation with removing formed allyl alcohol. After the completion of the reaction, potassium carbonate was removed by the use of a silica gel column and distillation was performed, thereby obtaining 2-methoxyethoxyethoxyethyl allyl carbonate (methoxyethoxyethoxyethyl allyl carbonate).

Figure 9:
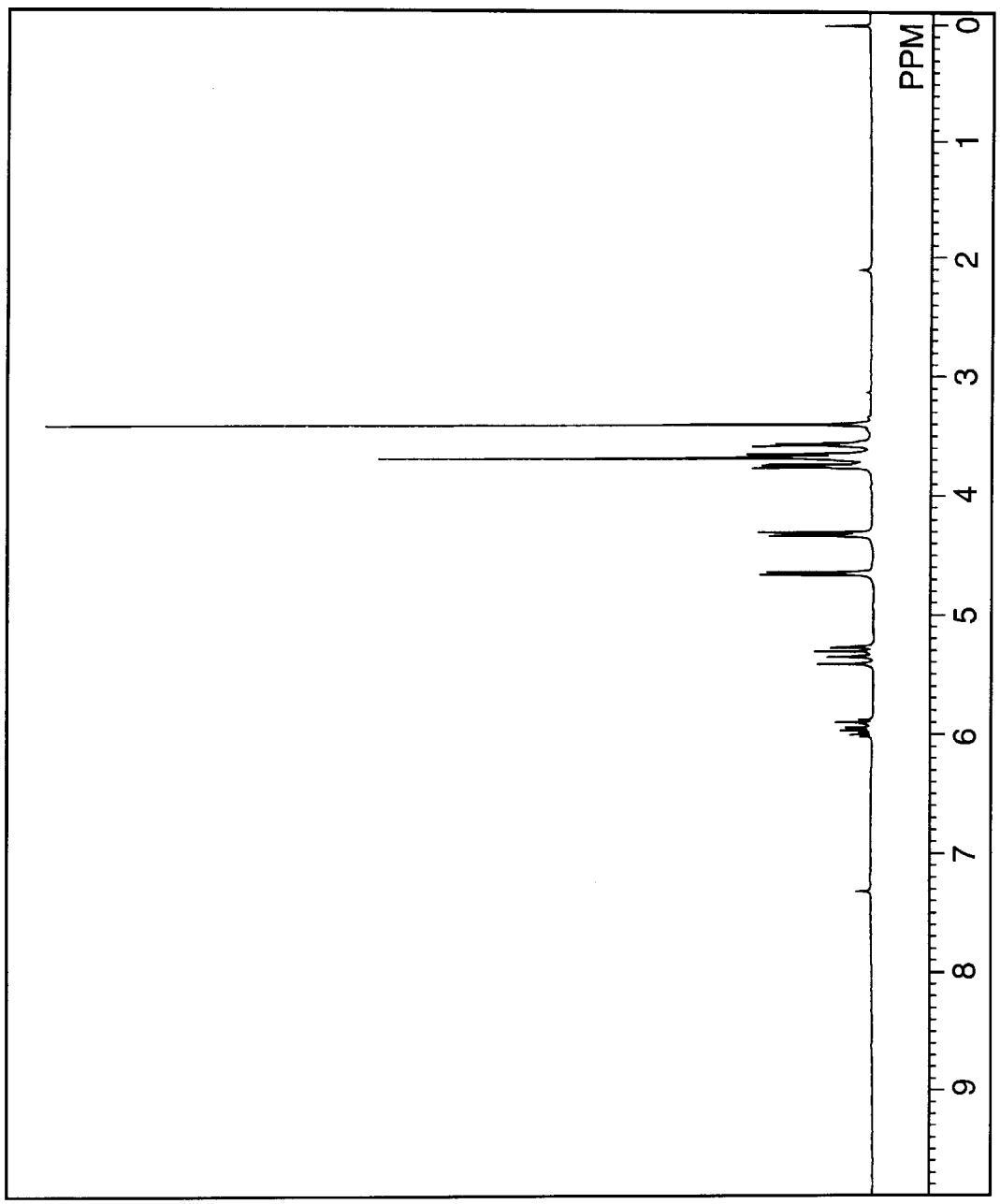
FIG. 9 is an NMR spectrum of 2-methoxyethoxyethoxyethyl allyl carbonate (methoxyethoxyethoxyethyl allyl carbonate) obtained in Example 44.
Figure 10:
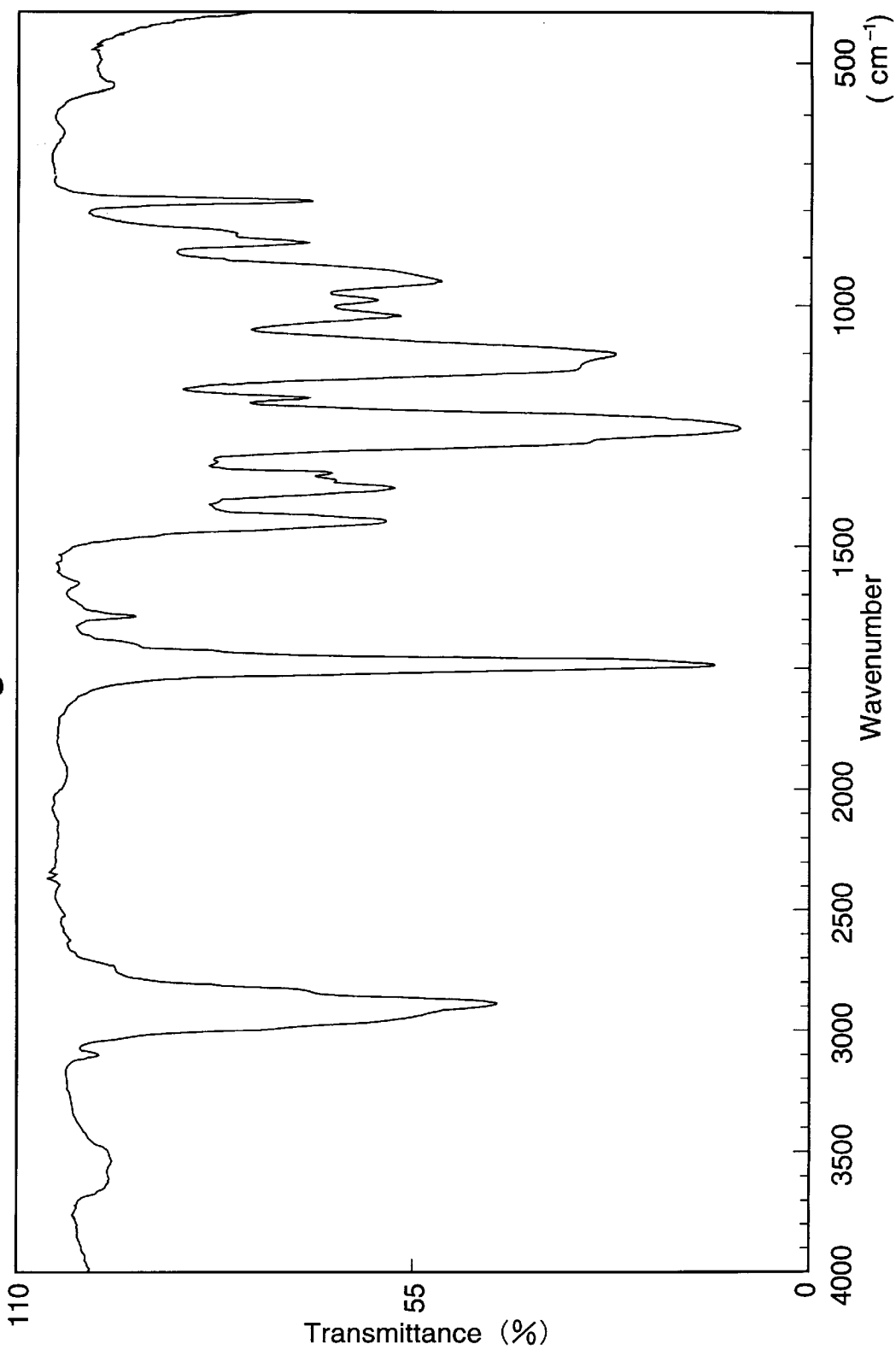
FIG. 10 is an IR spectrum of 2-methoxyethoxyethoxyethyl allyl carbonate (methoxyethoxyethoxyethyl allyl carbonate) obtained in Example 44.

Identification of the obtained 2-methoxyethoxyethoxyethyl allyl carbonate (methoxyethoxyethoxyethyl allyl carbonate) was conducted by $^1$H-NMR and IR. $^1$H-NMR and IR spectra are shown in FIGS. 9 and 10, respectively.

$^1$H-NMR (CDCl$_3$ solution, δ ppm): 3.39 (s, 3H, CH$_3$), 3.55–3.78 (m, 10H, CH$_2$), 4.30 (t, 2H, J=1.3 Hz, CH$_2$), 4.64 (d, 2H, 3.2 Hz, CH$_2$), 5.28 (d, 1H, J=4.0 Hz, CH), 5.38 (d, 1H, J=6.0 Hz, CH), 5.93 (m, 1H, CH).

IR (neat, cm$^{-1}$): 2880 (C═H), 1748 (C═O), 1649 (C═C), 1451, 1383, 1260, 1108, 872, 787.

Example 45

Synthesis of Methoxyethyl Allyloxyethyl Carbonate (2-Methoxyethyl 2-Allyloxyethyl Carbonate)

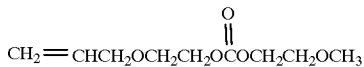

23.0 g (0.1 mol) of di-2-allyloxyethyl carbonate, 22.8 g (0.3 mol) of methoxyethanol and 0.042 g (0.3 mmol) of potassium carbonate as a catalyst were charged into a flask and reacted at 130° C. for 8 hr under reflux under agitation with removing formed allyloxyethanol. After the completion of the reaction, potassium carbonate was removed by the use of a silica gel column and distillation was performed, thereby obtaining methoxyethyl allyloxyethyl carbonate (2-methoxyethyl 2-allyloxyethyl carbonate).

Figure 11:
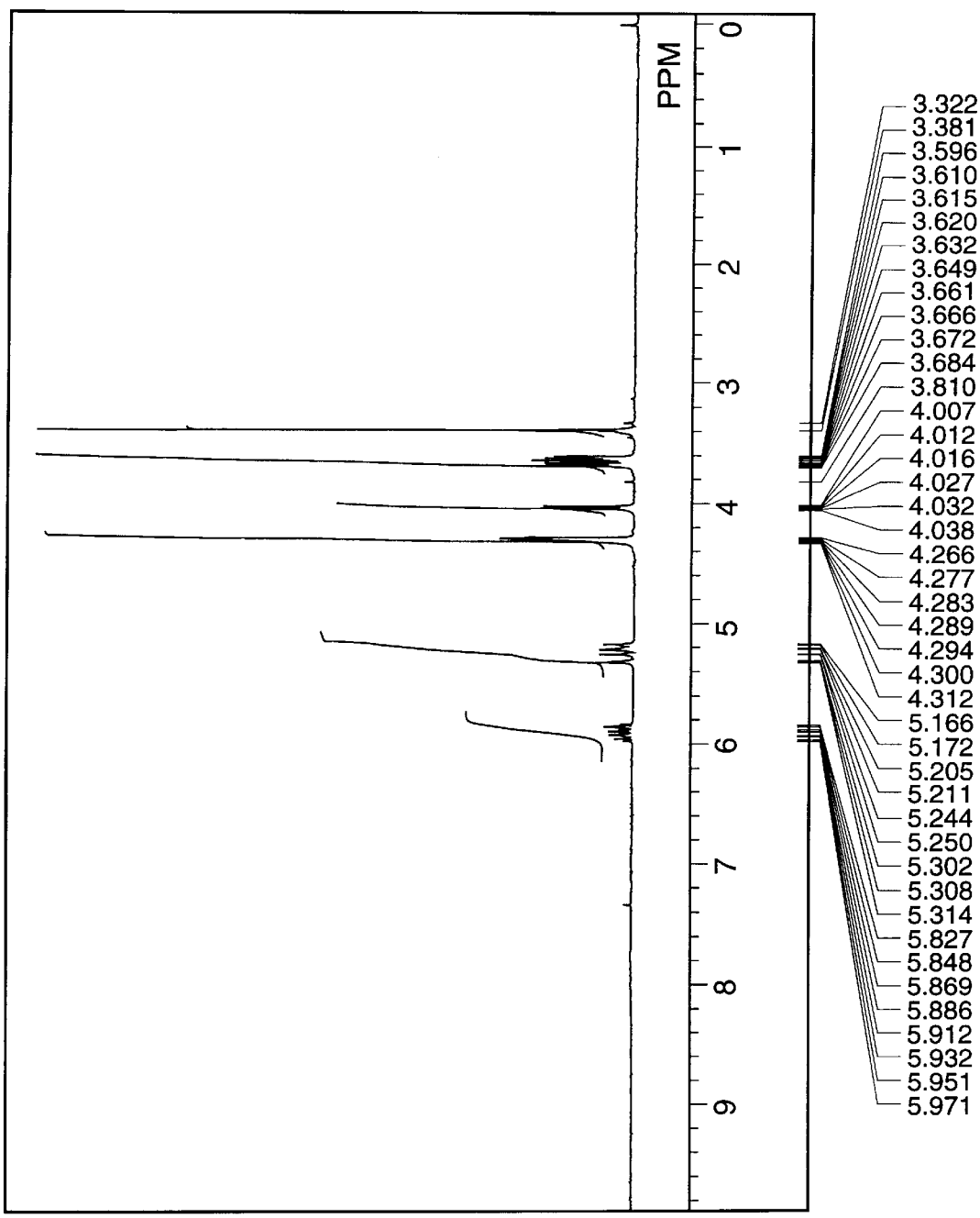
FIG. 11 is an NMR spectrum of methoxyethyl allyloxyethyl carbonate (2-methoxyethyl 2-allyloxyethyl carbonate) obtained in Example 45.
Figure 12:
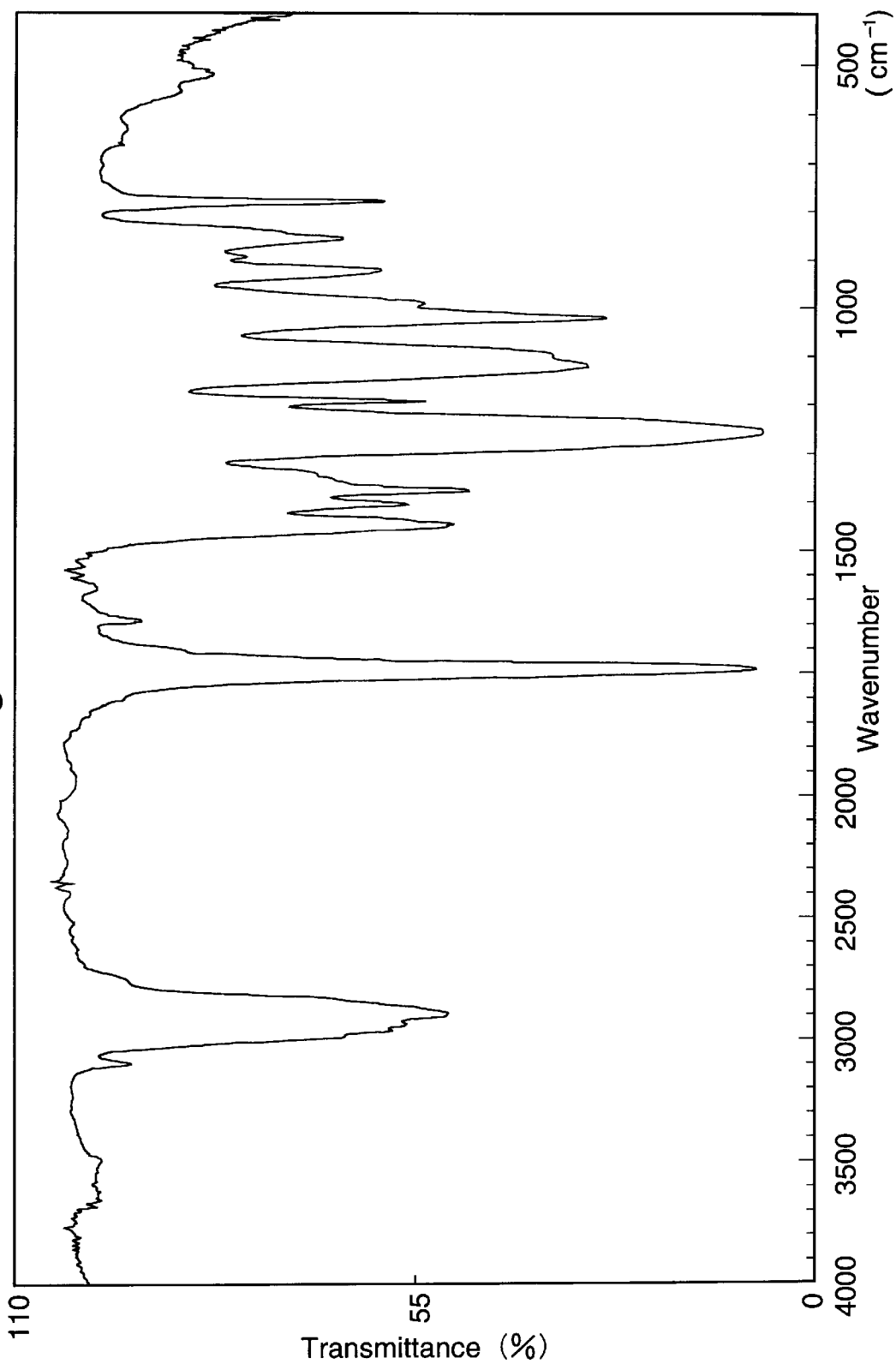
FIG. 12 is an IR spectrum of methoxyethyl allyloxyethyl carbonate (2-methoxyethyl 2-allyloxyethyl carbonate) obtained in Example 45.

Identification of the obtained methoxyethyl allyloxyethyl carbonate (2-methoxyethyl 2-allyloxyethyl carbonate) was conducted by $^1$H-NMR and IR. $^1$H-NMR and IR spectra are shown in FIGS. 11 and 12, respectively.

$^1$H-NMR (CDCl$_3$ solution, δ ppm): 3.22 (s, 3H, CH$_3$), 3.60–3.68 (m, 4H, CH$_2$), 4.01 (m, 2H, CH$_2$), 4.26–4.31 (m, 4H, CH$_2$), 5.20 (d, 1H, J=4 Hz, CH), 5.30 (d, 1H, J=6 Hz, CH), 5.89 (m, 1H, CH).

IR (neat, cm$^{-1}$): 2890 (C═H), 1749 (C═O), 1646 (C═O), 1451, 1263, 1127, 1029, 786.

Example 46

Preparation of Allyl Carbonate Polymer 2.48 g (0.01 mol) of 2-methylethoxyethoxyethyl allyl carbonate (methoxyethoxyethoxyethyl allyl carbonate) synthesized in Example 44, 41.6 μl Peroyl IPP50 (produced by Nippon Oil & Fats Co., Ltd.) were mixed together. The thus obtained homogeneous liquid was cast on a Teflon-coated glass plate and cured at 70° C. in dry inert gas atmosphere for 24 hr, thereby obtaining a transparent solid. A polymerization was confirmed by the extinction of absorption at 1640 cm$^{-1}$ ascribed to C═C vibration in an IR spectrum of the solid.

Example 47

Preparation of Allyl Carbonate Copolymer 1.24 g (0.005 mol) of 2-methoxyethoxyethoxyethyl allyl carbonate (methoxyethoxyethoxyethyl allyl carbonate) synthesized in Example 44, 0.58 g (0.005 mol) of methyl allyl carbonate and 41.6 μl of Peroyl IPP50 were mixed together. The thus obtained homogeneous liquid was cast on a Teflon-coated glass plate and cured at 80° C. in dry inert gas atmosphere for 24 hr, thereby obtaining a transparent solid. A polymerization was confirmed by the extinction of absorption at 1640 cm$^{-1}$ ascribed to C═C vibration in an IR spectrum of the solid.

Example 48

A copolymer was prepared in the same manner as in Example 47 except that diallyl carbonate was employed in place of methyl allyl carbonate. A polymerization was confirmed by the extinction of absorption at 1640 cm$^{-1}$ ascribed to C═C vibration in an IR spectrum of the copolymer, as in Example 47.

Figure 13:
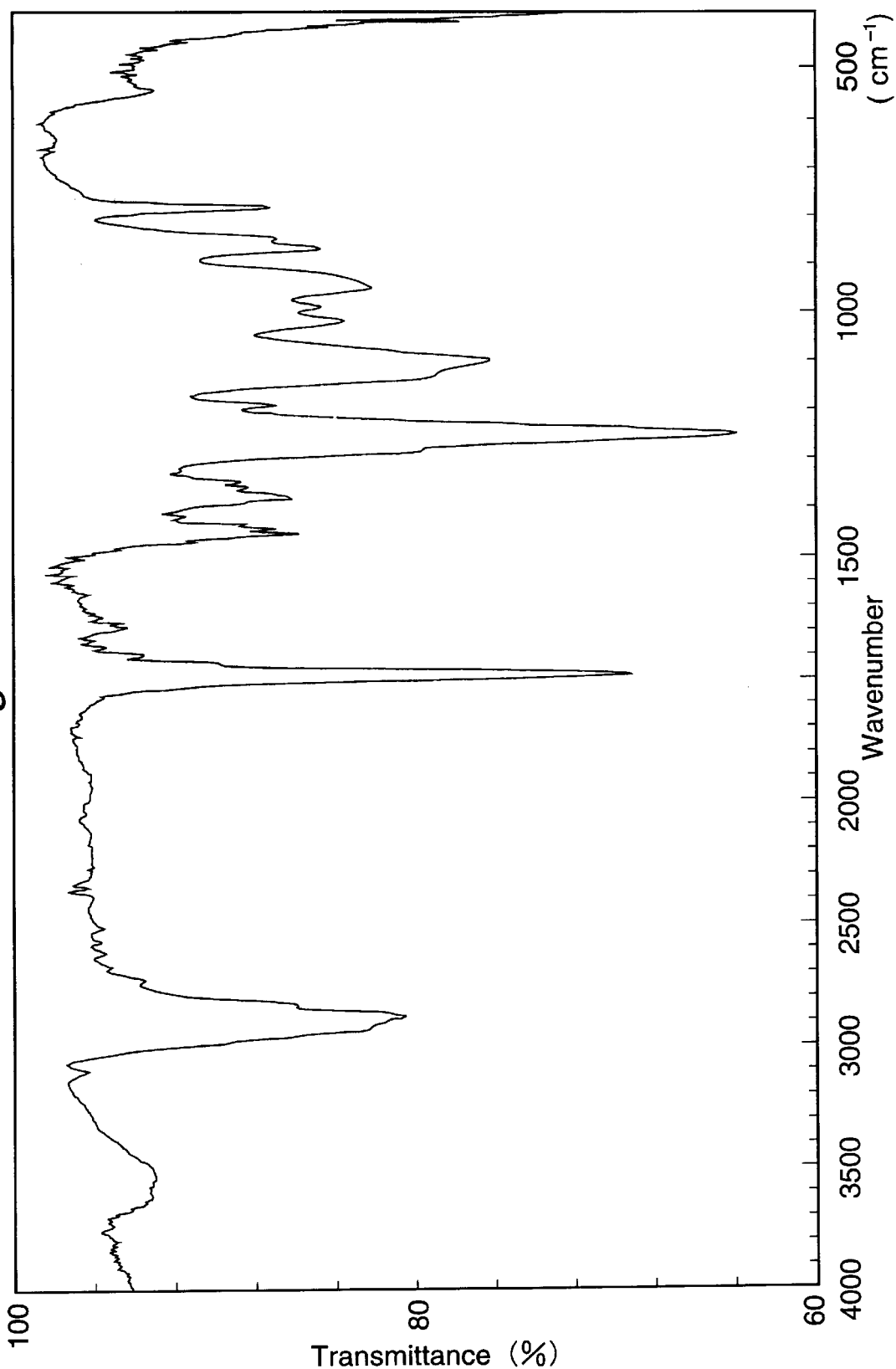
FIG. 13 is an IR spectrum of a copolymer of 2-methoxyethoxyethoxyethyl allyl carbonate (methoxyethoxyethoxyethyl allyl carbonate) and diallyl carbonate obtained in Example 48.

The obtained IR spectrum is shown in FIG. 13.

Example 49

Production of Polymeric Solid Electrolyte and Measurement of Ionic Conductivity

50% by weight of a 5:5 (mol:mol) monomer mixture of 2-methoxyethoxyethoxyethyl allyl carbonate (methoxyethoxyethoxyethyl allyl carbonate) synthesized in Example 44 and diallyl carbonate, 50% by weight of propylene carbonate, 1 mol %, based on the carbonate units, of Group Ia metal salt of the formula LiN(CF$_3$SO$_2$)$_2$ and 1 mol %, based on the monomers, of Peroyl IPP50 were mixed together. The thus obtained homogeneous liquid was cast on a Teflon-coated glass plate and cured at 80° C. in dry inert gas atmosphere for 24 hr, thereby obtaining a polymeric solid electrolyte composed of the acrylic ester polymer and the Group Ia metal salt. A polymerization was confirmed by the extinction of absorption at 1640 cm$^{-1}$ ascribed to C═C vibration in an IR spectrum of the electrolyte.

The ionic conductivity of the obtained thin-film polymeric solid electrolyte was measured in the same manner as in Example 12. The results are given in Table 3.

TABLE 3

Measurement of Ionic Conductivity
(measured at 25° C.)

| Example | Conductivity (S/cm) |
| --- | --- |
| 49 | $9.5 \times 10^{-4}$ |

Example 50

Production of Polymeric Solid Electrolyte 5.0 g of 2-methoxyethyl allyl carbonate (methoxyethoxyethoxyethyl allyl carbonate) produced in Example 44, 0.5 g of LiBF$_4$, 5.0 g of dimethyl carbonate and 0.2 g of diisopropyl peroxydicarbonate as a polymerization catalyst were mixed together. The thus obtained homogeneous solution was cast on a glass plate in dry inert gas atmosphere and the dimethyl carbonate was evaporated off. The resultant layer was heated at 80° C., thereby obtaining a polymeric electrolyte composed of the 2-methoxyethyl allyl carbonate (2-methoxyethoxyethoxyethyl allyl carbonate) polymer and the Group Ia metal salt.

Example 51

A polymeric solid electrolyte was produced in the same manner as in Example 50 except that propylene carbonate was employed in place of dimethyl carbonate and that the propylene carbonate was not evaporated off.

Example 52

A polymeric solid lectrolyte was produced in the same manner as in Example 50 except that LiClO$_4$ was employed in place of LiBF$_4$.

Example 53

Synthesis of Diethylene Glycol Diallyl Dicarbonate (di(2-allyloxycarbonyloxyethyl)ether)

28.4 g (0.2 mol) of diallyl carbonate, 10.6 g (0.1 mol) of diethylene glycol and 0.042 g (0.3 mmol) of potassium carbonate as a catalyst were charged into a 100 ml four-necked flask and reacted at 130° C. for 8 hr under reflux under agitation with removing formed allyl alcohol. After the completion of the reaction, potassium carbonate was removed by the use of the silica gel column and distillation was performed, thereby obtaining diethylene glycol diallyl dicarbonate (di-(2-allyloxycarbonyloxyethyl)ether).

Figure 14:
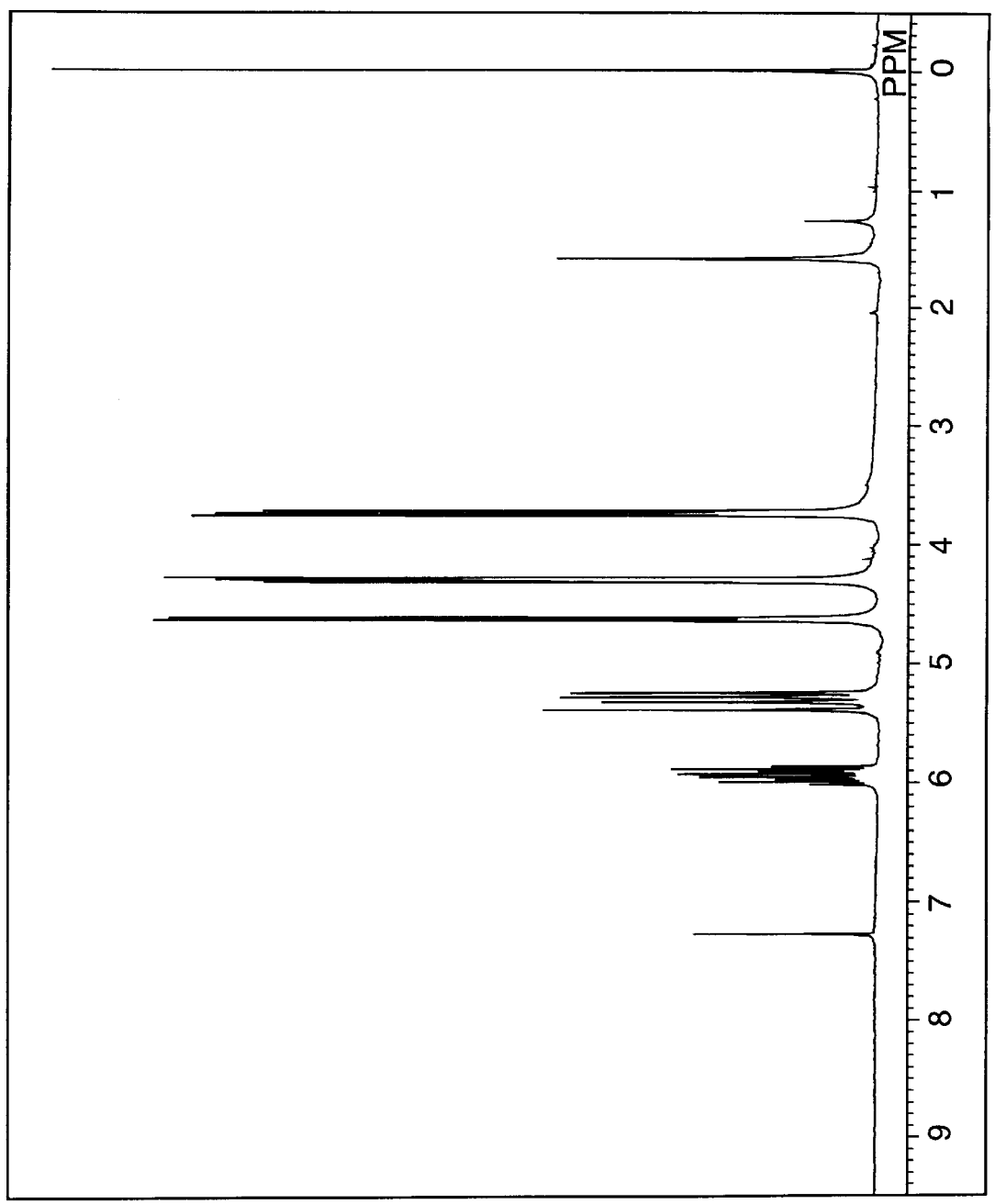
FIG. 14 is an NMR spectrum of diethylene glycol diallyl dicarbonate (di(2-allyloxycarbonyloxyethyl) ether) obtained in Example 53.
Figure 15:
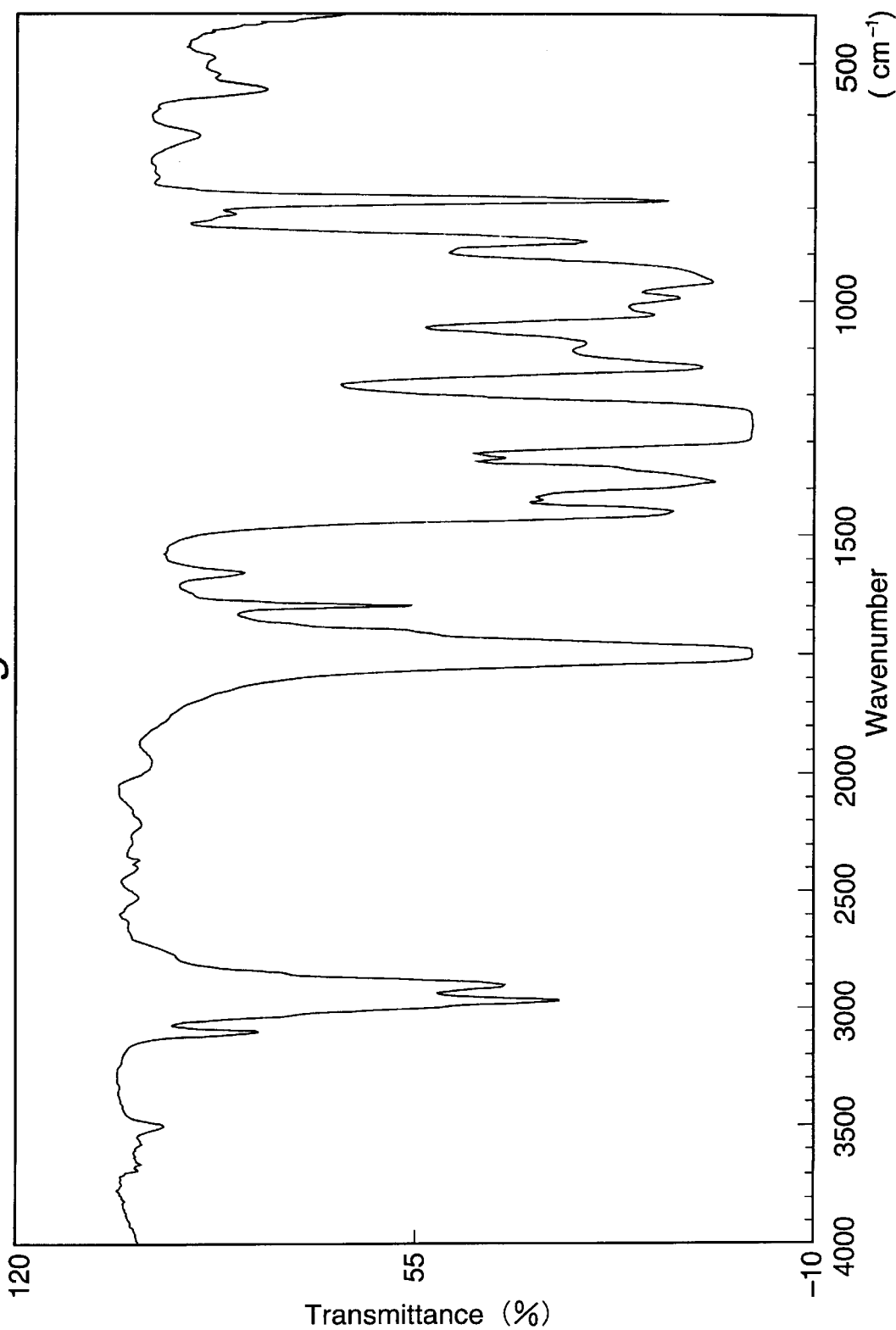
FIG. 15 is an IR spectrum of diethylene glycol diallyl dicarbonate (di(2-allyloxycarbonyloxyethyl) ether) obtained in Example 53.

Identification of the obtained diethylene glycol diallyl dicarbonate (di(2-allyloxycarbonyloxyethyl)ether) was conducted by $^1$H-NMR and IR. $^1$H-NMR and IR spectra are shown in FIGS. 14 and 15, respectively.

$^1$H-NMR (CDCl$_3$ solution, δ ppm): 3.73 (m, 4H, CH$_2$), 4.30 (m, 4H, CH$_2$), 4.62 (m, 4H, CH$_2$), 5.26 (q, 2H, J=8.1 Hz, CH), 5.33 (q, 2H, J=13.5 Hz, CH), 5.94 (m, 2H, CH$_2$).

IR (neat, cm$^{-1}$): 2958 (C=H), 1750 (C=O), 1649 (C=C), 1451, 1387, 1280, 1143, 876, 786.

Example 54

Preparation of Allyl Carbonate Polymer 2.88 g (0.01 mol) of diethylene glycol diallyl dicarbonate (di(2-allyloxycarbonyloxyethyl)ethyl) produced in Example 53 and 41.6 μl of Peroyl IPP50 (produced by Nippon Oil & Fats Co., Ltd.) were mixed together. The thus obtained homogeneous liquid was cast on a Teflon-coated glass plate and cured at 80° C. in dry inert gas atmosphere for 24 hr, thereby obtaining a transparent solid. A polymerization was confirmed by the extinction of absorption at 1640 cm$^{-1}$ ascribed to C=C vibration in an IR spectrum of the solid.

Example 55

Preparation of Allyl Carbonate Copolymer 1.44 g (0.005 mol) of diethylene glycol diallyl dicarbonate (di(2-allyloxycarbonyloxyethyl)ether) produced in Example 53, 1.24 g (0.005 mol) of 2-methoxyethoxyethoxyethyl allyl carbonate (methoxyethoxyethoxyethyl allyl carbonate) produced in Example 44 and 41.6 μl of Peroyl IPP50 were mixed together. The thus obtained homogeneous liquid was cast on a Teflon-coated glass plate and cured at 80° C. in dry inert gas atmosphere for 24 hr, thereby obtaining a transparent solid. A polymerization was confirmed by the extinction of absorption at 1640 cm$^{-1}$ ascribed to C=C vibration in an IR spectrum of the solid.

Example 56

A copolymer was prepared in the same manner as in Example 55 except that methyl allyl carbonate was employed in place of 2-methoxyethoxyethoxyethyl allyl carbonate (methoxyethoxyethoxyethyl allyl carbonate).

Example 57

A copolymer was prepared in the same manner as in Example 55 except that diallyl carbonate was employed in place of 2-methoxyethoxyethoxyethyl allyl carbonate (methoxyethoxyethoxyethyl allyl carbonate). A polymerization was confirmed by the extinction of absorption at 1640 cm$^{-1}$ ascribed to C=C vibration in an IR spectrum of the copolymer, as in Example 55.

Figure 16:
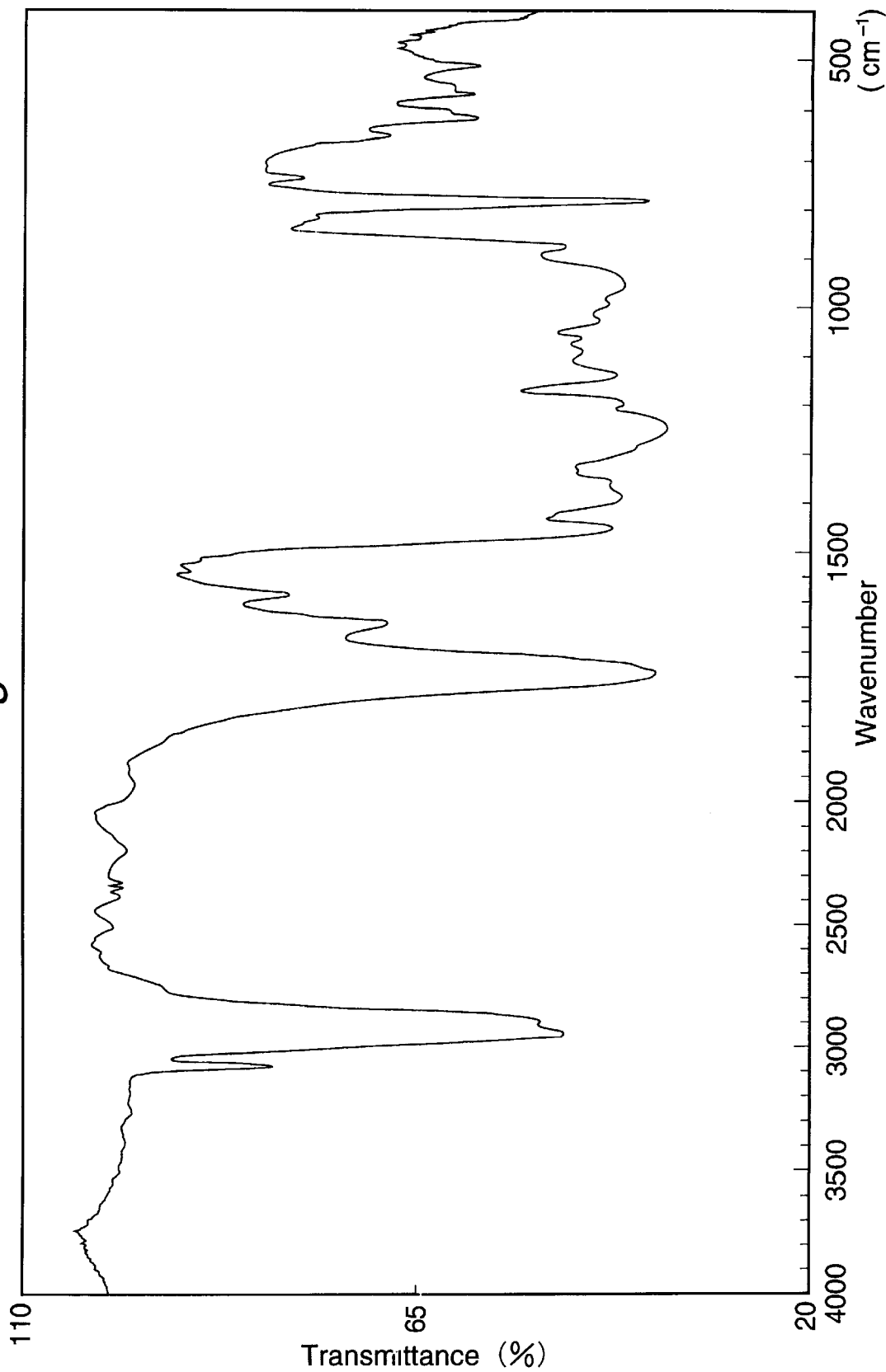
FIG. 16 is an IR spectrum of a copolymer of diethylene glycol diallyl dicarbonate (di(2-allyloxycarbonyloxyethyl) ether) and diallyl carbonate obtained in Example 57.

The obtained IR spectrum is shown in FIG. 16.

Example 58

Production of Polymeric Solid Electrolyte and Measurement of Ionic Conductivity

Diethylene glycol diallyl dicarbonate (di(2-allyloxycarbonyloxyethyl)ether) produced in Example 53, 2 mol %, based on the carbonate units, of Group Ia metal salt of the formula LiN(CF$_3$SO$_2$)$_2$ and 1 mol %, based on the monomer, of Peroyl IPP50 were mixed together. The thus obtained homogeneous liquid was cast on a Teflon-coated glass plate and cured at 80° C. in dry inert gas atmosphere for 24 hr, thereby obtaining a polymeric solid electrolyte composed of the allyl carbonate polymer and the Group Ia metal salt. A polymerization was confirmed by the extinction of absorption at 1640 cm$^{-1}$ ascribed to C=C vibration in an IR spectrum of the electrolyte.

The ionic conductivity of the obtained thin-film polymeric solid electrolyte was measured in the same manner as in Example 12. The results are given in Table 4.

Example 59

A polymeric solid electrolyte was produced in the same manner as in Example 58 except that a mixture of 70% by weight of diethylene glycol diallyl dicarbonate (di(2-allyloxycarbonyloxyethyl)ether) and 30% by weight of propylene carbonate was employed.

The ionic conductivity of the obtained thin-film polymeric solid electrolyte was measured in the same manner as in Example 12. The results are given in Table 4.

Example 60

A 5:5 (mol:mol) monomer mixture of diethylene glycol diallyl dicarbonate (di(2-allyloxycarbonyloxyethyl)ether) produced in Example 53 and 2-methoxyethoxyethoxyethyl allyl carbonate (methoxyethoxyethoxyethyl allyl carbonate) produced in Example 44, 2 mol %, based on the carbonate units, of Group Ia metal salt of the formula $LiN(CF_3SO_2)_2$ and 1 mol %, based on the monomers, of Peroyl IPP50 were mixed together. The thus obtained homogeneous liquid was cast on a Teflon-coated glass plate and cured at 80° C. in dry inert gas atmosphere for 24 hr, thereby obtaining a thin-film polymeric solid electrolyte composed of the acrylic ester polymer and the Group Ia metal salt. A polymerization was confirmed by the extinction of absorption at 1640 $cm^{-1}$ ascribed to C=C vibration in an IR spectrum of the electrolyte.

The ionic conductivity of the obtained thin-film polymeric solid electrolyte was measured in the same manner as in Example 12. The results are given in Table 4.

Example 61

A polymeric solid electrolyte was produced in the same manner as in Example 60 except that methyl allyl carbonate was employed in place of 2-methoxyethoxyethoxyethyl allyl carbonate (methoxyethoxyethoxyethyl allyl carbonate).

The ionic conductivity of the obtained thin-film polymeric solid electrolyte was measured in the same manner as in Example 12. The results are given in Table 4.

Example 62

A polymeric solid electrolyte was produced in the same manner as in Example 60 except that diallyl carbonate was employed in place of 2-methoxyethoxyethoxyethyl allyl carbonate (methoxyethoxyethoxyethyl allyl carbonate).

TABLE 4

| Measurement of Ionic Conductivity (measured at 25° C.) | |
| --- | --- |
| Example | Conductivity (S/cm) |
| 58 | $1.9 \times 10^{-6}$ |
| 59 | $1.5 \times 10^{-4}$ |
| 60 | $2.2 \times 10^{-4}$ |
| 61 | $2.7 \times 10^{-6}$ |
| 62 | $2.1 \times 10^{-6}$ |

Example 63

Synthesis of Diethylene Glycol Diallyl Dicarbonate (di(2-allyloxycarbonyloxyethyl)ether)

Diethylene glycol diallyl dicarbonate (di(2-allyloxycarbonyloxyethyl)ether)was synthesized in the same manner as in Example 53 except that the amount of diallyl carbonate was varied to 14.2 g (0.1 mol).

Example 64

Production of Polymeric Solid Electrolyte 5.0 g of diethylene glycol diallyl dicarbonate (di(2-allyloxycarbonyloxyethyl)ether) produced in Example 53 or 63, 0.5 g of $LiBF_4$, 5.0 g of dimethyl carbonate and 0.2 g of diisopropyl peroxydicarbonate as a polymerization catalyst were mixed together. The thus obtained homogeneous solution was cast on a glass plate in dry inert gas atmosphere and the dimethyl carbonate was evaporated off. The resultant layer was heated at 80° C. to thereby polymerize the diethylene glycol diallyl dicarbonate (di(2-allyloxycarbonyloxyethyl)ether) and cure the resulting polymer. Thus, a polymeric solid electrolyte composed of the diethylene glycol diallyl dicarbonate polymer (di(2-allyloxycarbonyloxyethyl)ether) and the Group Ia metal salt was obtained.

Example 65

A polymeric solid electrolyte was produced in the same manner as in Example 64 except that propylene carbonate was employed in place of dimethyl carbonate and that the propylene carbonate was not evaporated off.

Example 66

A polymeric solid electrolyte was produced in the same manner as in Example 64 except that $LiClO_4$ was employed in place of $LiBF_4$.

Example 67

Synthesis of Allyl Methyl Carbonate 422 g (7.27 mol) of allyl alcohol, 2120 g (23.6 mol) of dimethyl carbonate and 1.0 g (7.3 mmol) of potassium carbonate as a catalyst were charged into a 5 lit. four-necked flask and reacted at 90° C. for 10 hr under reflux under agitation with removing formed methanol. After the completion of the reaction, potassium carbonate was removed by the use of a short column of silica gel, and then distillation was performed, thereby obtaining allyl methyl carbonate.

Synthesis of Trifunctional Compound 23 g of glycerol, 2.5 g of potassium hydroxide and 1200 g of ethylene oxide were charged into an autoclave and reacted at 130° C. for 7 hr. Neutralization and desalting were conducted, thereby obtaining a trifunctional polyethylene oxide of about 6000 in molecular weight having a hydroxyl group at its terminal. 2 g of concentrated sulfuric acid and toluene were added to 200 g of this trifunctional polyethylene oxide and 15 g of methacrylic acid and a dehydrating condensation was carried out with azeotropically distilling water off under reflux. Thus, trifunctional compound of the above general formula (VII) wherein $R^{22}$, $R^{23}$ and $R^{24}$ represent hydrogen atoms and $R^{25}$, $R^{26}$ and $R^{27}$ represent methyl groups was obtained.

Production of Polymeric Solid Electrolyte 5.0 g of allyl methyl carbonate and 2.0 g of trifunctional compound synthesized above, 5.0 g of $LiBF_4$, 5.0 g of dimethyl carbonate and 0.2 g of diisopropyl peroxydicarbonate were mixed together. The thus obtained homogeneous solution was cast on a glass plate in dry inert gas atmosphere and the dimethyl carbonate was evaporated off. The resultant layer was heated at 80° C. to thereby copolymerize the allyl methyl carbonate and trifunctional compound and cure the resulting polymer. Thus, a polymeric solid electrolyte composed of the allyl carbonate copolymer and the Group Ia metal salt ($LiBF_4$) was obtained.

Example 68

A polymeric solid electrolyte was produced in the same manner as in Example 67 except that propylene carbonate was employed in place of dimethyl carbonate and that the propylene carbonate was not evaporated off.

Example 69

A polymeric solid electrolyte was produced in the same manner as in Example 67 except that propylene carbonate was employed in place of dimethyl carbonate, that $LiClO_4$ was employed in place of $LiBF_4$ and that the propylene carbonate was not evaporated off.

Example 70

Synthesis of Diallyl Carbonate 842 g (14.5 mol) of allyl alcohol, 1306 g 14.5 mol) of dimethyl carbonate and 1.0 g (7.3 mmol) of potassium carbonate as a catalyst were charged into a 3 lit. four-necked flash and reacted at 90° C. for 10 hr under reflux under agitation with removing formed methanol. After the completion of the reaction, potassium carbonate was removed by the use of a short column of silica gel, and then distillation was performed, thereby obtaining diallyl carbonate.

Production of Polymeric Solid Electrolyte 5.0 g of diallyl carbonate synthesized above, 2.0 g of trifunctional compound synthesized in Example 67, 5.0 g of $LiBF_4$, 5.0 g of dimethyl carbonate and 0.2 g of diisopropyl peroxydicarbonate were mixed together. The thus obtained homogeneous solution was cast on a glass plate in dry inert gas atmosphere and the dimethyl carbonate was evaporated off. The resultant layer was heated at 80° C. to thereby copolymerize the diallyl carbonate and trifunctional compound and cure the resulting polymer. Thus, a polymeric solid electrolyte composed of the allyl carbonate copolymer and the Group Ia metal salt ($LiBF_4$) was obtained.

Example 71

A polymeric solid electrolyte was produced in the same manner as in Example 70 except that propylene carbonate was employed in place of dimethyl carbonate and that the propylene carbonate was not evaporated off.

Example 72

A polymeric solid electrolyte was produced in the same manner as in Example 70 except that propylene carbonate was employed in place of dimethyl carbonate, that $LiClO_4$ was employed in place of $LiBF_4$ and that the propylene carbonate was not evaporated off.

Example 73

Synthesis of Allyl Carbonate Copolymer

In a dry argon atmosphere, 1.0 g (3.6 mmol) of the di(2-allyloxycarbonyloxyethyl) ether (DEAC) prepared in Example 63, 11.0 g (93.6 mmol, [MAC]/[DEAC]=26) of the allylmethyl carbonate (MAC) prepared in Example 67 and 1.4 g (6.9 mmol, 7.1% by mol based on the total amount of DEAC and MAC) of diisopropyl peroxydicarbonate (IPP) were homogeneously mixed. The resulting mixed solution was injected into a laminate made up of two glass plates coated with Teflon sheets and a silicone rubber spacer interposed between the two glass plates. Then, the laminate was heated at 70° C. for 13 hours to copolymerize DEAC and MAC and thereby cure the resulting copolymer. Thus, an allyl carbonate copolymer was synthesized.

The gel fraction and the glass transition temperature of the resulting allyl carbonate copolymer were measured. The result on the gel fraction is set forth in Table 5, and the result on the glass transition temperature is set forth in Table 6.

The properties of the allyl carbonate copolymers, the polymeric solid electrolytes and the gelled polymeric solid electrolytes obtained in the examples were measured by the following methods.

Gel Fraction

The allyl carbonate copolymer was impregnated with benzene for 2 days. The weights of the allyl carbonate copolymer before and after the impregnation were measured, and the gel fraction was calculated by the following equation.

$$\text{Gel fraction } (\%) = \frac{\text{Weight after impregnation with benzene}}{\text{Weight before impregnation with benzene}} \times 100$$

Glass Transition Temperature

The allyl carbonate copolymer was heated to dryness at 70° C. under vacuum and enclosed in a sealed aluminum pan. The sealed pan was set on a differential scanning calorimeter (DSC-220C, manufactured by SEIKO) and heated at a rate of 10° C./min. to measure changes in heat capacity at –100 to 100° C. The intermediate point of the changes in the heat capacity was taken as a glass transition temperature.

Ionic Conductivity

In an argon atmosphere, the polymeric solid electrolyte was punched out with a punch having diameter of 1.3 cm to prepare a specimen. The specimen was interposed between stainless steel electrodes and enclosed in a closed impedance measuring cell. The measuring cell was fixed to a constant temperature bath (Yashima BX-10) having been subjected to temperature setting. Then, the impedance was measured (alternating voltage: 500 mV) by means of an impedance analyzer (YHP4192A) to determine ionic conductivity.

Example 74

Synthesis of Allyl Carbonate Copolymer

An allyl carbonate copolymer was synthesized in the same manner as in Example 73, except that the amount of IPP was varied to 0.7 g (3.4 mmol, 3.5% by mol based on the total amount of DEAC and MAC).

The gel fraction of the resulting allyl carbonate copolymer was measured. The result is set forth in Table 5.

Example 75

Synthesis of Allyl Carbonate Copolymer

An allyl carbonate copolymer was synthesized in the same manner as in Example 73, except that the amount of IPP was varied to 0.5 g (2.4 mmol, 2.4% by mol based on the total amount of DEAC and MAC).

The gel fraction of the resulting allyl carbonate copolymer was measured. The result is set forth in Table 5.

Example 76

Synthesis of Allyl Carbonate Copolymer

An allyl carbonate copolymer was synthesized in the same manner as in Example 73, except that the amount of IPP was varied to 0.4 g (1.8 mmol, 1.8% by mol based on the total amount of DEAC and MAC).

The gel fraction of the resulting allyl carbonate copolymer was measured. The result is set forth in Table 5.

Example 77

Synthesis of Allyl Carbonate Copolymer

An allyl carbonate copolymer was synthesized in the same manner as in Example 73, except that the amount of IPP was varied to 0.34 g (1.4 mmol, 1.4% by mol based on the total amount of DEAC and MAC).

The gel fraction of the resulting allyl carbonate copolymer was measured. The result is set forth in Table 5.

Example 78

Synthesis of Allyl Carbonate Copolymer

An allyl carbonate copolymer was synthesized in the same manner as in Example 73, except that the amount of IPP was varied to 0.2 g (1.0 mmol, 1.0% by mol based on the total amount of DEAC and MAC).

The gel fraction of the resulting allyl carbonate copolymer was measured. The result is set forth in Table 5.

Example 79

Synthesis of Allyl Carbonate Copolymer

An allyl carbonate copolymer was synthesized in the same manner as in Example 73, except that the amount of MAC was varied to 12.9 g (111.6 mmol, [MAC]/[DEAC]= 31) and the amount of IPP was varied to 1.7 g (8.2 mmol, 7.1% by mol based on the total amount of DEAC and MAC).

The glass transition temperature of the resulting allyl carbonate copolymer was measured. The result is set forth in Table 6.

Example 80

Synthesis of Allyl Carbonate Copolymer

An allyl carbonate copolymer was synthesized in the same manner as in Example 73, except that the amount of MAC was varied to 11.3 g (97.2 mmol, [MAC]/[DEAC]= 27) and the amount of IPP was varied to 1.5 g (7.2 mmol, 7.1% by mol based on the total amount of DEAC and MAC).

The glass transition temperature of the resulting allyl carbonate copolymer was measured. The result is set forth in Table 6.

Example 81

Synthesis of Allyl Carbonate Copolymer

An allyl carbonate copolymer was synthesized in the same manner as in Example 73, except that the amount of MAC was varied to 10.0 g (86.4 mmol, [MAC]/[DEAC]= 24) and the amount of IPP was varied to 1.3 g (6.4 mmol, 7.1% by mol based on the total amount of DEAC and MAC).

The glass transition temperature of the resulting allyl carbonate copolymer was measured. The result is set forth in Table 6.

Example 82

Synthesis of Allyl Carbonate Copolymer

An allyl carbonate copolymer was synthesized in the same manner as in Example 73, except that the amount of MAC was varied to 8.8 g (75.6 mmol, [MAC]/[DEAC]=21) and the amount of IPP was varied to 1.2 g (5.6 mmol, 7.1% by mol based on the total amount of DEAC and MAC).

The glass transition temperature of the resulting allyl carbonate copolymer measured. The result is set forth in Table 6.

Example 83

Synthesis of Allyl Carbonate Copolymer

An allyl carbonate copolymer was synthesized in the same manner as in Example 73, except that the amount of MAC was varied to 4.2 g (36.0 mmol, [MAC]/[DEAC]=10) and the amount of IPP was varied to 0.6 g (2.8 mmol, 7.1% by mol based on the total amount of DEAC and MAC).

The glass transition temperature of the resulting allyl carbonate copolymer was measured. The result is set forth in Table 6.

Example 84

Synthesis of Allyl Carbonate Copolymer

An allyl carbonate copolymer was synthesized in the same manner as in Example 73, except that the amount of MAC was varied to 2.5 g (21.6 mmol, [MAC]/[DEAC]=6) and the amount of IPP was varied to 0.4 g (1.8 mmol, 7.1% by mol based on the total amount of DEAC and MAC).

The glass transition temperature of the resulting allyl carbonate copolymer was measured. The result is set forth in Table 6.

Example 85

Synthesis of allyl carbonate copolymer

An allyl carbonate copolymer was synthesized in the same manner as in Example 73, except that the amount of MAC was varied to 1.7 g (14.4 mmol, [MAC]/[DEAC]=4) and the amount of IPP was varied to 0.3 g (1.3 mmol, 7.1% by mol based on the total amount of DEAC and MAC).

The glass transition temperature of the resulting allyl carbonate copolymer was measured. The result is set forth in Table 6.

Example 86

Synthesis of Allyl Carbonate Copolymer

An allyl carbonate copolymer was synthesized in the same manner as in Example 73, except that the amount of MAC was varied to 0.8 g (7.2 mmol, [MAC]/[DEAC]=2) and the amount of IPP was varied to 0.2 g (0.8 mmol, 7.1% by mol based on the total amount of DEAC and MAC).

The glass transition temperature of the resulting allyl carbonate copolymer was measured. The result is set forth in Table 6.

Example 87

Preparation of Polymeric Solid Electrolyte

A polymeric solid electrolyte composed of an allyl carbonate copolymer and a Group Ia metal salt was prepared in the same manner as in Example 73, except that 0.6 g (2.0 mmol, [LiN(CF$_3$SO$_2$)$_2$]/{[—OCOO—] in DEAC and MAC}=0.02) of LiN(CF$_3$SO$_2$)$_2$ was added to the mixed solution.

The ionic conductivities of the resulting polymeric solid electrolyte at 80° C. and 100° C. were measured. The results are set forth in Table 7.

Example 88

Preparation of Polymeric Solid Electrolyte

A polymeric solid electrolyte was prepared in the same manner as in Example 87, except that the amount of MAC was varied to 11.3 g (97.2 mmol, [MAC]/[DEAC]=27), the amount of IPP was varied to 1.5 g (7.2 mmol, 7.1% by mol based on the total amount of DEAC and MAC) and the amount of $LiN(CF_3SO_2)_2$ was varied to 0.6 g (2.1 mmol, $[LiN(CF_3SO_2)_2]/\{[—OCOO—]$ in DEAC and MAC$\}$= 0.02).

The ionic conductivities of the resulting polymeric solid electrolyte at 80° C. and 100° C. were measured. The results are set forth in Table 7.

Example 89

Preparation of Polymeric Solid Electrolyte

A polymeric solid electrolyte was prepared in the same manner as in Example 87, except that the amount of MAC was varied to 11.7 g (100.8 mol, [MAC]/[DEAC]=28), the amount of IPP was varied to 1.5 g (7.4 mmol, 7.1% by mol based on the total amount of DEAC and MAC) and the amount of $LiN(CF_3SO_2)_2$ was varied to 0.6 g (2.2 mmol, $[LiN(CF_3SO_2)_2]/\{[—OCOO—]$ in DEAC and MAC$\}$= 0.02).

The ionic conductivities of the resulting polymeric solid electrolyte at 80° C. and 100° C. were measured. The results are set forth in Table 7.

Example 90

Preparation of Polymeric Solid Electrolyte

A polymeric solid electrolyte was prepared in the same manner as in Example 89, except that the amount of $LiN(CF_3SO_2)_2$ was varied to 2.7 g (9.7 mmol, $[LiN(CF_3SO_2)_2]/\{[—OCOO—]$ in DEAC and MAC$\}$=0.09).

The ionic conductivities of the resulting polymeric solid electrolyte at 80° C. and 100° C. were measured. The results are set forth in Table 7.

Example 91

Preparation of Polymeric Solid Electrolyte

A polymeric solid electrolyte was prepared in the same manner as in Example 87, except that the amount of MAC was varied to 12.9 g (111.6 mmol, [MAC]/[DEAC]=31), the amount of IPP was varied to 1.7 g (8.2 mmol, 7.1% by mol based on the total amount of DEAC and MAC) and the amount of $LiN(CF_3SO_2)_2$ was varied to 0.7 g (2.4 mmol, $[LiN(CF_3SO_2)_2]/\{[—OCOO—]$ in DEAC and MAC$\}$= 0.02).

The ionic conductivities of the resulting polymeric solid electrolyte at 80° C. and 100° C. were measured. The results are set forth in Table 7.

Example 92

Preparation of Polymeric solid electrolyte

A polymeric solid electrolyte was prepared in the same manner as in Example 87, except that the amount of MAC was varied to 13.4 g (115.2 mmol, [MAC]/[DEAC]=32), the amount of IPP was varied to 1.7 g (8.4 mmol, 7.1% by mol based on the total amount of DEAC and MAC) and the amount of $LiN(CF_3SO_2)_2$ was varied to 0.7 g (2.4 mmol, $[LiN(CF_3SO_2)_2]/\{[—OCOO—]$ in DEAC and MAC$\}$= 0.02).

The ionic conductivities of the resulting polymeric solid electrolyte at 80° C. and 100° C. were measured. The results are set forth in Table 7.

Example 93

Preparation of Polymeric Solid Electrolyte

A polymeric solid electrolyte was prepared in the same manner as in Example 87, except that the amount of MAC was varied to 13.8 g (118.8 mmol, [MAC]/[DEAC]=33), the amount of IPP was varied to 1.8 g (8.9 mmol, 7.1% by mol based on the total amount of DEAC and MAC) and the amount of $LiN(CF_3SO_2)_2$ was varied to 0.7 g (2.5 mmol, $[LiN(CF_3SO_2)_2]/\{[—OCOO—]$ in DEAC and MAC$\}$= 0.02).

The ionic conductivities of the resulting polymeric solid electrolyte at 80° C. and 100° C. were measured. The results are set forth in Table 7.

Example 94

Preparation of Gelled Polymeric Solid Electrolyte

A gelled polymeric solid electrolyte was prepared in the same manner as in Example 87, except that 3.6 g (30% by weight based on the total amount of DEAC and MAC) of ethylene carbonate was added to the mixed solution and the amount of $LiN(CF_3SO_2)_2$ in the solution was varied to 1.0 g (3.6 mmol, 1 mol based on 1 kg of ethylene carbonate).

The ionic conductivities of the resulting gelled polymeric solid electrolyte at −20, −10, 0, 10, 20, 30, 40, 60, 80 and 100° C. were measured. The results are set forth in Table 8.

Example 95

Preparation of Gelled Polymeric Solid Electrolyte

A gelled polymeric solid electrolyte was prepared in the same manner as in Example 94, except that the amount of ethylene carbonate was varied to 2.4 g (20% by weight based on the total amount of DEAC and MAC) and the amount of $LiN(CF_3SO_2)_2$ was varied to 0.7 g (2.4 mmol, 1 mol based on 1 1kg of ethylene carbonate).

The ionic conductivities of the resulting gelled polymeric solid electrolyte at 10, 20, 30, 40, 60, 80 and 100° C. were measured. The results are set forth in Table 8.

Example 96

Preparation of Gelled Polymeric Solid Electrolyte

A gelled polymeric solid electrolyte was prepared in the same manner as in Example 94, except that propylene carbonate was used in place of the ethylene carbonate.

The ionic conductivities of the resulting gelled polymeric solid electrolyte at −20, −10, 0, 10, 20, 30, 40, 60, 80 and 100° C. were measured. The results are set forth in Table 8.

Example 97

Preparation of Gelled Polymeric Solid Electrolyte

A gelled polymeric solid electrolyte was prepared in the same manner as in Example 96, except that the amount of propylene carbonate was varied to 2.4 g (20% by weight based on the total amount of DEAC and MAC) and the amount of LiN(CF$_3$SO$_2$)$_2$ was varied to 0.7 g (2.4 mmol, 1 mol based on 1 kg of propylene carbonate).

The ionic conductivities of the resulting gelled polymeric solid electrolyte at 30, 40, 60, 80 and 100° C. were measured. The results are set forth in Table 8.

TABLE 5

| | Formulation | | Gel fraction |
|---|---|---|---|
| Example | [MAC]/[DEAC] | IPP (mol %) | (%) |
| Ex. 73 | 26 | 7.1 | 87 |
| Ex. 74 | 26 | 3.5 | 85 |
| Ex. 75 | 26 | 2.4 | 83 |
| Ex. 76 | 26 | 1.8 | 80 |
| Ex. 77 | 26 | 1.4 | 79 |
| Ex. 78 | 26 | 1.0 | 78 |

[MAC]/[DEAC]: molar ratio of MAC to DEAC
IPP: % by mol based on the total amount of DEAC and MAC

TABLE 6

| | Formulation | | Glass transition temperature |
|---|---|---|---|
| Example | [MAC]/[DEAC] | IPP (mol %) | (° C.) |
| Ex. 73 | 26 | 7.1 | 1 |
| Ex. 79 | 31 | 7.1 | −3 |
| Ex. 80 | 28 | 7.1 | −2 |
| Ex. 81 | 24 | 7.1 | 4 |
| Ex. 82 | 21 | 7.1 | 5 |
| Ex. 83 | 10 | 7.1 | 11 |
| Ex. 84 | 6 | 7.1 | 17 |
| Ex. 85 | 4 | 7.1 | 21 |
| Ex. 86 | 2 | 7.1 | 26 |

[MAC]/[DEAC]: molar ratio of MAC to DEAC
IPP: % by mol based on the total amount of DEAC and MAC

TABLE 7

| | Formulation | | | Ionic conductivity | |
|---|---|---|---|---|---|
| | [MAC]/ | IPP | LiN(CF$_3$SO$_2$)$_2$ | (S/cm) | |
| Example | [DEAC] | (mol %) | [—OCOO—] | 100° C. | 80° C. |
| Ex. 87 | 26 | 7.1 | 0.02 | 2.3 × 10$^{-7}$ | 8.4 × 10$^{-8}$ |
| Ex. 88 | 27 | 7.1 | 0.02 | 3.8 × 10$^{-7}$ | 1.4 × 10$^{-7}$ |
| Ex. 89 | 28 | 7.1 | 0.02 | 3.5 × 10$^{-7}$ | 1.2 × 10$^{-7}$ |
| Ex. 90 | 28 | 7.1 | 0.09 | 3.3 × 10$^{-6}$ | 9.0 × 10$^{-7}$ |
| Ex. 91 | 31 | 7.1 | 0.02 | 3.6 × 10$^{-7}$ | 9.6 × 10$^{-8}$ |
| Ex. 92 | 32 | 7.1 | 0.02 | 4.6 × 10$^{-8}$ | 1.4 × 10$^{-8}$ |
| Ex. 93 | 33 | 7.1 | 0.02 | 3.5 × 10$^{-7}$ | 1.0 × 10$^{-7}$ |

[MAC]/[DEAC]: molar ratio of MAC to DEAC
IPP: % by mol based on the total amount of DEAC and MAC
LiN(CF$_3$SO$_2$)$_2$
[—OCOO—]
molar ratio of LiN(CF$_3$SO$_2$)$_2$ to [—OCOO—] in DEAC and MAC

TABLE 8

| | | Ex. 94 | Ex. 95 | Ex. 96 | Ex. 97 |
|---|---|---|---|---|---|
| Formulation | [MAC]/[DEAC] | 26 | 26 | 26 | 26 |
| | IPP | 7.1 mol % | 7.1 mol % | 7.1 mol % | 7.1 mol % |
| | Ethylene carbonate | 30 wt % | 20 wt % | | |
| | Propylene carbonate | | | 30 wt % | 20 wt % |
| | LiN(CF$_3$SO$_2$)$_2$ | 1 mol/kg | 1 mol/kg | 1 mol/kg | 1 mol/kg |
| Ionic conductivity (S/cm) | 100° C. | 6.5 × 10$^{-4}$ | 2.7 × 10$^{-4}$ | 4.9 × 10$^{-5}$ | 1.2 × 10$^{-5}$ |
| | 80° C. | 9.3 × 10$^{-4}$ | 2.9 × 10$^{-4}$ | 3.4 × 10$^{-5}$ | 6.0 × 10$^{-6}$ |
| | 60° C. | 4.9 × 10$^{-4}$ | 1.8 × 10$^{-4}$ | 1.5 × 10$^{-5}$ | 1.8 × 10$^{-6}$ |
| | 40° C. | 1.9 × 10$^{-4}$ | 7.0 × 10$^{-5}$ | 1.0 × 10$^{-5}$ | 2.7 × 10$^{-7}$ |
| | 30° C. | 1.1 × 10$^{-4}$ | 4.2 × 10$^{-5}$ | 2.5 × 10$^{-7}$ | 8.7 × 10$^{-8}$ |
| | 20° C. | 5.6 × 10$^{-5}$ | 2.4 × 10$^{-5}$ | 1.3 × 10$^{-7}$ | |
| | 10° C. | 2.1 × 10$^{-5}$ | 1.0 × 10$^{-5}$ | 3.4 × 10$^{-8}$ | |
| | 0° C. | 6.5 × 10$^{-6}$ | 2.7 × 10$^{-6}$ | | |
| | −10° C. | 1.3 × 10$^{-6}$ | 6.5 × 10$^{-7}$ | | |
| | −20° C. | 2.4 × 10$^{-7}$ | 1.5 × 10$^{-7}$ | | |

[MAC]/[DEAC]: molar ratio of MAC to DEAC
IPP: % by mol based on the total amount of DEAC and MAC
Ethylene carbonate, Propylene carbonate: % by weight based on the total amount of DEAC and MAC
LiN(CF$_3$SO$_2$)$_2$: molar concentration based on 1 kg of ethylene carbonate or propylene carbonate

We claim:

1. A polymeric solid electrolyte comprising at least one of the following:

at least one acrylic ester polymer comprising structural units derived from at least one acrylic ester selected from the group consisting of acrylic esters of the general formula (II):

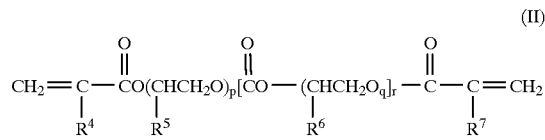

wherein $R^4$ to $R^7$ may be identical to or different from each other and each represents a hydrogen atom or an alkyl group having 1 to 4 carbons; and p, q and r may be identical to or different from each other and each is an integer from 1 to 100;

at least one allyl ether polymer comprising structural units derived from at least one allyl ether selected from the group consisting of allyl ethers of the general formula (III):

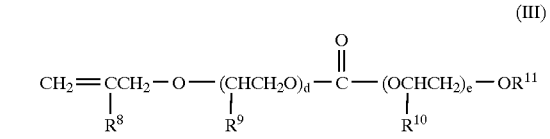

wherein $R^8$, $R^9$ and $R^{10}$ may be identical to or different from each other and each represents a hydrogen atom, an alkyl group having 1 to 4 carbon atoms; $R^{11}$ represents an alkyl group having 1 to 4 carbon atoms or CH$_2$CR$^{12}$=CH$_2$ in which $R^{12}$ is hydrogen or a methyl group, d is an integer of 0 to 100, and e is an integer of 0 to 100; or at least one allyl carbonate polymer comprising structural units derived from at least one allyl carbonate selected from the group consisting of allyl carbonates of the general formula (IV):

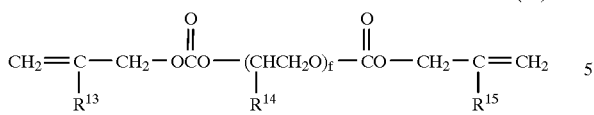   (IV)

wherein $R^{13}$, $R^{14}$ and $R^{15}$ may be identical to or different from each other and each represents a hydrogen atom or an alkyl group having 1 to 4 carbon atoms, and f is an integer of 1 to 100;

and a salt of a metal of Group Ia of the periodic table.

2. The polymeric solid electrolyte of claim 1, wherein said at least one acrylic ester polymer is in homopolymer or copolymer form.

3. The polymeric solid electrolyte of claim 2, wherein said at least one acrylic ester polymer is a copolymer of (1) said at least one acrylic ester polymer and (2) at least one compound selected from the group consisting of the compounds represented by general formulae (V) to (VIII):

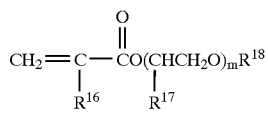   (V)

wherein $R^{16}$ and $R^{17}$ may be identical to or different from each other and each represents a hydrogen atom or an alkyl group having 1 to 4 carbon atoms; $R^{18}$ represents an alkyl group having 1 to 4 carbon atoms; and m is an integer of 0 to 100;

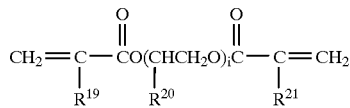   (VI)

wherein $R^{19}$, $R^{20}$ and $R^{21}$ may be identical to or different from each other an each represents a hydrogen atom or an alkyl group having 1 to 4 carbon atoms; and i is an integer of 1 to 100,

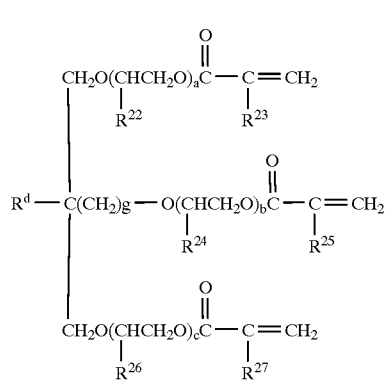   (VII)

wherein $R^{22}$ to $R^{27}$ may be identical to or different from each other and each represents a hydrogen atom or an alkyl group having 1 to 4 carbon atoms; and a, b and c may be identical to or different from each other and each is an integer of 0 to 100; and where $R^d$ is H, g is zero, or where $R^d$ is $CH_2CH_3$, g is 1; and

   (VIII)

wherein k is an integer of 1 to 100.

4. The polymeric solid electrolyte of claim 1, wherein said at least one allyl ether polymer is in homopolymer or copolymer form.

5. The polymeric solid electrolyte of claim 4, wherein said at least one allyl ether polymer is a copolymer of (1) at least one allyl ether polymer and (2) and at least one compound selected from the group consisting of the compounds represented by general formulae (IV) to (VII):

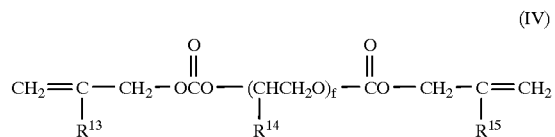   (IV)

wherein $R^{13}$, $R^{14}$ and $R^{15}$ may be identical to or different from each other and each represents a hydrogen atom or an alkyl group having 1 to 4 carbon atoms, and f is an integer of 1 to 100;

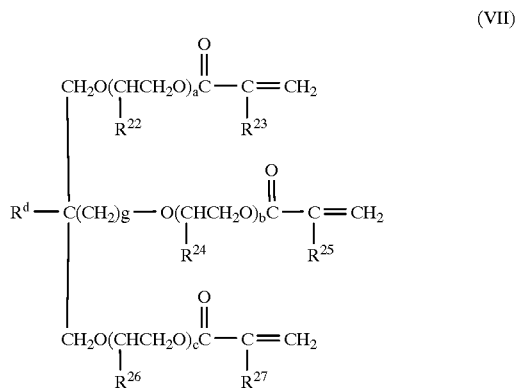   (VII)

wherein $R^{22}$ to $R^{27}$ may be identical to or different from each other and each represents a hydrogen atom or an alkyl group having 1 to 4 carbon atoms; and a, b and c may be identical to or different from each other and each is an integer of 0 to 100; and where $R^d$ is H, g is zero, or where $R^d$ is $CH_2CH_3$, g is 1;

and the following general formulae:

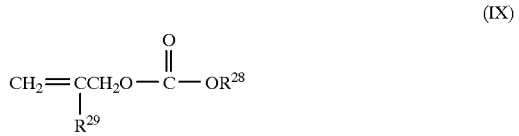   (IX)

wherein $R^{28}$ represents an alkyl group having 1 to 4 carbon atoms; and $R^{29}$ represents a hydrogen or an alkyl group having 1 to 4 carbon atoms, and $$CH_2=\underset{R^{30}}{C}CH_2O-\overset{O}{\underset{\|}{C}}-OCH_2\underset{R^{31}}{C}=CH_2 \qquad (X)$$

wherein each of $R^{30}$ and $R^{31}$ represents a hydrogen atom or an alkyl group having 1 to 4 carbon atoms.

6. The polymeric solid electrolyte of claim 1, wherein said at least one allyl carbonate polymer is in homopolymer or copolymer form.

7. The polymeric solid electrolyte of claim 6, wherein the at least one allyl carbonate polymer is a copolymer of (1) said at least one allyl carbonate polymer and (2) at least one compound selected from the group consisting of the compounds represented by general formula (VII), (IX) and (X):

$$R^d-C(CH_2)_g\begin{pmatrix} CH_2O(CHCH_2O)_a\overset{O}{\underset{\|}{C}}-\underset{R^{23}}{C}=CH_2 \\ \underset{R^{22}}{|} \\ -O(CHCH_2O)_b\overset{O}{\underset{\|}{C}}-\underset{R^{25}}{C}=CH_2 \\ \underset{R^{24}}{|} \\ CH_2O(CHCH_2O)_c\overset{O}{\underset{\|}{C}}-\underset{R^{27}}{C}=CH_2 \\ \underset{R^{26}}{|} \end{pmatrix} \qquad (VII)$$

where $R^{22}$ to $R^{27}$ may be identical to or different from each other and each represents a hydrogen atom or an alkyl group having 1 to 4 carbon atoms; and a, b and c may be identical to or different from each other and each is an integer of 0 to 100; and wherein $R^d$ is H, g is zero, or where $R^d$ is $CH_2CH_3$, g is 1;

$$CH_2=\underset{R^{29}}{C}CH_2O-\overset{O}{\underset{\|}{C}}-OR^{28} \qquad (IX)$$

wherein $R^{28}$ represents an alkyl group having 1 to 4 carbon atoms; and $R^{29}$ represents a hydrogen atoms or an alkyl group having 1 to 4 carbon atoms, and $$CH_2=\underset{R^{30}}{C}CH_2O-\overset{O}{\underset{\|}{C}}-OCH_2\underset{R^{31}}{C}=CH_2 \qquad (X)$$

wherein each of $R^{30}$ and $R^{31}$ represents a hydrogen atom or an alkyl group having 1 to 4 carbon atoms.

8. The polymeric solid electrolyte of claim 6, wherein the allyl carbonate polymer is copolymer form comprises structural units derived from at least one compound selected from the group consisting of the compounds represented by general formula (VII):

$$R^d-C(CH_2)_g\begin{pmatrix} CH_2O(CHCH_2O)_a\overset{O}{\underset{\|}{C}}-\underset{R^{23}}{C}=CH_2 \\ \underset{R^{22}}{|} \\ -O(CHCH_2O)_b\overset{O}{\underset{\|}{C}}-\underset{R^{25}}{C}=CH_2 \\ \underset{R^{24}}{|} \\ CH_2O(CHCH_2O)_c\overset{O}{\underset{\|}{C}}-\underset{R^{27}}{C}=CH_2 \\ \underset{R^{26}}{|} \end{pmatrix} \qquad (VII)$$

where $R^{22}$ to $R^{27}$ may be identical to or different from each other and each represents a hydrogen atom or an alkyl group having 1 to 4 carbon atoms; and a, b and c may be identical to or different from each other and each is an integer of 0 to 100; and wherein $R^d$ is H, g is zero, or where $R^d$ is $CH_2CH_3$, g is 1;

and structural units derived from at least one compound selected from the group consisting of the compounds represented by general formula (IX):

$$CH_2=\underset{R^{29}}{C}CH_2O-\overset{O}{\underset{\|}{C}}-OR^{28} \qquad (IX)$$

wherein $R^{28}$ represents an alkyl group having 1 to 4 carbon atoms; and $R^{29}$ represents a hydrogen atom or an alkyl group having 1 to 4 carbon atoms.

9. The polymeric solid electrolyte of claim 6, wherein the allyl carbonate polymer in copolymer form comprises structural units derived from at least one compound selected from the group consisting of the compounds represented by general formula (VII):

$$R^d-C(CH_2)_g\begin{pmatrix} CH_2O(CHCH_2O)_a\overset{O}{\underset{\|}{C}}-\underset{R^{23}}{C}=CH_2 \\ \underset{R^{22}}{|} \\ -O(CHCH_2O)_b\overset{O}{\underset{\|}{C}}-\underset{R^{25}}{C}=CH_2 \\ \underset{R^{24}}{|} \\ CH_2O(CHCH_2O)_c\overset{O}{\underset{\|}{C}}-\underset{R^{27}}{C}=CH_2 \\ \underset{R^{26}}{|} \end{pmatrix} \qquad (VII)$$

where $R^{22}$ to $R^{27}$ may be identical to or different from each other and each represents a hydrogen atom or an alkyl group having 1 to 4 carbon atoms; and a, b and c may be identical to or different from each other and each is an integer of 0 to 100; and wherein $R^d$ is H, g is zero, or where $R^d$ is $CH_2CH_3$, g is 1;

and structural units derived from at least one compound selected from the group consisting of the compounds represented by general formula (X):

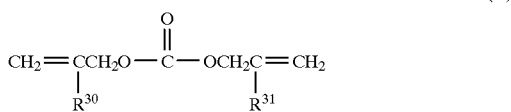

(X)

wherein each of $R^{30}$ and $R^{31}$ represents a hydrogen atom or an alkyl group having 1 to 4 carbon atoms.

10. A gelled polymeric solid electrolyte comprising at least one of the following:

at least one acrylic ester polymer comprising structural units derived from at least one acrylic ester selected from the group consisting of acrylic esters of the general formula (II):

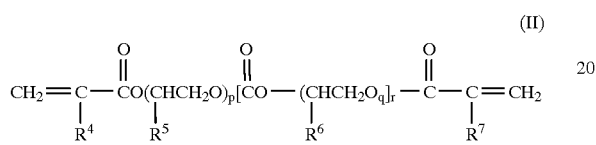

(II)

wherein $R^4$ to $R^7$ may be identical to or different from each other and each represents a hydrogen atom or an alkyl group having 1 to 4 carbons; and p, q and r may be identical to or different from each other and each is an integer from 1 to 100; and at least one allyl ether polymer comprising structural units derived from at least one allyl ether selected from the group consisting of allyl ethers of the general formula (III):

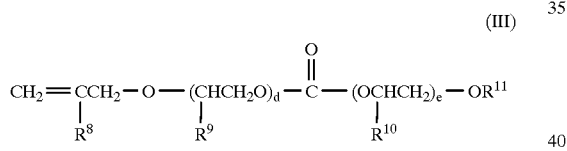

(III)

wherein $R^8$, $R^9$ and $R^{10}$ may be identical to or different from each other and each represents a hydrogen, an alkyl group having 1 to 4 carbon atoms; $R^{11}$ represents an alkyl group having 1 to 4 carbon atoms or $CH_2CR^{12}=CH_2$ in which $R^{12}$ is hydrogen or a methyl group, d is an integer of 0 to 100, and e is an integer of 0 to 100;

at least one allyl carbonate polymer comprising structural units derived from at least one allyl carbonate selected from the group consisting of allyl carbonates of the general formula (IV):

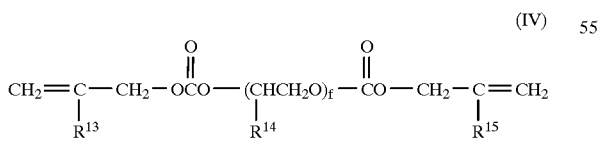

(IV)

wherein $R^{13}$, $R^{14}$ and $R^{15}$ may be identical to or different from each other and each represents a hydrogen atom or an alkyl group having 1 to 4 carbon atoms, and f is an integer of 1 to 100;

a salt of a metal of Group Ia of the periodic table; and a nonaqueous solvent.

11. The gelled polymeric solid electrolyte of claim 10, wherein said at least one acrylic ester polymer is in homopolymer or copolymer form.

12. The gelled polymeric solid electrolyte of claim 11, wherein said at least one acrylic ester polymer is a copolymer of (1) said at least one acrylic ester polymer and (2) at least one compound selected from the group consisting of the compounds represented by general formulae (V) to (VIII):

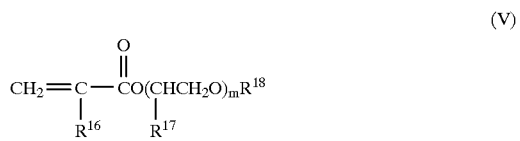

(V)

wherein $R^{16}$ and $R^{17}$ may be identical to or different from each other and each represents a hydrogen atom or an alkyl group having 1 to 4 carbon atoms; $R^{18}$ represents an alkyl group having 1 to 4 carbon atoms; and m is an integer of 0 to 100;

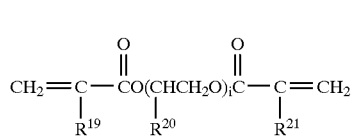

(VI)

wherein $R^{19}$, $R^{20}$ and $R^{21}$ may be identical to or different from each other an each represents a hydrogen atom or an alkyl group having 1 to 4 carbon atoms; and i is an integer of 1 to 100,

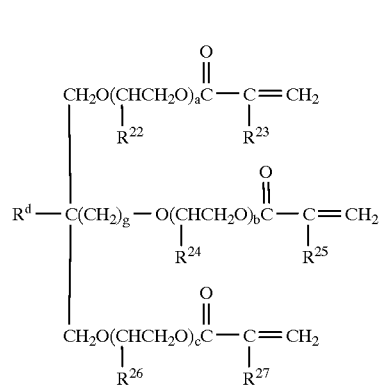

(VII)

wherein $R^{22}$ to $R^{27}$ may be identical to or different from each other and each represents a hydrogen atom or an alkyl group having 1 to 4 carbon atoms; and a, b and c may be identical to or different from each other and each is an integer of 0 to 100; and where $R^d$ is H, g is zero, or where $R^d$ is $CH_2CH_3$, g is 1; and

$HO-(CH_2CH_2O)_k-H$ (VIII)

wherein k is an integer of 1 to 100.

13. The gelled polymeric solid electrolyte of claim 10, wherein said at least one allyl ether polymer is in homopolymer or copolymer form.

14. The gelled polymeric solid electrolyte of claim 13, wherein said at least one allyl ether polymer is a copolymer of (1) at least one allyl ether polymer and (2) and at least one compound selected from the group consisting of the compounds represented by general formulae (IV) and (VII):

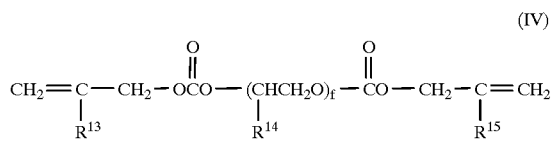
(IV)

wherein $R^{13}$, $R^{14}$ and $R^{15}$ may be identical to or different from each other and each represents a hydrogen atom or an alkyl group having 1 to 4 carbon atoms, and f is an integer of 1 to 100;

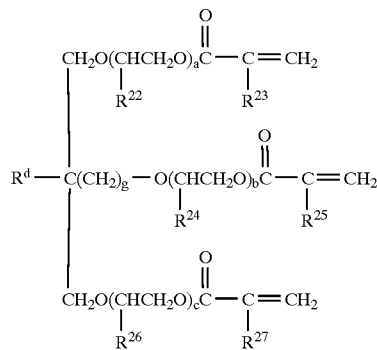
(VII)

wherein $R^{22}$ to $R^{27}$ may be identical to or different from each other and each represents a hydrogen atom or an alkyl group having 1 to 4 carbon atoms; and a, b and c may be identical to or different from each other and each is an integer of 0 to 100; and where $R^d$ is H, g is zero, or where $R^d$ is $CH_2CH_3$, g is 1;
and the following general formula:

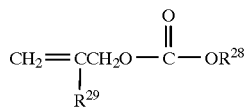
(IX)

wherein $R^{28}$ represents an alkyl group having 1 to 4 carbon atoms; and $R^{29}$ represents a hydrogen or an alkyl group having 1 to 4 carbon atoms, and

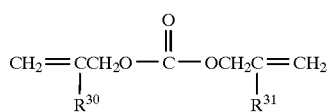
(X)

wherein each of $R^{30}$ and $R^{31}$ represents a hydrogen atom or an alkyl group having 1 to 4 carbon atoms.

15. The gelled polymeric solid electrolyte of claim 10, wherein said at least one allyl carbonate polymer is in homopolymer or copolymer form.

16. The gelled polymeric solid electrolyte of claim 15, wherein the at least one allyl carbonate polymer is a copolymer of (1) said at least one allyl carbonate polymer and (2) at least one compound selected from the group consisting of the compounds represented by general formulae (VII), (IX) and (X):

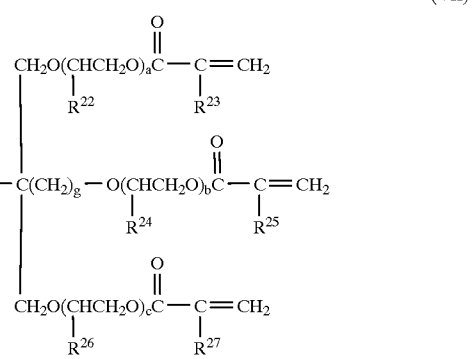
(VII)

wherein $R^{22}$ to $R^{27}$ may be identical to or different from each other and each represents a hydrogen atom or an alkyl group having 1 to 4 carbon atoms; and a, b and c may be identical to or different from each other and each is an integer of 0 to 100; and where $R^d$ is H, g is zero, or where $R^d$ is $CH_2CH_3$, g is 1; and

(IX)

wherein $R^{28}$ represents an alkyl group having 1 to 4 carbon atoms; and $R^{29}$ represents a hydrogen or an alkyl group having 1 to 4 carbon atoms, and

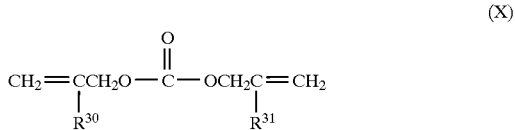
(X)

wherein each of $R^{30}$ and $R^{31}$ represents a hydrogen atom or an alkyl group having 1 to 4 carbon atoms.

17. The polymeric solid electrolyte of claim 15, wherein the allyl carbonate polymer in copolymer form comprises structural units derived from at least one compound selected from the group consisting of the compounds represented by general formula (VII):

general formula (VII):

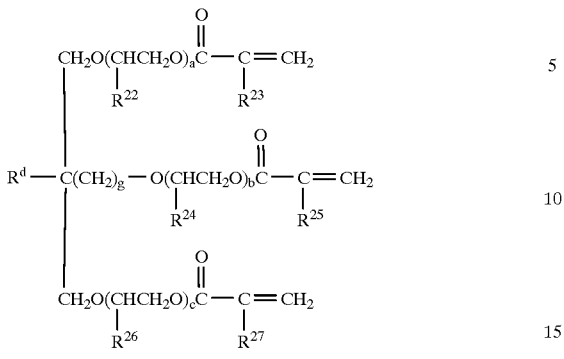

where $R^{22}$ to $R^{27}$ may be identical to or different from each other and each represents a hydrogen atom or an alkyl group having 1 to 4 carbon atoms; and a, b and c may be identical to or different from each other and each is an integer of 0 to 100; and where $R^d$ is H, g is zero, or where $R^d$ is $CH_2CH_3$, g is 1;

and structural units derived from at least one compound selected from the group consisting of the compounds represented by general formula (IX):

wherein $R^{28}$ represents an alkyl group having 1 to 4 carbon atoms; and $R^{29}$ represents a hydrogen atom or an alkyl group having 1 to 4 carbon atoms.

18. The polymeric solid electrolyte of claim 15, wherein the allyl carbonate polymer in copolymer form comprises structural units derived from at least one compound selected from the group consisting of the compounds represented by general formula (VII):

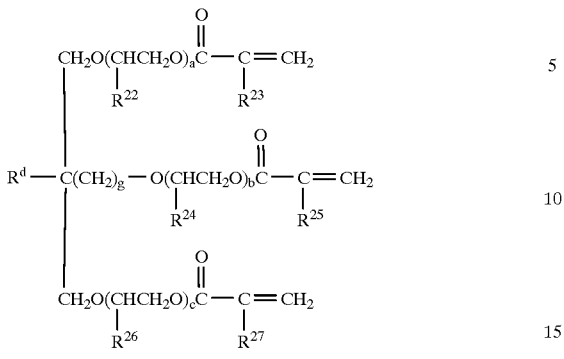

where $R^{22}$ to $R^{27}$ may be identical to or different from each other and each represents a hydrogen atom or an alkyl group having 1 to 4 carbon atoms; and a, b and c may be identical to or different from each other and each is an integer of 0 to 100; and wherein $R^d$ is H, g is zero, or where $R^d$ is $CH_2CH_3$, g is 1;

and structural units derived from at least one compound selected from the group consisting of the compounds represented by general formula (X):

$$CH_2=C(R^{30})CH_2O-C(=O)-OCH_2C(R^{31})=CH_2$$

wherein each of $R^{30}$ and $R^{31}$ represents a hydrogen atom or an alkyl group having 1 to 4 carbon atoms.

* * * * *